(12) United States Patent
Voudouris

(10) Patent No.: US 6,168,428 B1
(45) Date of Patent: Jan. 2, 2001

(54) ORTHODONTIC BRACKET

(76) Inventor: John C. Voudouris, 16 Doon Rd., Willowdale, Ontario (CA), M2L 1L9

(*) Notice: Under 35 U.S.C. 154(b), the term of this patent shall be extended for 0 days.

(21) Appl. No.: 09/308,194
(22) PCT Filed: Nov. 12, 1997
(86) PCT No.: PCT/CA97/00865
    § 371 Date: Jul. 23, 1999
    § 102(e) Date: Jul. 23, 1999
(87) PCT Pub. No.: WO98/20805
    PCT Pub. Date: May 22, 1998
(51) Int. Cl.⁷ .................................................. A61C 3/00
(52) U.S. Cl. ........................................ 433/11; 433/13
(58) Field of Search .............................. 433/10, 11, 13, 433/14

(56) References Cited

U.S. PATENT DOCUMENTS

| | | |
|---|---|---|
| 3,772,787 | 11/1973 | Hanson . |
| 4,077,126 | 3/1978 | Pletcher . |
| 4,144,642 | 3/1979 | Wallshein . |
| 4,197,642 | 4/1980 | Wallshein . |
| 4,248,588 | 2/1981 | Hanson . |
| 4,419,078 | 12/1983 | Pletcher . |
| 4,559,012 | 12/1985 | Pletcher . |
| 4,561,844 | 12/1985 | Bates . |
| 4,634,661 | 1/1987 | Cavallaro . |
| 4,655,708 | 4/1987 | Fujita . |
| 4,698,017 | 10/1987 | Hanson . |
| 4,712,999 | 12/1987 | Rosenberg . |
| 4,786,242 | 11/1988 | Barsk . |
| 5,094,614 | * 3/1992 | Wildman ............................ 433/14 |
| 5,248,257 | * 9/1993 | Cannon ............................. 433/14 |
| 5,322,435 | * 6/1994 | Pletcher ........................... 433/11 |
| 5,474,445 | 12/1995 | Voudouris . |

FOREIGN PATENT DOCUMENTS 44 07 100    9/1995  (DE) .

* cited by examiner

Primary Examiner—Todd E Manahan
(74) Attorney, Agent, or Firm—Kenyon & Kenyon

(57) ABSTRACT

In one embodiment, a pre-engaging orthodontic bracket includes a body having a lingual surface for attachment to a tooth, a pair of laterally spaced gingival tie wings and a pair of laterally spaced occlusal tie wings. The gingival and occlusal tie wings project from a labial surface of the body. An archwire slot extends mesiodistally across the body and between the gingival and occlusal tie wings at opposed mesial and distal sides of the body to accomodate an archwire. A shutter is moveable between an open position in which placement and removal of an archwire is facilitated, and a closed position in which placement and removal of an archwire is inhibited.

14 Claims, 59 Drawing Sheets

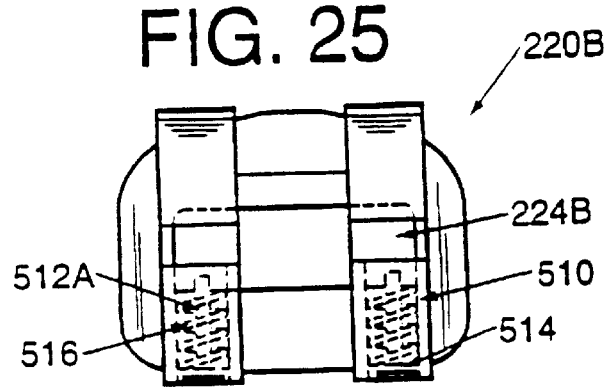
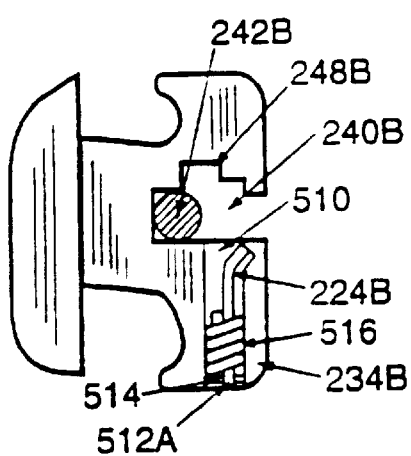
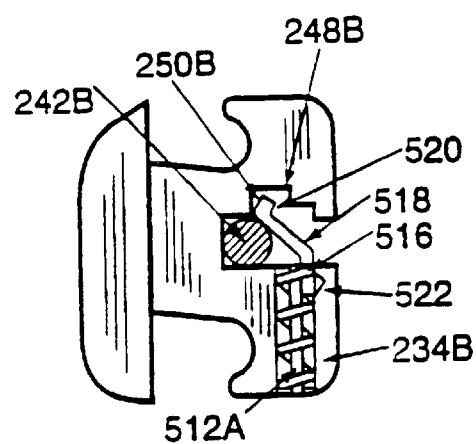

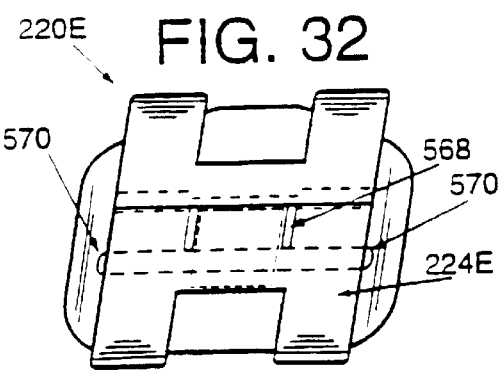
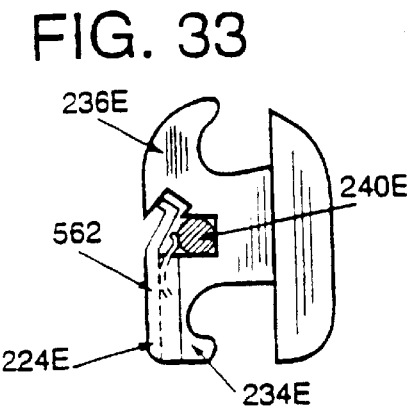
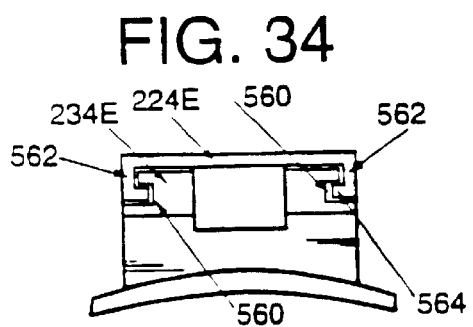
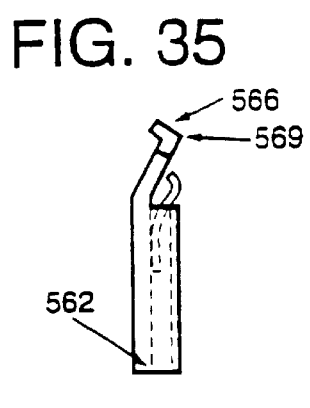
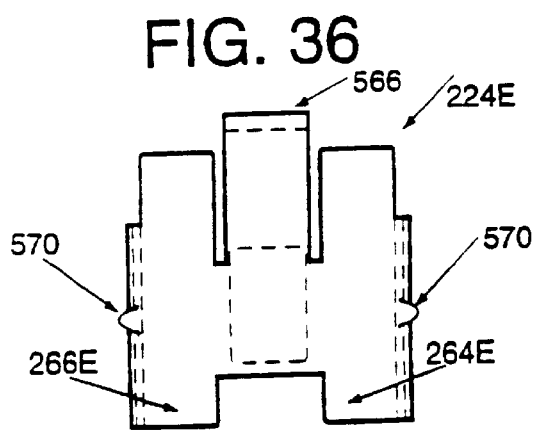

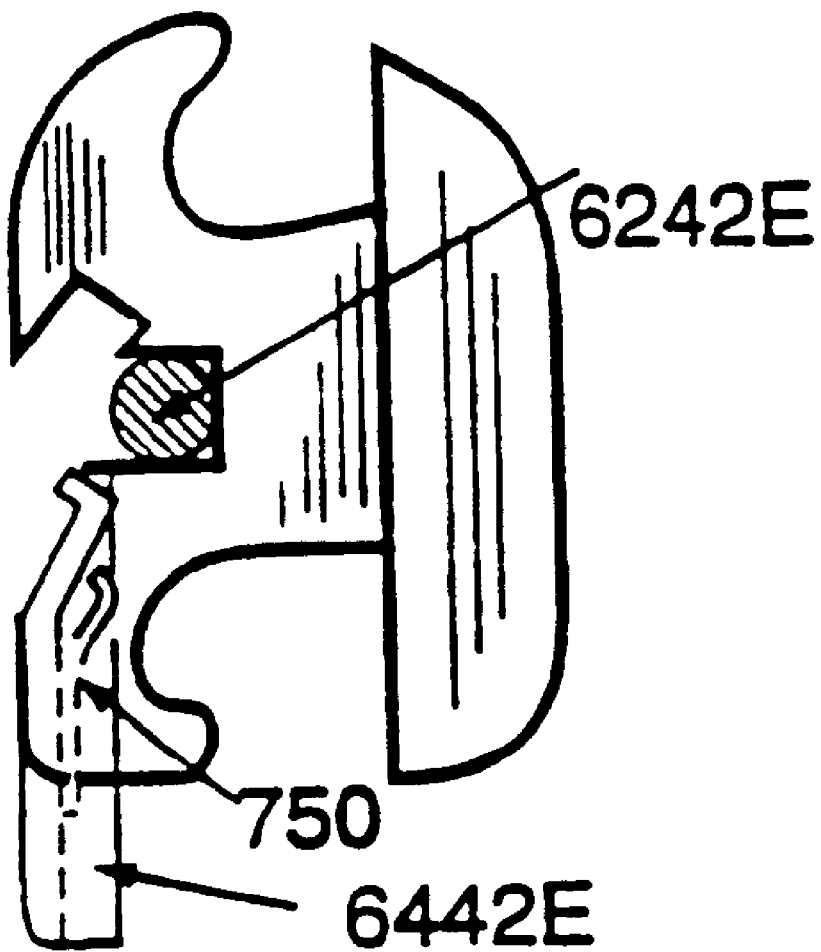

FIG. 102
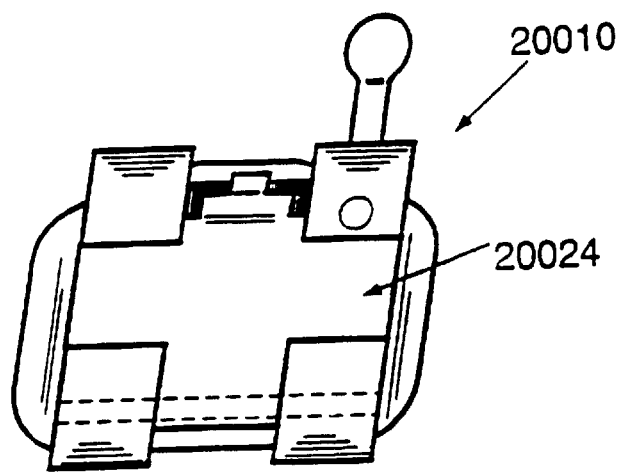
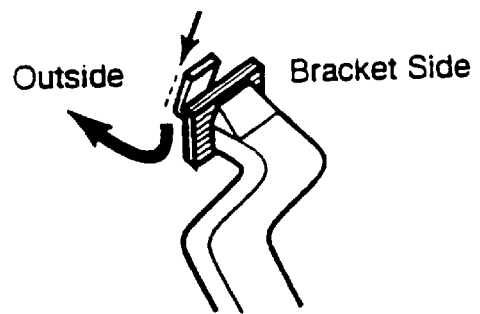
FIG 103
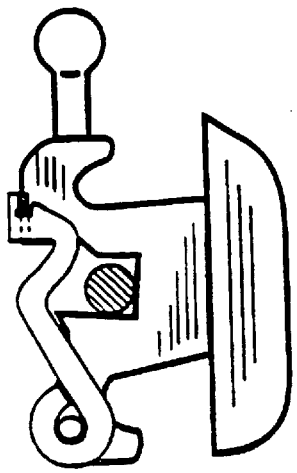

ORTHODONTIC BRACKET

FIELD OF THE INVENTION

The present invention relates in general to pre-engaging orthodontic brackets and in particular to a pre-engaging twin orthodontic bracket and to a plurality of orthodontic brackets forming a set of braces.

BACKGROUND OF THE INVENTION

According to established orthodontic techniques, it is well known that one is able to ligate an archwire to a bracket utilizing an elastic, elastomeric or metal ligature. In a twin edgewise-orthodontic bracket, the elastic ligature is stretched around respective undercuts of gingival and occlusal tie wings so as to overlay the archwire at mesial and distal ends of the bracket.

The ligating procedure involves carefully stretching the elastic or elastomeric ligature (or wrapping and twisting a metal ligature) around the tie wings utilizing appropriate orthodontic instruments. It has been found that the time-consuming ligation procedure contributes to lengthy chair time. Furthermore, the elastic ligatures are known to lose their elasticity with time and are subject to degradation. Also, the elastic and metal ligatures have been known to trap food particles in areas of the bracket, which are difficult for the patient to clean, and to increase the level of friction against the archwire. Finally, the use of sharp metal ligatures around the bracket can subject the clinician to unnecessary exposure to infectious bacteria, or viruses such as hepatitis B, or possibly the HIV virus particularly in blood.

In an effort to overcome these disadvantages of elastic ligatures, certain advances have been made in the area of pre-engaging orthodontic brackets.

Each of U.S. Pat. Nos. 4,144,642; 4,248,588; 4,698,017; 3,772,787; 4,786,242; 4,559,012; 4,561,844; 4,655,708; 4,077,126; 4,419,078; 4,634,661; 4,197,642; and 4,712,999 illustrate one or more designs of pre-engaging brackets.

These prior art devices overcome some of the disadvantages associated with elastic ligatures. For example, pre-engaging orthodontic brackets eliminate, or at least reduce, exposure of the clinician to sharp ligatures, thereby alleviating the problem of contracting harmful bacteria or viruses. In addition, pre-engaging orthodontic brackets permit continuous low deflection differential archwire contact separately for both round and rectangular archwires at least two different levels of contact, which is not possible with degrading elastic, elastomeric or rigid, high deflection metal ligatures. However, most of the known prior art pre-engaging orthodontic brackets lack the reliability and the accessible ease of operability that most clinicians require.

In addition, the majority of prior art pre-engaging orthodontic brackets are of a single design that have three or fewer tie wings.

It is therefore an object of the present invention to provide a novel twin pre-engaging orthodontic bracket which obviates or mitigates at least one of the above-identified disadvantages associated with prior art orthodontic brackets.

SUMMARY OF THE INVENTION

According to one aspect of the present invention there is provided a pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings at opposed mesial and distal sides of said body being separated by an interwing region of said body;

an archwire slot extending mesiodistally across said body and between the gingival and occlusal tie wings at opposed mesial and distal sides of said body to accommodate an archwire, said archwire slot being interrupted by said interwing region;

a locking shutter moveable relative to said body between an open position in which placement and removal of said archwire in said archwire slot is facilitated and a closed position in which placement and removal of said archwire in said archwire slot is inhibited; and biasing means carried by said locking shutter and engageable with an archwire in said archwire slot when said locking shutter is in said closed position, said biasing means resiliently urging said archwire into said archwire slot to provide a continuous corrective force thereon.

In one embodiment, the biasing means is in the form of a leaf spring secured to the locking shutter. The leaf spring can extend mesiodistally or occlusio gingivally. In another embodiment, the locking shutter is formed of resilient material and biases the archwire when the locking shutter is in the closed position thereby to constitute the biasing means.

According to another aspect of the present invention there is provided a pre-engaging orthodontic bracket for attaching an archwire to a tooth comprising:

a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings at opposed mesial and distal sides of said body being separated by an interwing region of said body;

an archwire slot extending mesiodistally across said body and between the gingival and occlusal tie wings at opposed mesial and distal sides of said body to accommodate an archwire, said archwire slot being interrupted by said interwing region;

a locking shutter movable relative to said body between an open position in which placement and removal of said archwire in said archwire slot is facilitated and a closed position in which placement and removal of said archwire from said archwire slot is inhibited; and biasing means engageable with an archwire in said archwire slot when said locking shutter is in said closed position to urge said archwire toward said locking shutter to provide a continuous corrective force thereon.

In one embodiment, the biasing means is in the form of a resilient spring member extending mesiodistally along the archwire slot and secured to the body. The spring member has at least one free end and can be dimensioned to engage an archwire either within the archwire slot or exterior to the archwire slot. In another embodiment, the resilient spring member extends occlusogingivally across the archwire slot in the interwing region and is secured to the body adjacent one end thereof.

In another embodiment, the biasing means is in the form of magnetized elements within the body adjacent the archwire slot to present a repelling magnetic force to the archwire to bias the archwire towards the locking shutter. In yet another embodiment, the biasing means is in the form of a pair of spring-loaded pistons accommodated by the body adjacent opposed mesial and distal end of the archwire slot to urge the archwire towards the locking shutter.

According to still yet another aspect of the present invention there is provided a pre-engaging orthodontic bracket for attaching an archwire to a tooth comprising;

a body having a lingual surface for attachment to a tooth, a pair of laterally spaced gingival tie wings and a pair of laterally spaced occlusal tie wings, said gingival and occlusal tie wings projecting from a labial surface of said body, both said gingival tie wings and occlusal tie wings at opposed mesial and distal sides of said body being separated by an interwing region of said body;

an archwire slot extending mesiodistally across said body and between the gingival and occlusal tie wings at opposed mesial and distal sides of said body to accommodate an archwire, said archwire slot being interrupted by said interwing region; and a locking shutter pivotal about at least one pivot pin between an open position in which placement and removal of said archwire In said archwire slot is facilitated and a closed position in which placement of said archwire in said archwire slot is inhibited.

In one embodiment, the orthodontic bracket includes one pivot pin extending between the tie wings of one of the two pairs and wherein the locking shutter includes a single loop at one end thereof to surround the pivot pin. In another embodiment, the orthodontic bracket includes a pair of pivot pins, each accommodated by each tie wing of one of the two pairs. In this case, the locking shutter includes a pair of laterally spaced single loops surrounding the pivot pins.

Preferably, the locking shutter includes a marker thereon to identify generally the center of the archwire slot when the looking shutter is in the closed position. It is also preferred that the orthodontic bracket further includes a lubricating or sealing agent carried by one or more of the body, archwire slot, locking shutter and archwire.

According to still yet another aspect of the present invention there is provided a body for an orthodontic bracket having a mesiodistally extending archwire slot formed therein and gingival and occlusal surfaces shaped to deflect food debris and plaque mesially and distally therefrom when secured to a tooth.

According to still yet another aspect of the present invention there is provided a set of braces including a plurality or orthodontic brackets to be attached to an individual's teeth, said braces including self-engaging twin orthodontic brackets to be attached to the central and lateral teeth and first and second molars of said individual and single orthodontic brackets to be attached to the cuspid and premolar teeth of said individual.

Acccording to another aspect of the present invention a self engaging orthodontic bracket for attaching an archwire to a tooth is provided comprising:

a body including a base for attachment to the tooth. The base has an occlusal-gingivally extending opening, a lingual vertical slot, a pair of laterally spaced gingival tie wings and a pair of laterally placed occlusal tie wings. The gingival and occlusal tie wings project from a labial surface of said body. Either the occlusal tie wings or the gingival tie wings define two vertical grooves for receiving two arm members of a locking shutter through them.

an archwire slot that extends mesiodistally across the body and between the gingival and occlusal tie wings at opposed mesial and distal sides of the body to accommodate the archwire;

a resilient locking shutter that includes a lingual guide bar slidably received in the lingual vertical slot and two laterally spaced apart resilient arm members that are slidably received in the vertical grooves. The locking shutter is movable between an open position in which placement and removal of said archwire is facilitated and a closed position in which placement and removal of said archwire is inhibited;

The present invention provides advantages in that the orthodontic brackets provide predictability and accurate control of tooth movement while enhancing treatment progress. The orthodontic brackets are aesthetically pleasing due to their symmetrical designs and provide for easier hygiene than prior art orthodontic brackets.

BRIEF DESCRIPTION OF THE DRAWINGS

Preferred embodiments of the present invention will now be described more fully with reference to the accompanying drawings, in which:

FIG. 17b is a side elevational view of the orthodontic bracket shown in FIG. 17a;

FIG. 25 is a front elevational view of a further embodiment of an orthodontic bracket in accordance with the present invention having a resiliently biased locking shutter;

FIG. 26 is a side elevational view of the orthodontic bracket of FIG. 25 in an open position;

FIG. 27 is a side elevational view of the orthodontic bracket of FIG. 25 in a closed position;

FIG. 32 is a front elevational view of yet another embodiment of an orthodontic bracket in accordance with the present invention;

FIG. 33 is a side elevational view of the orthodontic bracket of FIG. 32;

FIG. 34 is an occlusal view of the orthodontic bracket of FIG. 32;

FIG. 35 is a side elevational view of a shutter forming part of the orthodontic bracket of FIG. 32;

FIG. 36 is a front elevational view of the shutter of FIG. 35;

FIG. 60b is a side elevational view of the orthodontic bracket of FIG. 59 in an open position:

FIG. 92b is a side elevational view of the orthodontic bracket of FIG. 92a;

FIG. 92c is a top plan view of the orthodontic bracket of FIG. 92a;

FIG. 92d is another side elevational view of the orthodontic bracket of FIG. 92a;

FIG. 100d is a cross-sectional view of an alternative embodiment of a locking shutter retainer for the orthodontic bracket of FIG. 100a;

FIGS. 102 and 103 are front and side elevational views of another embodiment of an orthodontic bracket in accordance with the present invention;

FIG. 107C is a front elevation view of the orthodontic bracket of FIG. 107A;

FIG. 107D is a top or occlusal view of the orthodontic bracket of FIG. 107A;

FIG. 107E is a top view of the arm or shutter in a flattened state that inserts into the orthodontic bracket of FIG. 107A;

FIG. 107F is a front elevational view of the arm in the folded shape that inserts into the orthodontic bracket of FIG. 107A;

FIG. 107G is a side elevation view of the arm in the folded shape that inserts into the orthodontic bracket of FIG. 107A

DETAILED DESCRIPTION OF THE PREFERRED EMBODIMENT

Figure 1:
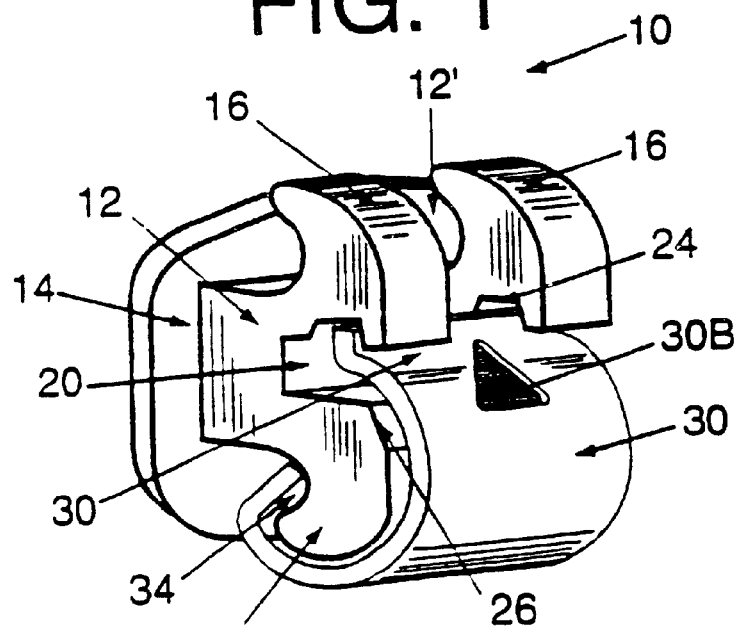
FIG. 1 is a perspective view of a pre-engaging twin orthodontic bracket in accordance with the present invention.

Referring now to FIGS. 1 and 2, a pre-engaging twin orthodontic bracket is shown and is generally indicated to by reference numeral 10. As can be seen, orthodontic bracket 10 includes a body 12 and a lingual mounting pad 14 attached to the body. The mounting pad 14 has a lingual surface to be attached to a tooth. A pair of laterally spaced gingival tie wings 16 and a pair of laterally spaced occlusal tie wings 18 extend from a labial surface of the body 12. The gingival tie wings 16 and the occlusal tie wings 18 curve lingually. An archwire slot 20 extends mesiodistally across the body and between the gingival and occlusal tie wings at opposed mesial and distal sides of the body and opens labially to receive an archwire. The archwire slot 20 is interrupted in the interwing region 12' of the body. A V-shaped deflection notch is formed in the gingival wall of the archwire slot 20 at its mesial and distal ends extends to define mesial and distal bevelled deflection surfaces 24 above the archwire slot. Resting grooves 26 are formed in the labial surface of the wings 15 below the archwire slot 20.

Figure 2A:
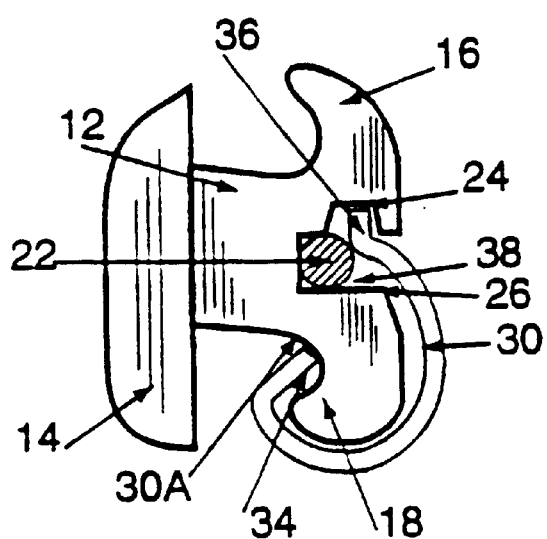
FIG. 2a is a side elevational view of the orthodontic bracket of FIG. 1
Figure 2B:
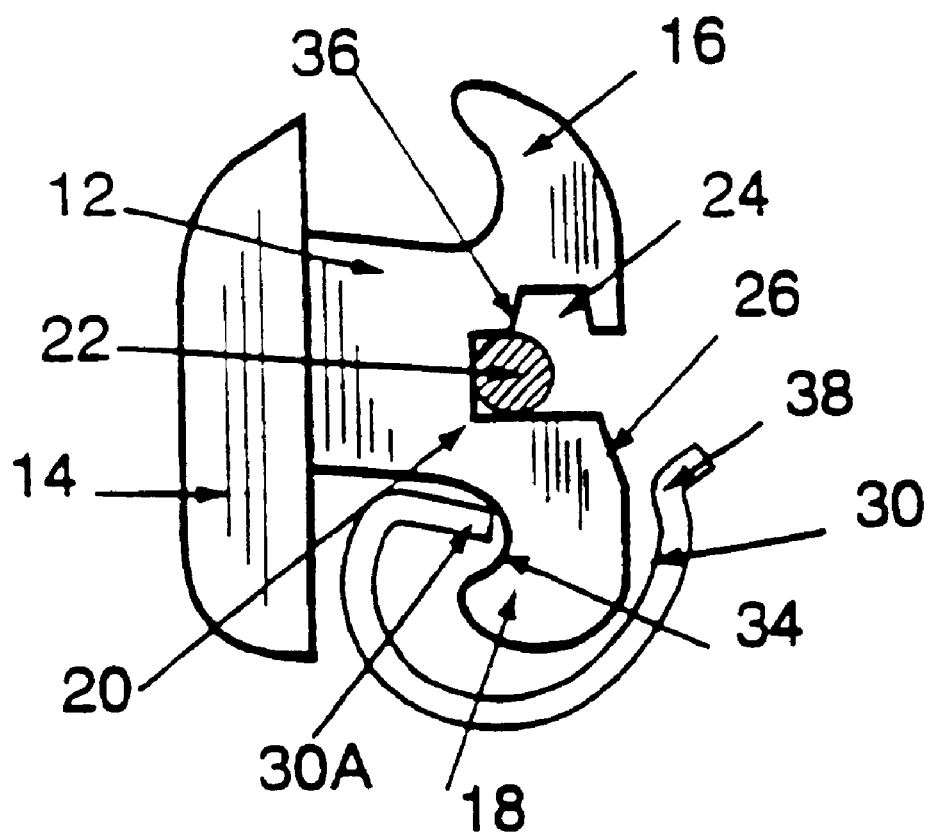
FIG. 2b is a side elevational view of the orthodontic bracket of FIG. 1 in an open position.

A shutter 30 formed of resilient stainless steel is pivotally mounted on the occlusal tie wings 18 and is movable between a closed position where access to the archwire slot 20 is inhibited and an open position where access to the archwire slot is permitted (see FIGS. 2a and 2b). One end 30a of the shutter 30 is accommodated in undercuts 34 defined by the occlusal tie wings 18. The end 30 a of the shutter 30 accommodated by the undercuts 34 generally resembles an open "D" and is configured to remain in the undercuts 34 throughout movement of the shutter between the open and closed positions. As the shutter 30 moves between the open and closed positions, the end 30a of the shutter translates within the undercuts 34. An aperture 30b is formed in the shutter 30 to accommodate a tool to facilitate opening of the shutter.

The shutter 30 curves labially and gingivally around the occlusal tie wings 18 and then curves lingually towards the archwire slot 20. When the shutter 30 is in the closed position and the archwire applies a labially directed force to the shutter 30, the gingival end 36 of the shutter 30 contacts the deflection surfaces 24 to inhibit the shutter from being accidentally removed from the archwire slot 20. At the same time, the lingual surface 38 of the shutter 30 contacts the archwire 22 to urge it continuously into the archwire slot 20. When the shutter 30 is pivoted and translated to remove it from the archwire slot 20, the gingival end 36 can be accommodated by the resting grooves 26 to hold the shutter in the open position although this is not necessary as shown by the dotted line in FIG. 2b. The is due to the fact that as the compressed shutter 30 is opened, it flexes over the occlusal tie wings 18 as the shutter pivots and translates in the occlusal undercuts 34 to maintain the shutter open. The shutter 30 can be closed using a finger by simply pushing on the shutter until the gingival end 36 of the shutter enters the archwire slot 20 with the lingual surface 38 in contact with the archwire 22. The shutter 30 can be opened by inserting a one or two prong ligature director into the aperture 30b and applying an occlusally directed force on the shutter in the interwing region 12' of the body 12.

Figure 3A:
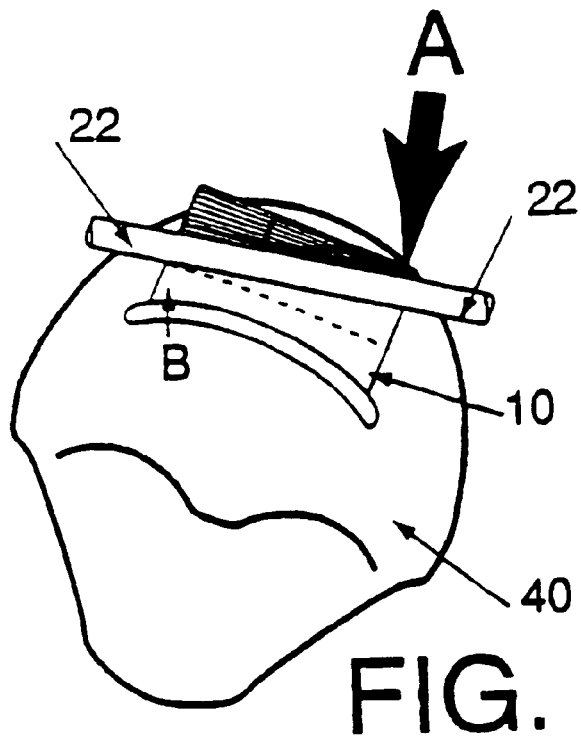
FIGS. 3a and 3b are occlusal views of an incisor section to which the orthodontic bracket of FIG. 1 of the present invention is attached, showing low deflection moment during movement of the tooth.
Figure 3B:
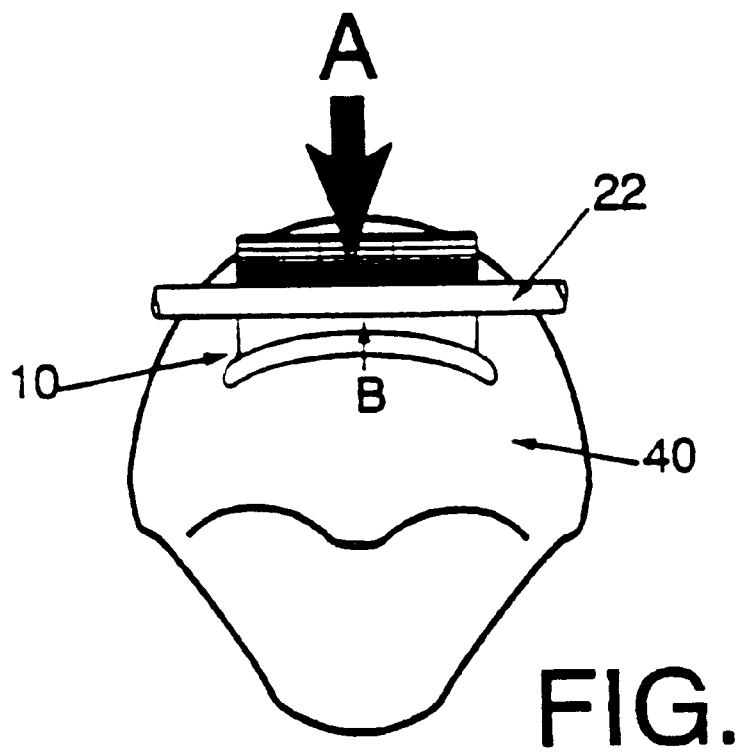

The design of the shutter 30 is such that a rectangular archwire 22 is seated to apply torque to the archwire slot 20 depending on the rectangular cross-sectional shape of the archwire 22. The continuous active seating or biasing of the archwire 22 by the shutter 30 provides for accurate tooth movement. Referring now to FIGS. 3a and 3b, a tooth 40 with an orthodontic bracket 10 on it is shown. In FIG. 3a the tooth 40 is shown in an original "rotated" position while in FIG. 3b, the tooth is shown in a final "straight" position. The designations A and B in FIGS. 3a and 3b denote coupled sets of force vectors applied by the shutter 30 on the orthodontic bracket 10 and archwire. As can be seen, the archwire 22 in FIG. 3a deflects the shutter 30 labially on the right side reducing the initial force and moment applied to tooth 40 until the shutter gradually seats itself into the archwire slot 20 as shown in FIG. 3b with less patient discomfort.

Figure 4:
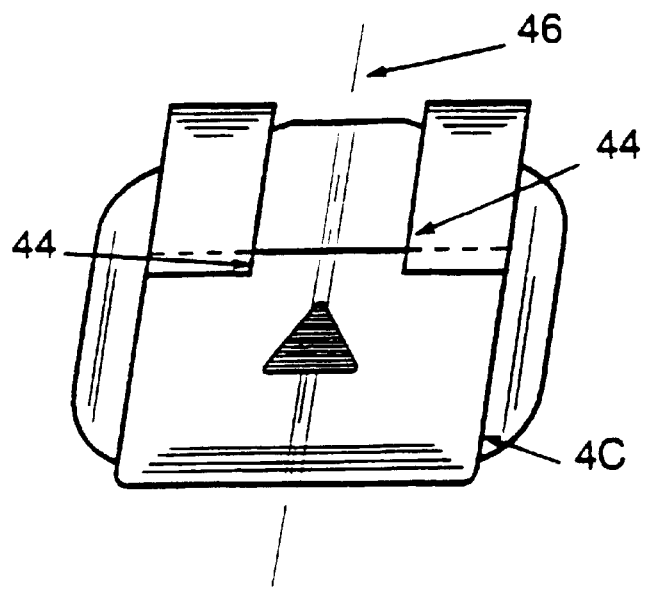
FIG. 4 is a front elevational view of an orthodontic bracket of the type shown in FIG. 1 positioned on a tooth.

Referring now to FIG. 4, an orthodontic bracket 10 is shown on a tooth 40. The occlusal edges of the orthodontic bracket 10 are preferably parallel to the incisal edges and parallel to the archwire slot. Two scribe lines 44 on the orthodontic bracket 10 delineate the long axis 46 of the tooth 40 for ideal placement of the orthodontic bracket. Also, the external lingual surface of the mounting pad 14 is angulated or biased to assist alignment and placement of the orthodontic bracket 10 against the long axis of the tooth. Larger brackets may be used for larger molars.

Figure 5:
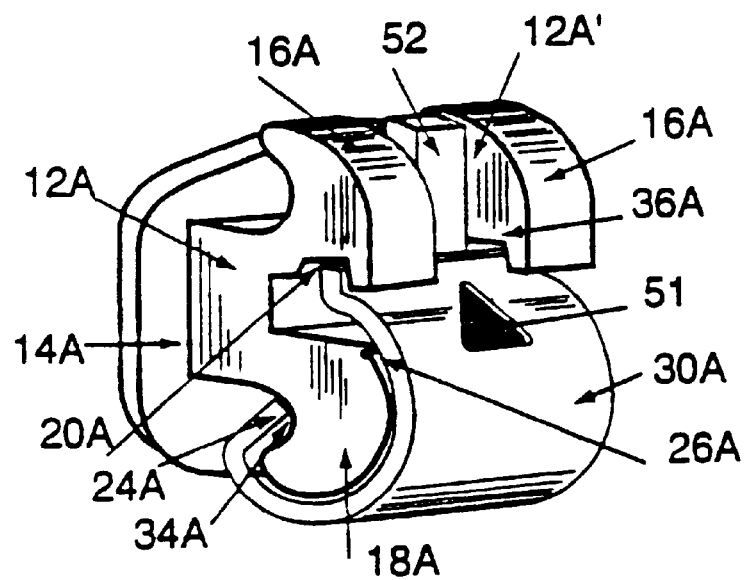
FIG. 5 is a perspective view of an alternative embodiment of a pre-engaging twin orthodontic bracket in accordance with the present invention.
Figure 6:
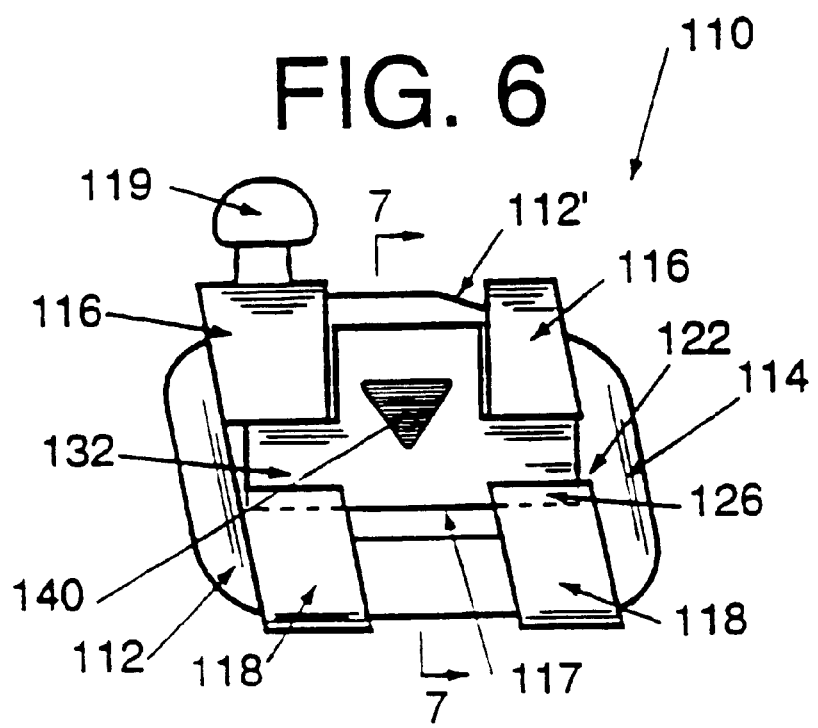
FIG. 6 is a front elevational view of yet another alternative embodiment of a pre-engaging twin orthodontic bracket in accordance with the present invention.

Referring now to FIG. 5, an alternative embodiment of an orthodontic bracket is shown and is generally indicated to by reference numeral 10a. In this embodiment, like reference numerals will be used to indicate like components of the first embodiment with an "a" added for clarity. As can be seen, the shutter 24a is received in undercuts 34a defined by the occlusal tie wings 18a. The shutter 30a has an aperture 51 formed in it to receive a tool and facilitate pivoting of the shutter from the closed to open positions using a tool. A hollow vertical slot 52 is provided on the body 12a in the interwing region 12a'. The hollow slot 52 allows the orthodontic bracket 10a to provide for more tooth inclination, torque control and overcorrection than prior art orthodontic brackets.

Referring now to FIGS. 6 to 10, yet another embodiment of a pre-engaging twin orthodontic bracket is shown and is generally indicated to by reference numeral 110. As can be seen, orthodontic bracket 110 includes a body 112 and a lingual mounting pad 114 attached to the body. The mounting pad 114 has a lingual surface to be attached to a tooth. A pair of laterally spaced gingival tie wings 116 and a pair of laterally spaced occlusal tie wings 118 extend from a labial surface of the body 112. The gingival tie wings 116 and the occlusal tie wings 118 curve lingually. A horizontal crossbar 117 extends across the interwing region 112' of the body 112 and interconnects the occlusal tie wings 118. A ball hook 119 extends from one of the gingival tie wings 116.

The gingival surface 115 of the body in the interwing region 112' between the gingival tie wings 116 is convex and is generally semi-elliptical. The labial surface of the body in the interwing region 112 has a notch 150 formed in it. The gingival tie wings 116 are bevelled as indicated by reference numeral 121. An archwire slot 120 extends mesiodistally across the body 112 and between the gingival and occlusal tie wings located at opposed mesial and distal sides of the body and opens labially to receive an archwire 122. The occlusal wall of the archwire slot 120 is continuous and is constituted by the occlusal tie wings 118 and the crossbar 117. The occlusal wall of the archwire slot 120 has a notch formed in it to define two deflection surfaces 124 and 126 respectively. Deflection surface 124 is constituted by a labial bevel while deflection surface 126 is constituted by a lingual bevel.

Figure 7:
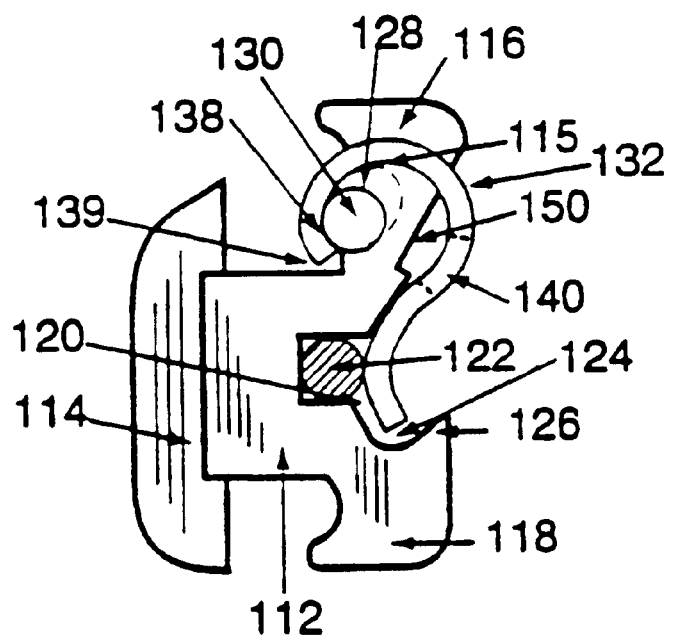
FIG. 7 is a cross-sectional view of FIG. 6 taken along line 7—7.
Figure 8:
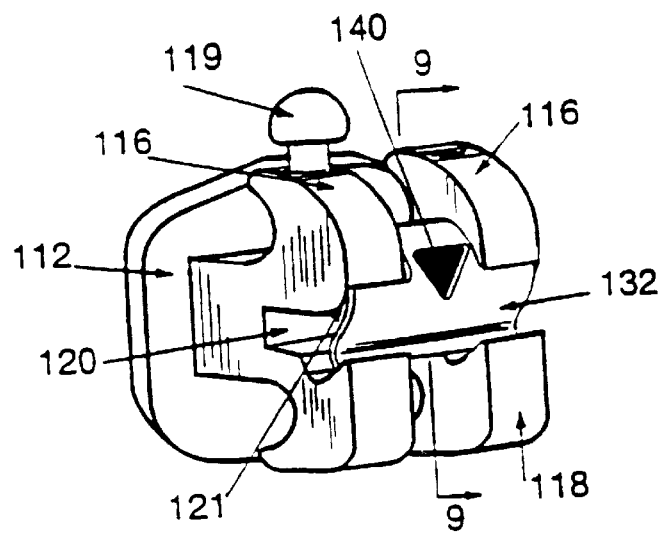
FIG. 8 is a three-quarter perspective view of the orthodontic bracket of FIG. 6.
Figure 10:
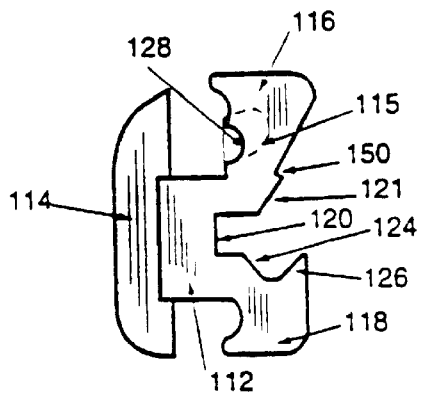
FIG. 10 is an enlarged cross-sectional view of a portion of the orthodontic bracket of FIG. 8 with the pivot pin omitted.

Looking at FIGS. 7 and 10, it can be seen that a curved groove 128 is formed in the gingival tie wings 116 and interwing region 112' of the body and extends mesiodistally. The groove 128 is spaced above the gingival surface of the body 112 and accommodates a pivot pin 130. The pivot pin 130 is bonded to the gingival tie wings 116 by suitable means such as brazing, soldering, welding or the like. A shutter 132 resembling an inverted "T" in front elevation is pivotally mounted on the pivot pin 130 in the interwing region 112' and is movable between a closed position where access to the archwire slot 120 is inhibited and an open position where access to the archwire slot 120 is permitted.

Figure 11A:
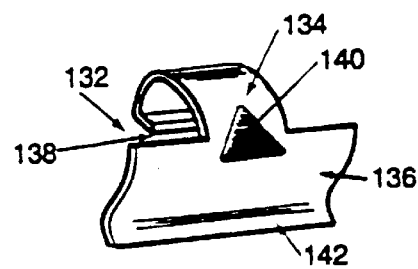
FIG. 11a and 11b are perspective and front elevational views respectively of a shutter forming part of the orthodontic bracket of FIG. 6.
Figure 11B:
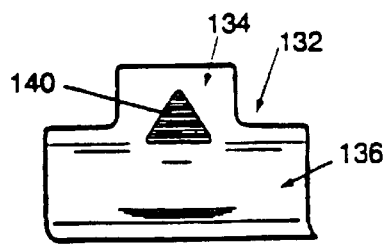

Referring now to FIGS. 11a and 11b, the shutter 132 is better illustrated. As can be seen, the shutter 132 includes a lingually curved upright stem 134 and a transverse arm 136 at the occlusal end of the stem. The edges of the shutter are curved at the intersection between the stem 134 and transverse arm 136 to strengthen the shutter. The stem 134 curves over itself at its gingival end and terminates in an open D-shaped cup 138 which partially surrounds the pivot pin 130 and is accommodated in an undercut 39 formed in the interwing region 112' occlusally of the pivot pin to secure the shutter to the orthodontic bracket 110. A generally triangular aperture 140 is formed in the stem 134 to receive a tool to facilitate pivoting of the shutter 132 from the closed position to the open position. The occlusal portion of the transverse arm 136 of the shutter is generally convex when viewed in profile and is dimensioned to be accommodated in the archwire slot 120. The occlusal edge 142 of the transverse arm 136 is slightly concave.

The archwire slot 120 is designed to accommodate circular cross-section or rectangular cross-section archwires 122. When the archwire 122 is positioned in the archwire slot and the shutter is closed, the lingual surface of the shutter 132 contacts the archwire to urge it continuously against the body 112 (see FIG. 9a). The deflection surface 126 inhibits the shutter 132 from being accidentally removed from the archwire slot 120 when the archwire 122 applies a labially directed force to the archwire. When it is desired to open the shutter 132, a tool is inserted into the aperture 140 and is accommodated by the notch 150. The tool can be used to pivot the shutter with sufficient force so that the occlusal edge 142 of the transverse arm 136 passes over the deflection surface 126 and so that the end of the cup 138 rotates into the undercut 139 allowing the shutter 132 to open.

Figure 9A:
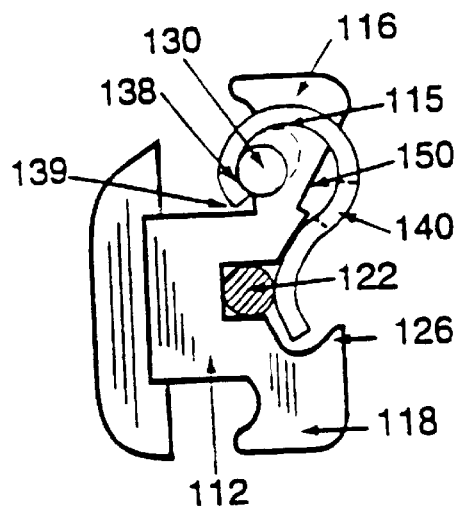
FIG. 9a and 9b are cross-sectional views of FIG. 8 taken along line 9—9 with the shutter in closed and open positions respectively.
Figure 9B:
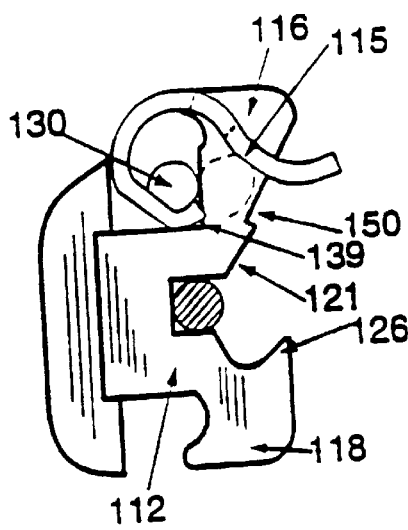

During the pivotal movement of the shutter 132, the convex interwing gingival surface 115 of the body 112 and the flexing of the initially compressed shutter over the convex surface 115 as the shutter 132 pivots around the pivot pin 130 with the end of the shutter in the notch as shown in FIG. 9b, maintains the shutter in an open condition. The undercut 139 occlusally of the pivot pin 130 provides sufficient clearance for the shutter 132 to pivot freely in a rotary fashion.

Although the shutter 132 has been described as having a D-shaped cup 138 to surround the pivot pin 130, the shutter can curl back around itself to surround substantially the pivot pin 130 between the gingival tie wings. Also, although the pivot pin has been described as being accommodated in curved slots and bonded to the orthodontic bracket, it should be apparent to those of skill in the art that the pivot pin may be integrally formed with and extend between the gingival tie wings.

Although the gingival surface of the body in the interwing region has been described as being semi-elliptical, it should be appreciated that other surface configurations are suitable. Also, although the pivot pin has been described as being accommodated in a groove extending across the gingival tie wings and the body, the pivot pin may only extend between the gingival tie wings in the interwing region 112' making the gingival tie wings more accessible. Also, although the shutter has been shown as pivoting about a pivot pin extending between the gingival tie wings, the pivot pin may extend between the occlusal tie wings.

Referring now to FIGS. 12 to 15, yet another embodiment of an orthodontic bracket is shown and is generally indicated to by reference numeral 220. As can be seen, orthodontic bracket 220 includes a body 222 and a locking shutter 224. For illustrative purposes, the orthodontic bracket 220 is configured for a maxillary tooth but it can be appreciated that the orthodontic bracket 220 could be used on a mandibular tooth.

Body 222 includes a lingual mounting pad 226 having a lingual tooth attaching surface 228 adapted to direct attachment to a tooth or to a pad that may be attached to a tooth. A pair of laterally spaced occlusal tie wings 234 and a pair of laterally spaced gingival tie wings 236 project from a labial surface of the body 222. Each tie wing 234, 236 curves lingually to define an undercut 238 for receiving a ligature. An archwire slot 240 extends mesiodistally across the body 222 and between the occlusal and gingival tie wings at opposed mesial and distal sides of the body. The archwire slot 240 accommodates an archwire 242. The archwire slot 240 has a pair of opposed surfaces 244, 246 at its mesial and distal ends. Inverted V shaped deflection notches 248 are provided in the gingival tie wings 236 above the archwire slot. The deflection notches 248 are provided to receive a gingival edge 250 of the locking shutter 224 in the closed position.

Figure 12:
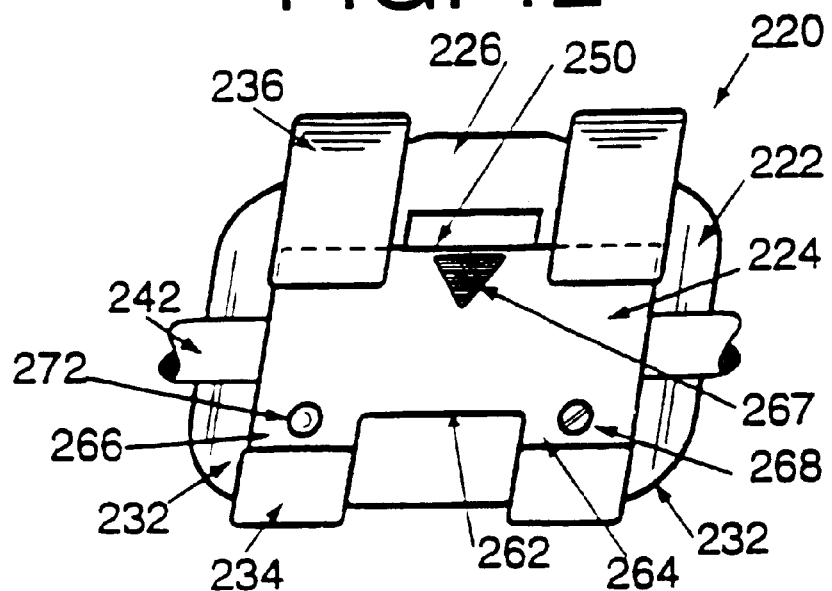
FIG. 12 is a front elevational view of an alternative embodiment of an orthodontic bracket in accordance with the present invention having a sliding shutter.
Figure 13:
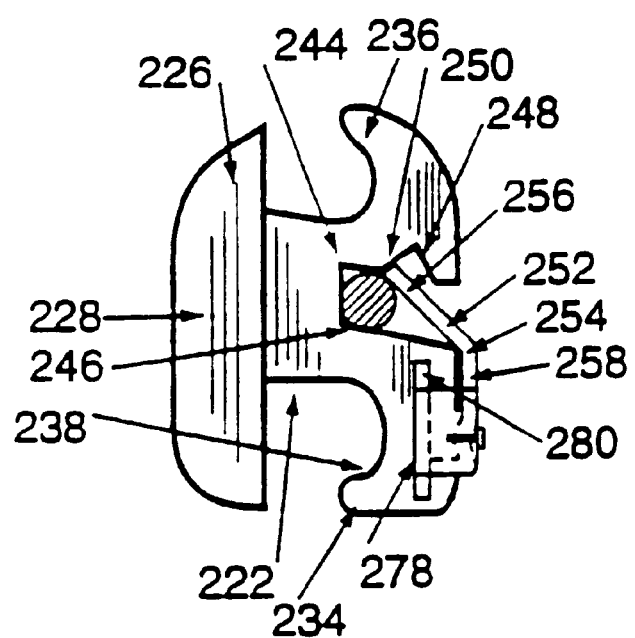
FIG. 13 is a side elevational view of the orthodontic bracket of FIG. 12.
Figure 14:
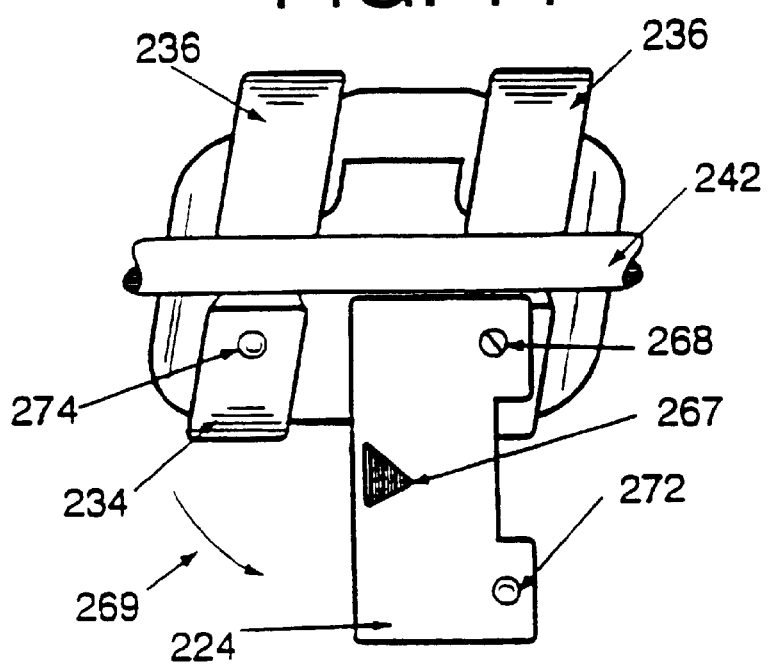
FIG. 14 is a view similar to FIG. 12 of the orthodontic bracket showing movement of the shutter to an open position.
Figure 15:
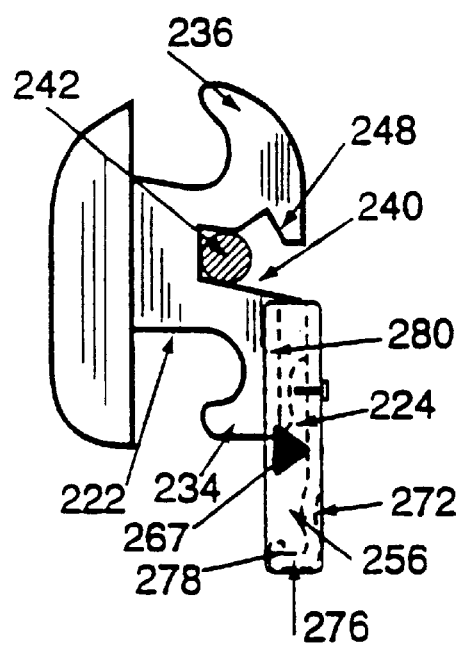
FIG. 15 is a side elevational view of the orthodontic bracket of FIG. 14 with the shutter in the open position.

The locking shutter 224 extends between the occlusal and gingival tie wings at opposed mesial and distal sides of the body 222 and across the archwire slot 240. The locking shutter 224 has a body 252 which is cranked as indicated at 254 to provide a pair of relatively inclined portions 256, 258. Occlusal edge 260 of the shutter body 252 is provided with a recess 262 (as seen in FIGS. 12 and 14) so as to define a pair of downwardly projecting arms 264, 266 that overlie respective ones of the occlusal tie wings 234 when the shutter 224 is in a closed position. An aperture 267 is centrally positioned on the shutter 224 to accommodate a tool to facilitate movement of the locking shutter.

The locking shutter 224 is retained on the orthodontic bracket 220 by means of an off-center pivot pin 268 that passes through an aperture (not shown) formed in the arm 264 and is secured to the occlusal tie wing 234. The shutter 224 is thus able to slide in a generally occlusal-gingival plane about the pin 268 as indicated by arrow 269 in FIG. 14.

An indentation 272 is formed in the arm 266 and a corresponding dimple 274 formed in the underlying occlusal tie wing 234. Arm 266 includes a buccally-extending return 276 that passes around the distal side of the occlusal tie wing 234 and has a retaining plate 278 that is received within a slot 280 formed in the side of the occlusal tie wing 234.

The indentation 272 cooperates with the dimple 274 to form a detent which inhibits pivotal movement of the shutter 224 about the pivot pin 268 and retains the locking shutter 224 in the closed position. The retaining plate 278 cooperates with the slot 280 and the shutter cooperates with the deflection notches 248 to inhibit labial movement of the locking shutter when in the closed position and an archwire applies a labially directed force to the shutter so that the locking shutter 224 retains the archwire 242 within the archwire slot 240.

To open the locking shutter 224, it is simply necessary to overcome the detent provided by the indentation 272 and dimple 274 and rotate the locking shutter 224 about the pivot pin 268. Access to the archwire slot 240 is thus obtained. Similarly, to close the locking shutter 224, it is simply necessary to pivot the locking shutter about the pivot pin 268 so that the gingival edge 250 engages the deflection notches 248 and the indention 272 engages the dimple 274. The locking shutter 224 is thus held securely and cooperates with the archwire 242 to apply the requisite forces to the archwire within the archwire slot.

An alternative embodiment of an orthodontic bracket is shown in FIGS. 16a to 17b and is generally indicated to by reference numeral 220a. In this embodiment, like components of the previous embodiment will be identified with like reference numerals, with the suffix "a" added for clarity.

As can be seen, the locking shutter 224a is pivotally secured to a boss 290 that extends between the gingival tie wings 236a by way of centrally positioned pivot pin 268a. One edge 292 of the locking shutter 224a is arcuate giving the shutter 224a a generally semi-circular appearance. Deflection notches 248a are formed in the occlusal tie wings 234a adjacent the archwire slot 240a. It will be noted that the labial surfaces of the occlusal tie wings 234a are labially protrusive so that the arcuate edge 292 of the locking shutter 224a is aligned with the deflection notches 248a.

Figure 16A:
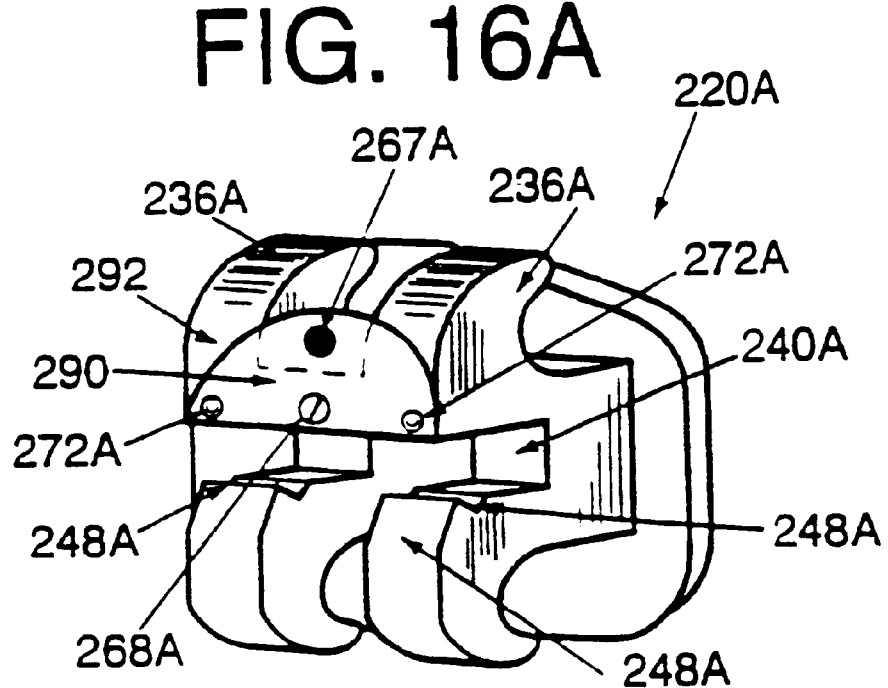
FIG. 16a is a perspective view of another alternative embodiment of an orthodontic bracket in accordance with the present invention having a sliding shutter shown in an open position.
Figure 16B:
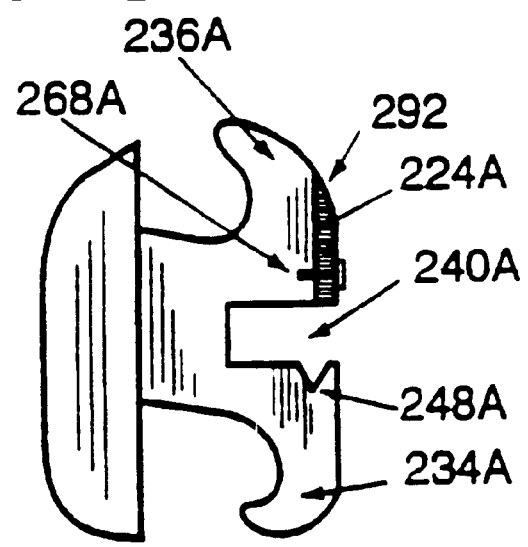
FIG. 16b is a side elevational view of the orthodontic bracket shown in FIG. 16b.
Figure 17A:
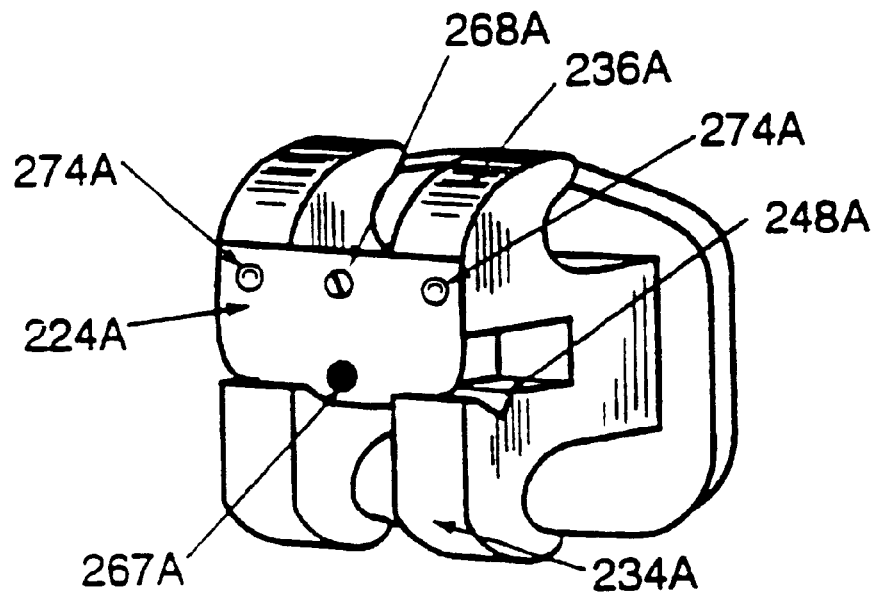
FIG. 17a is a perspective view of the orthodontic bracket of FIG. 16a showing the shutter in a closed position.
Figure 17B:
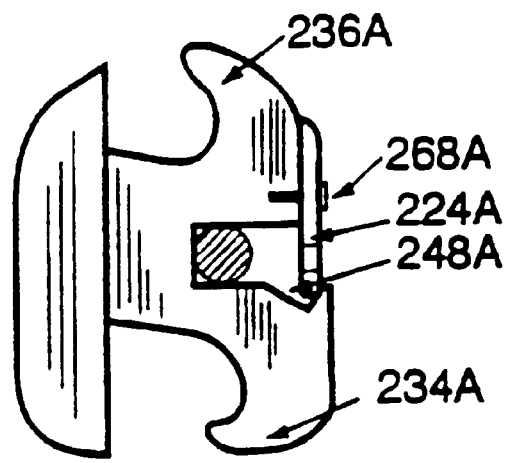

Dimples (not shown) are formed on each of the gingival tie wings 236a and corresponding indentations 272a are formed on the locking shutter 224a. The dimples and indentations 272a cooperate when the locking shutter 224a is either in the open or closed positions to retain the locking shutter in that position. An aperture 267a if provided in the shutter to receive a tool and facilitate movement of the shutter 224a. The locking shutter 224a can be pivoted about pivot pin 268a so as to bring the arcuate edge 292 into engagement with the notches 248a as shown in FIGS. 17a and 17b by overcoming the detent provided by the indentations 272a and dimples. In this position, the locking shutter 224a is effective to inhibit removal of an archwire from the archwire slot 240a. The locking shutter 224a can be readily moved to the open position by rotating the locking shutter about the pivot pin 268a to allow access to the archwire slot 240a as shown in FIG. 16a.

Figure 18:
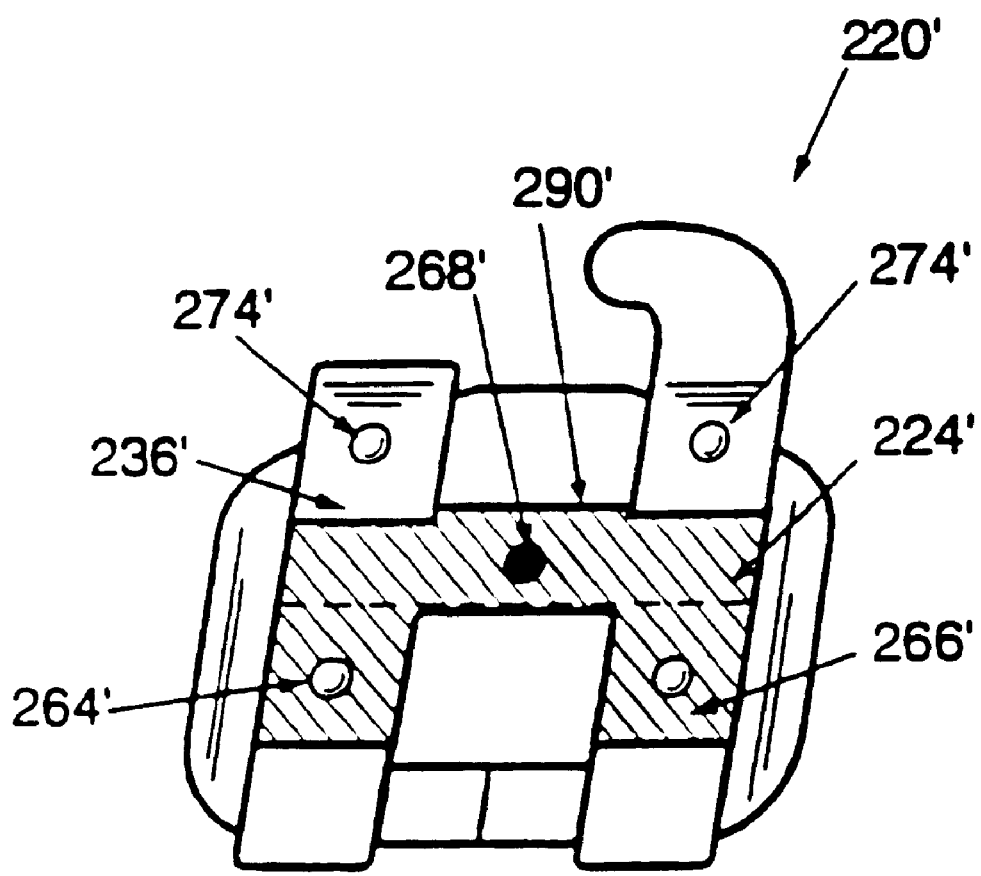
FIG. 18 is a front elevational view of an alternative embodiment of an orthodontic bracket in accordance with the present invention.
Figure 19:
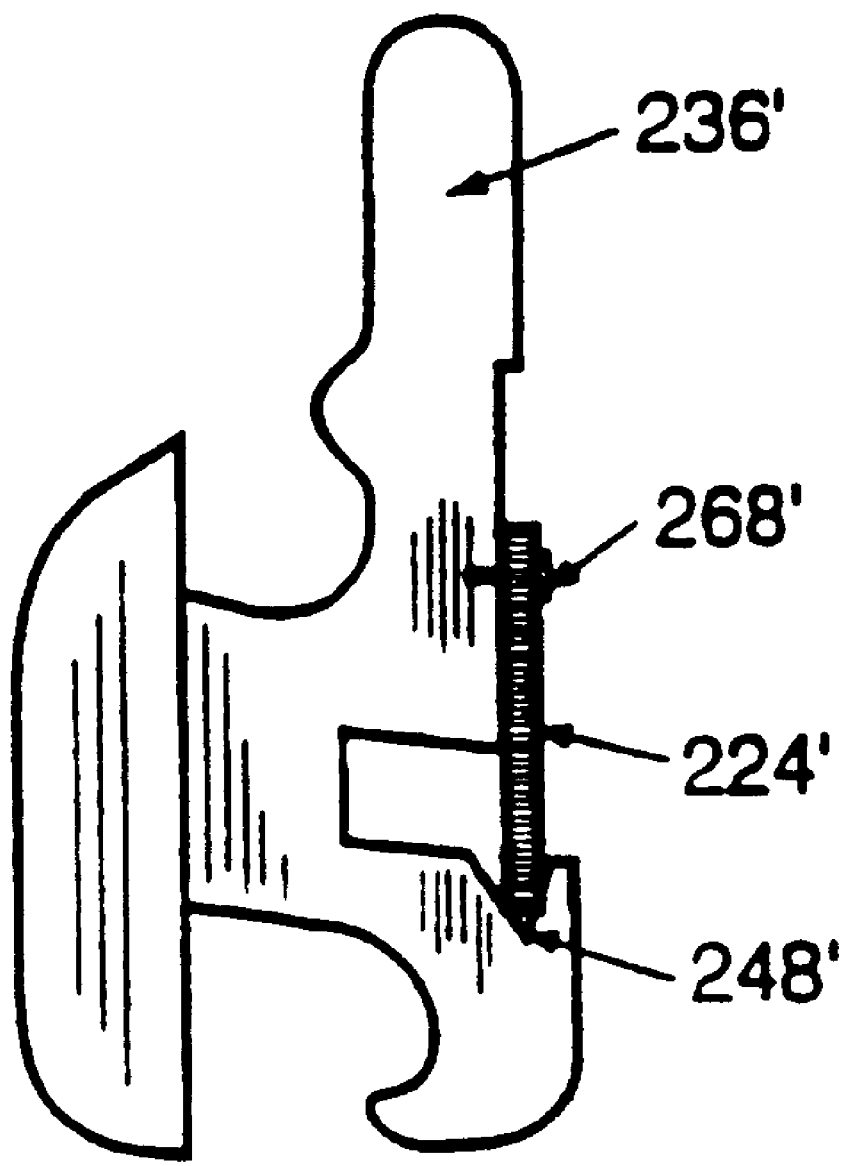
FIG. 19 is a side elevational view of the orthodontic bracket of FIG. 18.
Figure 20:
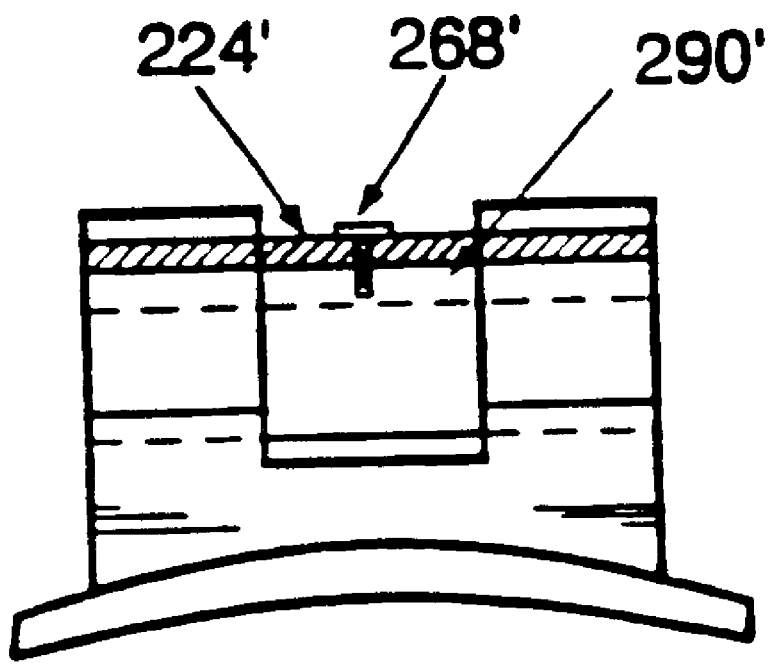
FIG. 20 is a top plan view of the orthodontic bracket of FIG. 18.
Figure 21:
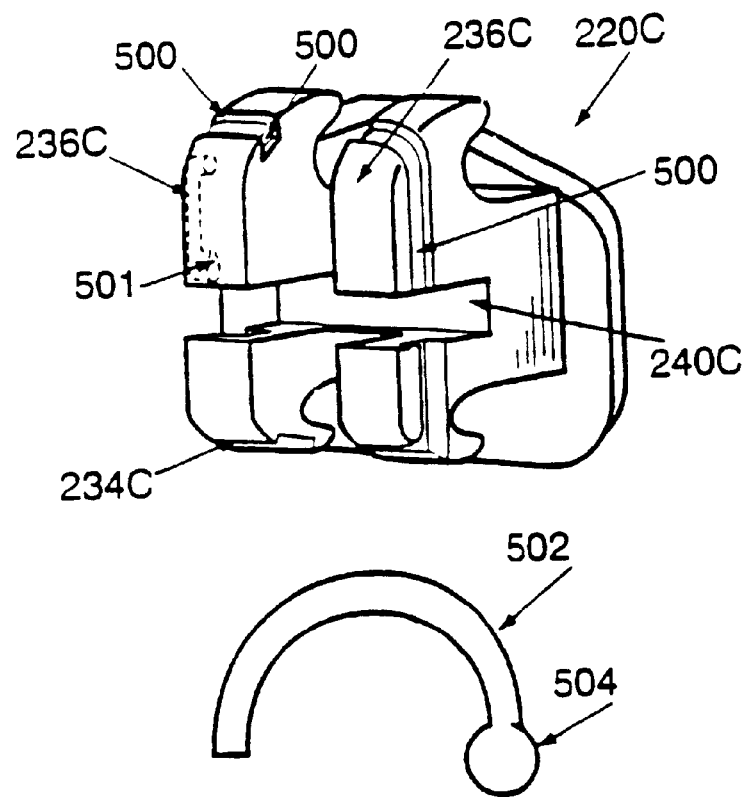
FIG. 21 is a partially exploded three-quarter perspective view of a still yet another embodiment of an orthodontic bracket in accordance with the present invention.

Another alternative arrangement of an orthodontic bracket 220' is shown in FIGS. 18 to 20. In this embodiment, like reference numerals will be used to indicate like components of the embodiment of FIGS. 12 to 15 with the suffix "'" added for clarity. In this embodiment, the locking shutter 224' is relieved and is generally C-shaped to provide a pair of arms 264' and 266'. Similar to the previous embodiment, the locking shutter 224' is pivotally secured to a boss 290' extending between the gingival tie wings 236' by way of pivot pin 268'. A dimple 274' is provided on both gingival tie wings 236'. Indentations 272' on the arms 264' and 266' co-operate with the dimples 274' with the detent formed between the indentations and dimples maintaining the locking shutter 224' in the open position. The notches 248' define deflection surfaces to inhibit labial movement of the shutter 224' and its removal from the archwire slot 240' when the shutter 224' is in the closed position and an archwire applies a labially directed force to the shutter. In order to move the shutter from the open to closed position, it is necessary to overcome the detent provided by the indentations 272' and the dimples 274' and pivot the shutter 224' about the pivot pin 268'.

In embodiments of the orthodontic brackets illustrated in FIGS. 12 to 20, it will be observed that movement of the locking shutter between open and closed positions is obtained by simple rotation of the locking shutter about the pivot pin so that the locking shutter remains captive to the body but at the same time is securely held in the closed and/or open positions by the action of the detent formed between and indentations and dimples.

A further embodiment of an orthodontic bracket is shown in FIGS. 21 to 24, in which like reference numerals will be used to denote like components of the embodiment of FIGS. 12 to 15 with suffix 'c' added for clarity. As can be seen, a circular track 500 is formed on the mesial, distal, occlusal and gingival sides of the orthodontic bracket 220c. The circular track 500 passes through the occlusal and gingival tie wings 234c and 236c respectively to intersect the archwire slot 240c. Bores 501 are formed in the circular tracks 500 in the mesial and distal sides of the gingival tie wings 236c slightly above the archwire slot 240c. The archwire slot 240c is offset occlusally so that the gingival tie wings 236c are longer than the occlusal tie wings 234c.

The track 500 receives a shutter in the form of a part circular clip 502 having a circular protrusion 504 at one end. The clip 502 is slidable in the track 500 but provides a friction grip against the track to inhibit unintentional movement. The circular protrusion 504 is accommodated by one of the bores 501 to hold the clip 502 in either the closed or open positions.

Figure 22:
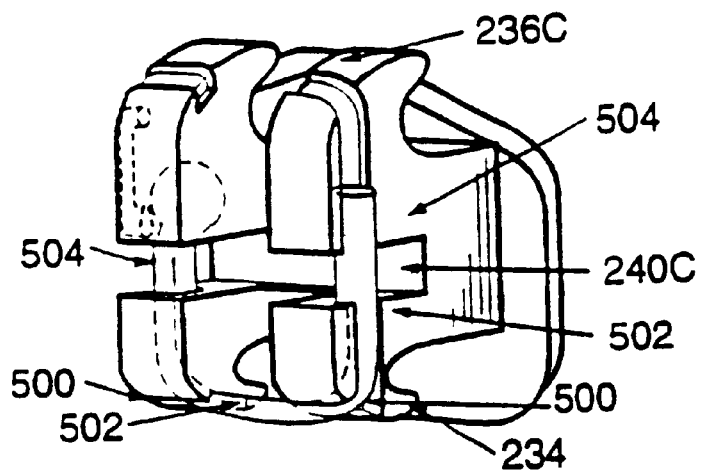
FIG. 22 is a three-quarter perspective view similar to FIG. 21 of the orthodontic bracket in a closed position.
Figure 23:
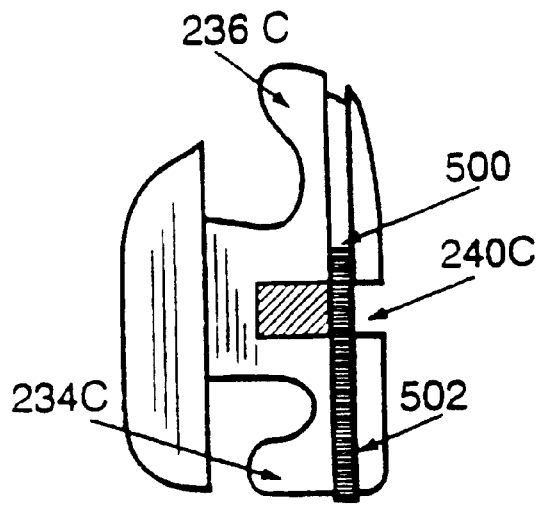
FIG. 23 is a side elevational view of the orthodontic bracket of FIG. 22 accommodating an archwire.
Figure 24:
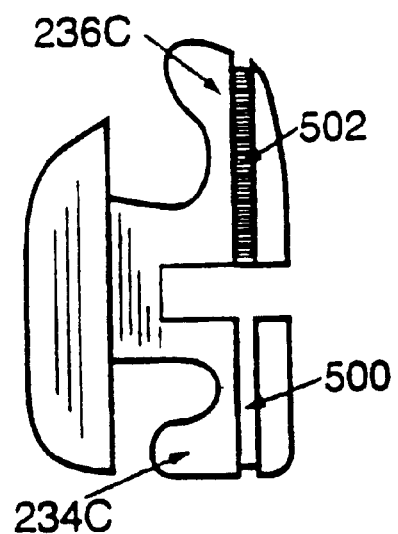
FIG. 24 is a side elevational view of the orthodontic bracket of FIG. 22 in an open position.
Figure 28:
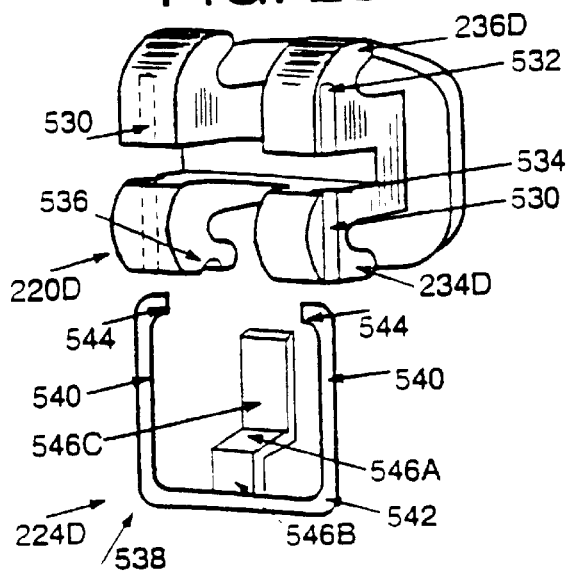
FIG. 28 is an exploded three-quarter perspective view of yet another alternative embodiment of an orthodontic bracket in accordance with the present invention.
Figure 29:
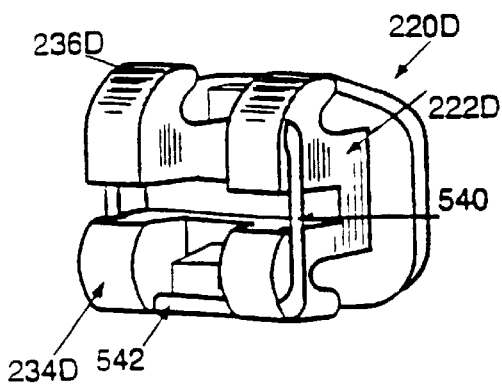
FIG. 29 is a three-quarter perspective view of the orthodontic bracket of FIG. 28 in a closed position.

The clip 502 may be rotated in the track 500 between an open position in which access to the archwire slot 240c is available (see FIG. 24) and a closed position in which access is inhibited (see FIGS. 22 and 23). As can best be seen in FIG. 22, the offset of the archwire slot 240c allows the clip 502 to overlie the archwire slot 240c to retain an archwire within the archwire slot. Rotation of the clip 502 through approximately 180 degrees moves the clip to the position shown in FIG. 24 at which the archwire slot 240c is open and access to the archwire is provided. The circular protrusion 504 facilitates rotation of the clip 502 between open and closed positions, with the friction between the clip and the track 500 and the cooperating protrusion 504 and bore 501 retaining the clip 502 in the desired position.

A still further embodiment of an orthodontic bracket 220b is shown in FIGS. 25 to 27 in which like reference numerals will be used to denote like components of the embodiment of FIGS. 12 to 15, with a suffix "b" added for clarity. As can be seen, the shutter 224b is slidable within a slot 510 formed in each of the occlusal wings 234b. A U-shaped strap 512 is secured to the labial face of shutter 224b and extends through a guide slot 514 and a washer 515 in the base of each of the slots 510. A coil spring 516 is positioned in each slot beneath the shutter 224b and surrounds each arm 512a of the strap 512. The arms 512a are cranked slightly above the coil springs 516 toward the archwire slot 240b as indicated to by reference numeral 518. The springs 516 bias the shutter 224b to a closed position in which the gingival edge 250b of the shutter 224b engages the notches 248b.

The labial surface of the shutter 224b carries a wedge 520 that cooperates with a complementary recess 522 formed in the slots. The wedge 520 retains the shutter 224b in the open position and may be released by application of a force to the bight 512b of the strap 512 to release the shutter 224b under the action of the springs 516. The shutter 224b is thus retained in the closed position to resist labial movement of an archwire 242b in the archwire slot 240b. The spring loaded shutter 224b may also be applied in a similar manner to two single orthodontic brackets or a 3 wing orthodontic bracket.

A still further embodiment of an orthodontic bracket 220d is shown in FIGS. 28 to 31 where like reference numerals will be used to indicate like components of the embodiment illustrated in FIGS. 12 to 15 with the suffix "d" added for clarity. In this embodiment, grooves 530 are formed in the mesial and distal sides of the body 222d. Each groove 530 extends through the gingival and occlusal tie wings 236d and 234d. The grooves 530 terminate in blind bores 532 in the gingival tie wings 236d. Blind bores 534 are also formed in the grooves 530 in the occlusal tie wings 236d adjacent the archwire slot 240d (see FIG. 31). The occlusal surfaces of the occlusal tie wings 236d are undercut to provide a lateral groove 536 that extends mesiodistally between the occlusal tie wings.

A shutter 224d in the form of a generally U-shaped clip 538 is formed with a pair of outer arms 540 interconnected by a lateral bight 542. The ends of the arms 540 are formed with inwardly-directed projections 544 for receipt within the bores 532 or 534. A support arm 546 is secured to the lateral bight 542 and is jogged to provide a horizontal arm 546a between a pair of vertical arms 546b and 546c respectively. One of the vertical arms 546c is received within a vertical slot 548 in the body 220d and maintains alignment of the clip 538 as it is moved between the open and closed positions. The slot 548 is located in the interwing region of the body 222d to provide uniform support.

Figure 30A:
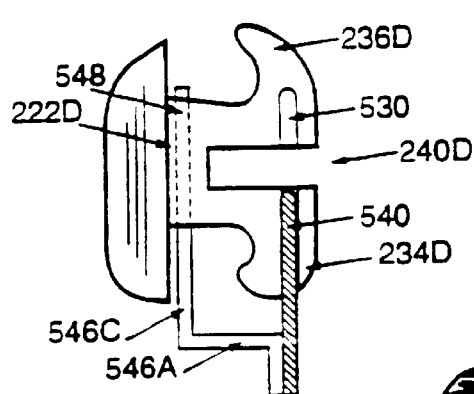
FIG. 30a is a side elevational view of the orthodontic bracket of FIG. 29 in an open position.
Figure 30B:
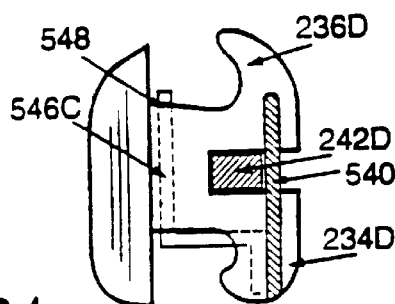
FIG. 30b is a side elevation view of the orthodontic bracket of FIG. 29 in a closed position.
Figure 31:
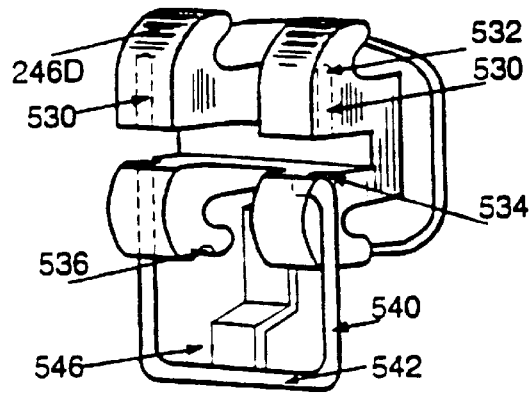
FIG. 31 is a three-quarter perspective view of the orthodontic bracket of FIG. 29 in the open position.

The clip 538 is assembled on the orthodontic bracket 220d so that the arms 540 are received within the respective grooves 530. The projections 544 are received within the blind bores 534 so that the archwire slot 240d is open for receipt of an archwire as shown in FIG. 30a. With the archwire 242d inserted into the archwire slot 240a as shown in FIG. 30b, the clip 538 may be advanced along the grooves 530 until the projections 544 are received within the blind bores 532. In this position, the lateral bight 542 is received within the lateral groove 536 to provide further security for the clip 538. The vertical arm 546c and slot 548 serve to guide and align the clip 538 during sliding motion to facilitate the relative movement between the clip and the orthodontic bracket 220d.

A further embodiment of an orthodontic bracket 220e is shown in FIGS. 32 to 36. In this embodiment like reference numerals will be used to denote like components of the embodiment of FIGS. 12 to 15 with a suffix "e" added for clarity. In the embodiment of FIGS. 32 to 36, grooves 560 are formed in the occlusal tie wings 234e only. The shutter 224e included side flanges 562 that have inwardly directed protrusions 564 to engage the grooves 560. The shutter 224e has a pair of lingually angulated occlusal arms 264e and 266e and a centrally positioned gingival arm 566 defined partly by a pair of slits 568 in the shutter 224e (best seen in FIG. 36). The gingival arm 566 is recurved in a labial direction as indicated by reference numeral 569 and is resilient to engage the labial notches 248e at the mesial and distal ends of the archwire slot 240e and inhibit labial movement of shutter 224e when an archwire applies a labially directed force to the shutter. Protrusions 570 are provided on the sides of the shutter 224e to form a handle and facilitate sliding movement of the shutter 224e between the open and closed positions. Again therefore, a sliding shutter is provided on the orthodontic bracket 220e to retain an archwire in the archwire slot 240e.

Figure 37:
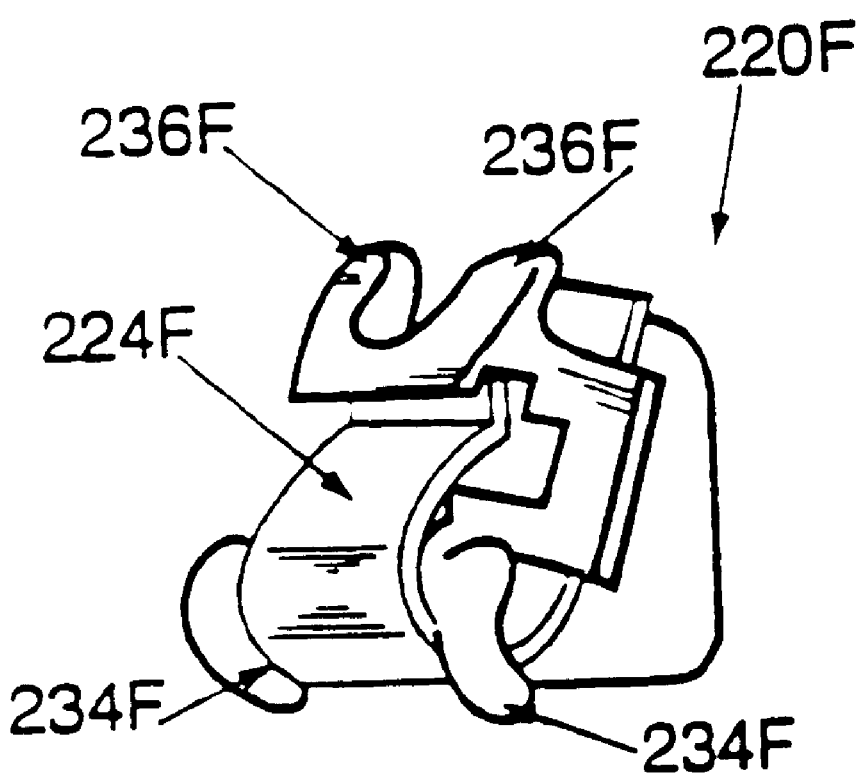
FIG. 37 is a three-quarter perspective view of still yet a further embodiment of an orthodontic bracket in accordance with the present invention.
Figure 38:
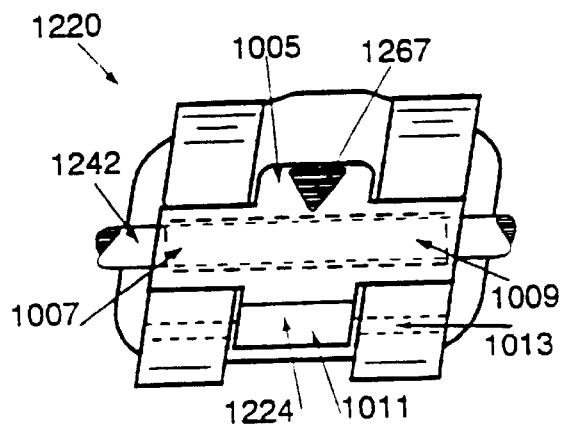
FIG. 38 is a front elevational view of yet another alternative embodiment of an orthodontic bracket in accordance with the present invention in a closed position.
Figure 40:
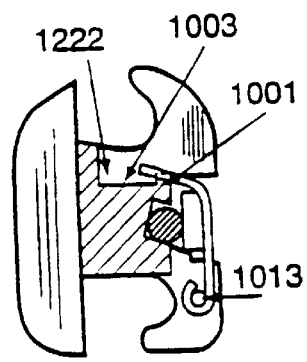
FIG. 40 is a side elevational view of the orthodontic bracket of FIG. 38 accommodating a round archwire.
Figure 39:
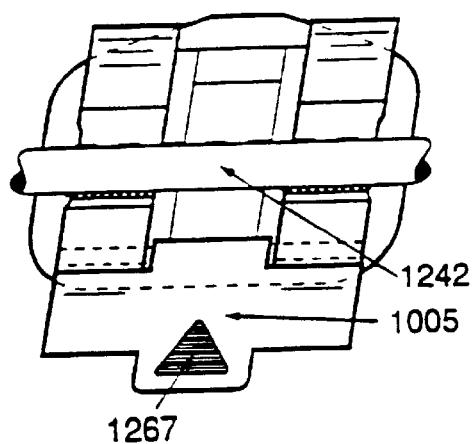
FIG. 39 is a front elevational view of the orthodontic bracket of FIG. 38 in an open position.
Figure 41:
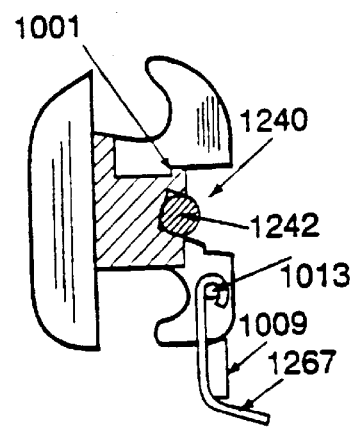
FIG. 41 is a side elevational view of the orthodontic bracket of FIG. 39 accommodating a round archwire.
Figure 42:
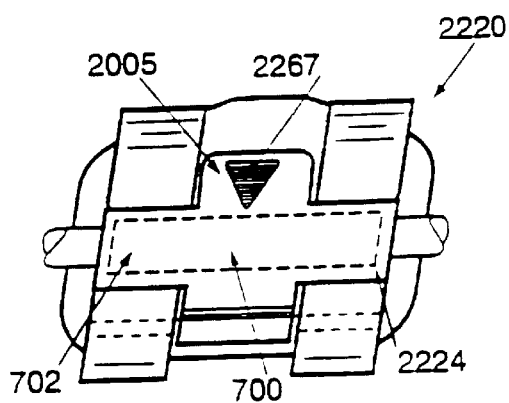
FIG. 42 is a front elevational view of yet another alternative embodiment of an orthodontic bracket in accordance with the present invention in a closed position.
Figure 44:
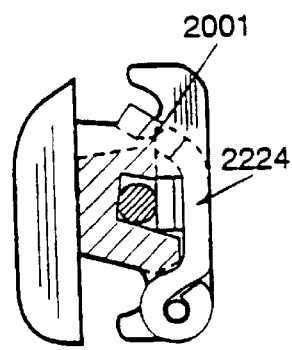
FIG. 44 is a side elevational view of the orthodontic bracket of FIG. 42 accommodating a round archwire.
Figure 43:
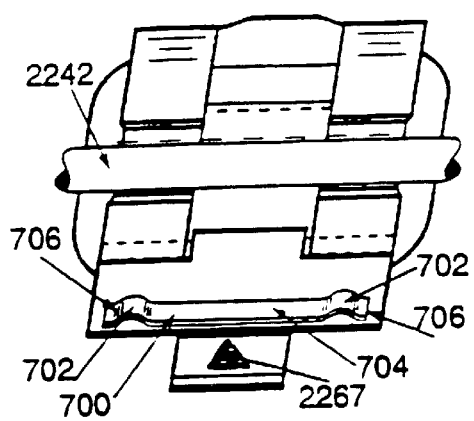
FIG. 43 is a front elevational view of the orthodontic bracket of FIG. 42 in an open position.

In a further embodiment shown in FIG. 37, a known orthodontic bracket 220f sold under the trade name "SPEED" is shown and included a pair of occlusal tie wings 234f below a shutter 224f and a pair of gingival tie wings above the shutter 224f to provide a twin orthodontic bracket. The gingival tie wings can be spaced further apart to make the orthodontic bracket more symmetrical.

Referring now to FIGS. 38 to 41, still yet another embodiment of an orthodontic bracket is shown. In this embodiment, like reference numerals will be used to denote like components of the embodiment of FIGS. 12 to 15 with a "1000" added for clarity. As can be seen, the orthodontic bracket 1220 is similar to one of the orthodontic brackets disclosed in Applicant's U.S. Pat. No. 5,474,445 issued on Dec. 12. 1995, the contents of which are incorporated herein by reference. In this embodiment, a projection 1001 is formed on the gingival surface 1003 of the body 1222 in the interwing region. The shutter 1224 generally resembles a cruciform and has a gingival arm 1005 with an inverted doghouse shaped aperture 1267 in it so accommodate the projection 1001 and retain the shutter 1224 in the closed position. The shape of the aperture 1267 also permits a tool to enter the aperture so that a labially directed force can be applied to the shutter 1224 using the tool to release the shutter 1224 from the projection 1001. The mesial and distal arms 1007 and 1009 respectively of the shutter 1224 curve lingually into the archwire slot 1240. The arms 1007 and 1009 are resilient and are somewhat flattened when contacting a full dimension rectangular archwire 1242 accommodated in the archwire slot 1240 to apply a bias to move the archwire 1242 into the base of the archwire slot. In this way, a continuous rotation action and torque is applied to the archwire whether round or rectangular (even where that archwire is of relatively small cross-sectional dimension) to apply a continuous force to the tooth through the orthodontic bracket 1220. The occlusal arm 1011 of the shutter 1224 curves labially to define a single loop which surrounds a pivot pin 1013 to secure the shutter 1224 to the orthodontic bracket 1220 and to provide a shutter with a continuous smooth lingual surface.

Figure 41A:
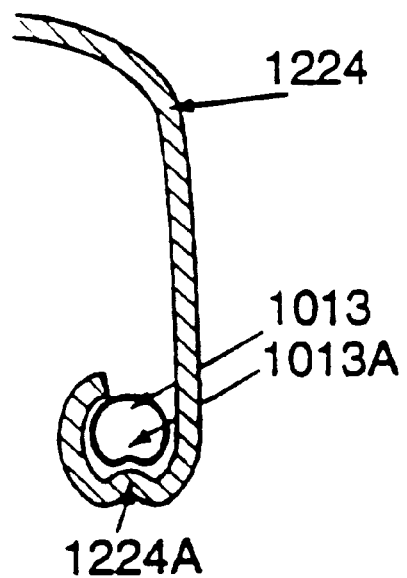
FIG. 41a is a cross-sectional view of an alternative embodiment of a pivot pin and shutter for use with the orthodontic bracket of FIG. 38.

FIG. 41a shows an alternative embodiment of the shutter and pivot pin design. In this embodiment, a dimple 1013a is formed in the pivot pin 1013 and an indentation 1224a if provided in the shutter 1224. The indentation 1224a and dimple 1013a cooperate when the shutter is in a closed position to provide further security to inhibit accidental opening of the shutter.

A similar arrangement of an orthodontic bracket 2220 to that described above is shown in FIGS. 42 to 45. In this embodiment, like reference numerals will be used to denote like components of the embodiment of FIGS. 12 to 15 with a "2000" added for clarity. As can be seen, the orthodontic bracket 2220 also has a shutter 2224 generally resembling a cruciform. The gingival arm 2005 of the shutter 2224 has a doghous shaped aperture 2267 in it to accommodate a projection 2001 and retain the shutter 2224 in the closed position. Unlike the previous embodiment, the mesial and distal arms 2007 and 2009 on the shutter 2224 are relatively rigid. A spring member in the form of a ribbon 700 is located on the lingual surface of the shutter 2224 and extends mesiodistally. The ribbon 700 is configures to provide a pair of convex lingually extending formations 702 that are aligned with the occlusal and gingival tie wings at opposed mesial and distal sides of the body 2222 and thus bear against an archwire 2242 located in the archwire slot 2240. The central portion 704 of the ribbon 700 is secured to the shutter 2224 with the lateral extremities 706 of the ribbon being free to slide horizontally over the lingual surface of the shutter 2224 and thereby allow flexure of the formations 702. In this manner, different thicknesses of archwires 2242 can be accommodated by the orthodontic bracket 2220 while still ensuring that a continuous force is applied to the tooth through the orthodontic bracket.

Figure 45:
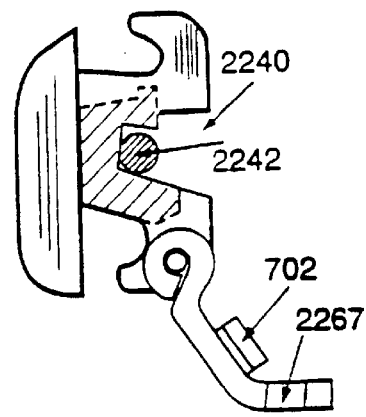
FIG. 45 is a side elevational view of the orthodontic bracket of FIG. 43 accommodating a round archwire.
Figure 45A:
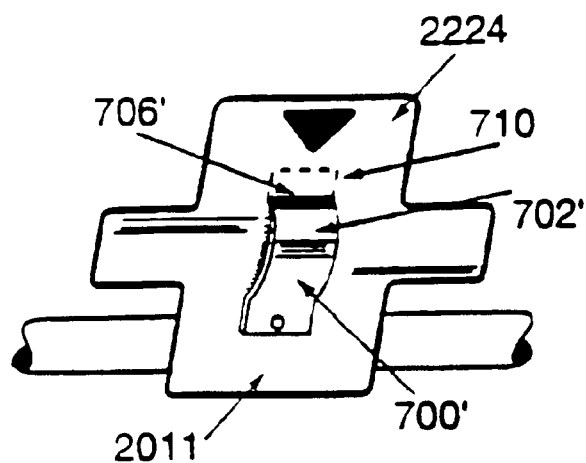
FIG. 45a is a front elevational view of an alternative embodiment of a shutter for use with the orthodontic bracket of FIG. 42.

FIG. 45a illustrates an alternative embodiment of a ribbon 700' for use with the orthodontic bracket 2220. In this embodiment, the ribbon 700' is secured to the lingual surface of the occlusal arm 2011 of the shutter 2224 adjacent one of its ends and extends in a gingival-occlusal direction. The other end 706' of the ribbon 700' is free to slide relative to the lingual surface of the shutter 2224 as indicated by the dotted line 710. The tong 700' presents a convex surface 702' which enters the archwire slot 2240 when the shutter is in a closed position to bias the archwire 2242 into the archwire slot.

Figure 46:
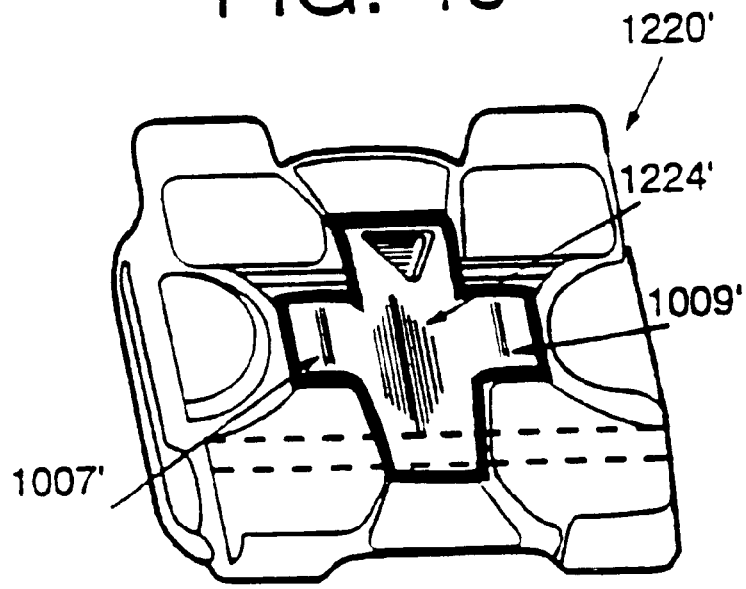
FIG. 46 is a front elevational view of yet another alternative embodiment of an orthodontic bracket in accordance with the present invention in a closed position.
Figure 47:
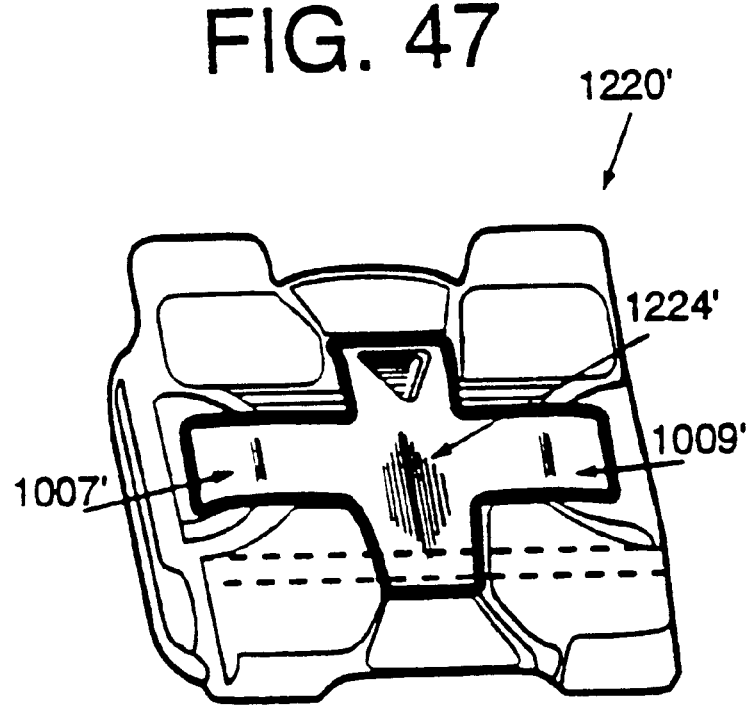
FIG. 47 is a front elevational view of yet another alternative embodiment of an orthodontic bracket in accordance with the present invention in a closed position.
Figure 48:
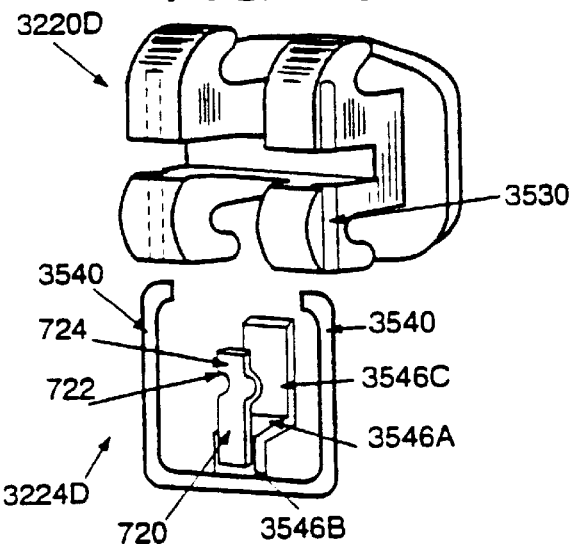
FIG. 48 is an exploded three-quarter perspective view of yet another alternative embodiment of an orthodontic bracket in accordance with the present invention similar to that shown in FIGS. 28 to 31.

FIGS. 46 and 47 illustrate alternative embodiments of orthodontic brackets 1220' similar to that illustrate in FIGS. 38 to 41. In these embodiments, like reference numerals will be used to indicate like components of the embodiment of FIGS. 38 to 41 with a "'" added for clarity. In the embodiment of FIG. 46, the shutter 1224' has short mesial and distal arms 1007' and 1009' which curve lingually into the archwire slot 1240' to apply a bias to an archwire 1242' accommodated by the archwire slot 1240'. In the embodiment of FIG. 47, the shutter 1224' has longer mesial and distal arms 1007' and 1009' which curve lingually into the archwire slot 1240' to apply a bias to an archwire 1242' accommodated by the archwire slot 1240'.

Referring now to FIGS. 48 to 52, still yet another embodiment of an orthodontic bracket 3220d is shown similar to that shown in FIGS. 28 to 31. In this embodiment, like reference numerals will be used to denote like components of the embodiment of FIGS. 28 to 31 with a "3000" added for clarity. As can be seen, the orthodontic bracket 3220d can be modified to provide a continuous seating action bias to an archwire accommodated in the archwire slot. In this arrangement, a spring member in the form of a resilient shim 720 is attached to the vertical arm 3546b of the support arm 3546. The shim 720 thus projects gingivally from the labial edge of the horizontal arm 3546a so as to be spaced from the lingual vertical arm 3546c. The shim 720 has a jog directed lingually toward the archwire slot 3240d and presents a generally convex surface 722 towards the archwire slot 3240d. The gingival edge 724 of the shim 720 recurves labially.

Figure 49:
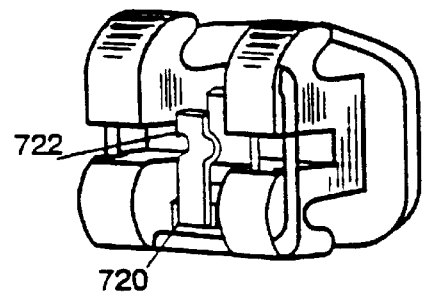
FIG. 49 is a three-quarter perspective view of the orthodontic bracket of FIG. 48 in a closed position.
Figure 50:
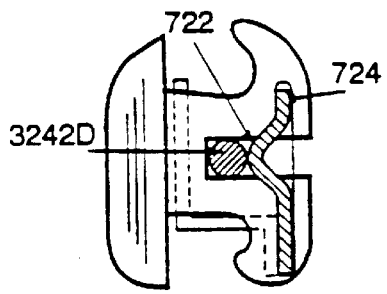
FIG. 50 is a side elevational view of the orthodontic bracket of FIG. 49 in a closed position.
Figure 51:
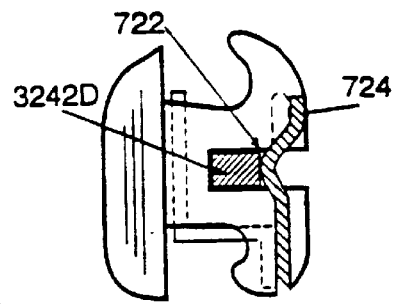
FIG. 51 is a side elevational view of the orthodontic bracket of FIG. 49 in a closed position.
Figure 52:
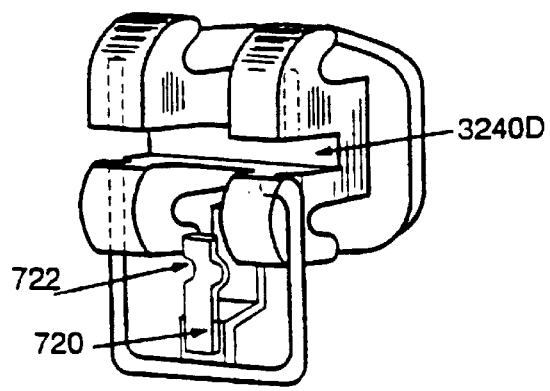
FIG. 52 is a three-quarter perspective view of the orthodontic bracket of FIG. 49 in the open position.

As the arms 3540 slide within the slots 3530 to the move the clip 3538 to a closed position as shown in FIG. 49, the convex surface 722 of the shim 720 engages the archwire 3242d and provides a continuous biasing action against the archwire (best seen in FIG. 50). As may be seen in FIG. 51, the resilience of the shim 720 allows the orthodontic bracket 3220d to accommodate different sizes and configurations of archwires 3242d while maintaining a continuous action against the archwire.

Figure 53:
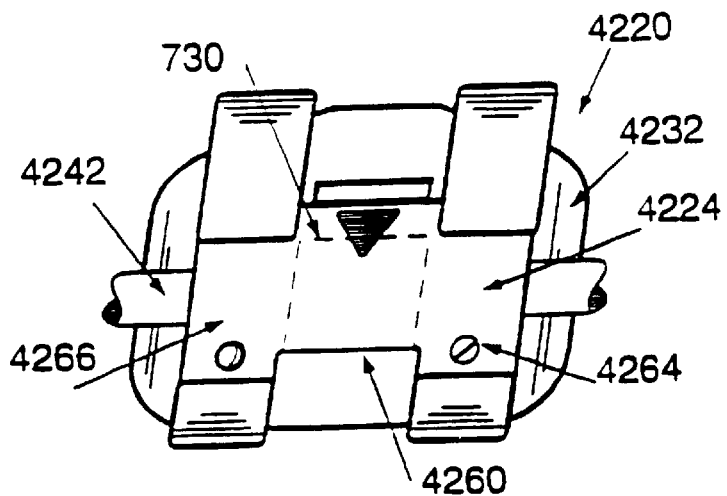
FIG. 53 is a front elevational view of an alternative embodiment of an orthodontic bracket in accordance with the present invention having a sliding shutter similar to that shown in FIGS. 12 to 15.
Figure 55:
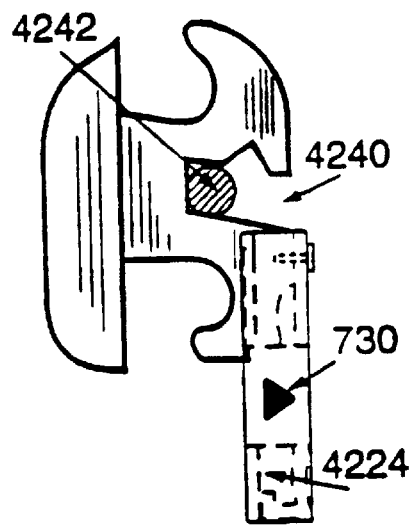
FIG. 55 is a side elevational view of the orthodontic bracket of FIG. 53 with the shutter in the open position.
Figure 54:
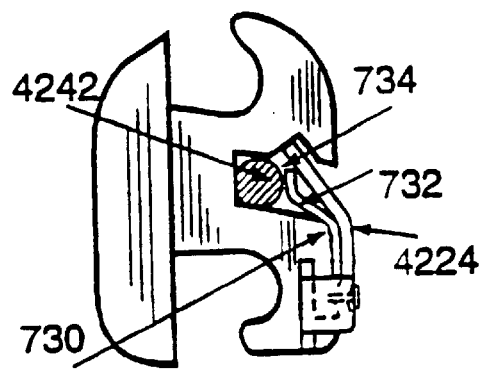
FIG. 54 is a side elevational view of the orthodontic bracket of FIG. 53.

Referring now to FIGS. 53 to 55, still yet another embodiment of an orthodontic bracket 4220 is shown similar to that shown in FIGS. 12 to 15. In this embodiment, like reference numerals will be used to denote like components of the embodiment of FIGS. 12 to 15 with a "4000" added for clarity. As can be seen, the orthodontic bracket 4220 can be modified to provide a continuous bias to an archwire accommodated in the archwire slot. In this embodiment, a spring member in the form of a resilient shim 730 is secured to the lingual surface of the shutter 4224 adjacent the interwing region of the body 4220. The shim 730 is integrally formed with the shutter 4224 and is folded lingually about the occlusal edge 4260 of the shutter between the arms 4264 and 4266 respectively. The shim 730 is curved lingually to present a generally convex surface 732 spaced from the shutter 4224 and its end 734 recurved to form a smooth lip engaged with the lingual face of the shutter 4224. The end 734 of the shim 730 is free to slide relative to the shutter 4224 when the convex surface 731 is flattened due to contact with an archwire 4242 in the archwire slot 4240. The shim 730 is thus able to continuously exert a corrective force upon different configurations of archwires 4242 within the archwire slot 4240 when the shutter 4224 is in the closed position.

Figure 56:
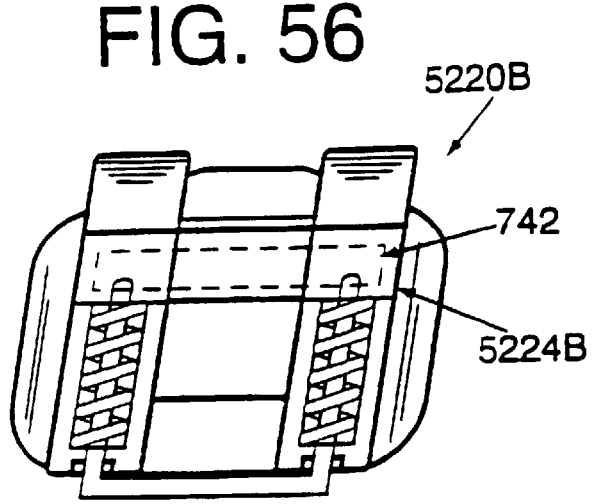
FIG. 56 is a front elevational view of a further embodiment of an orthodontic bracket in accordance with the present invention having a resiliently biased locking shutter similar to that shown in FIGS. 25 to 27.
Figure 57:
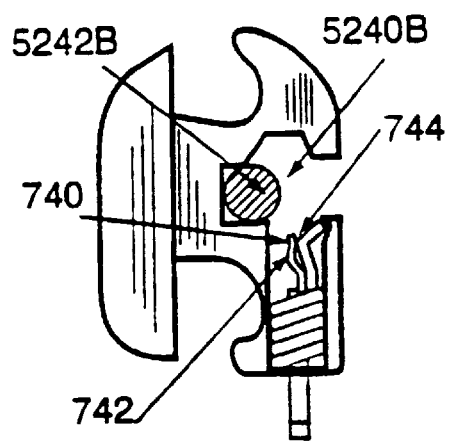
FIG. 57 is a side elevational view of the orthodontic bracket of FIG. 56 in an open position.
Figure 58:
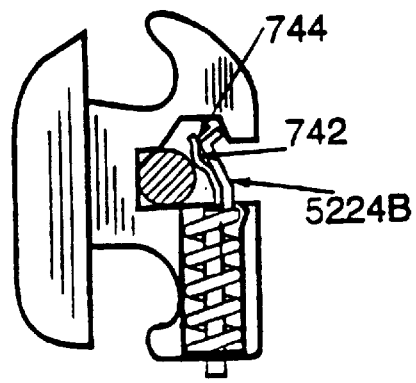
FIG. 58 is a side elevational view of the orthodontic bracket of FIG. 56 in a closed position.
Figure 59:
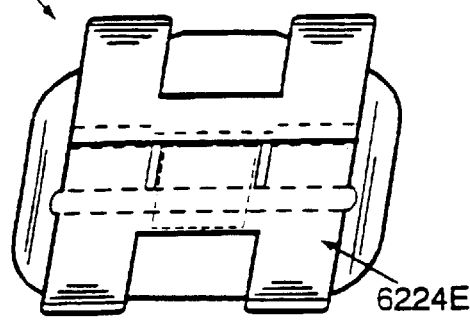
FIG. 59 is a front elevational view of yet another embodiment of an orthodontic bracket in accordance with the present invention similar to that shown in FIGS. 32 to 36.
Figure 60A:
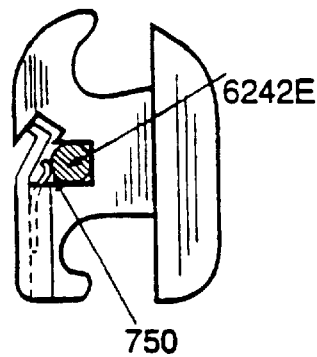
FIG. 60a is a side elevational view of the orthodontic bracket of FIG. 59.
Figure 61:
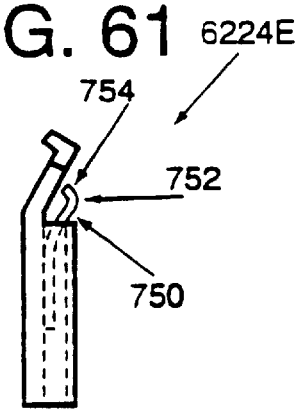
FIG. 61 is a side elevational view of a shutter forming part of the orthodontic bracket of FIG. 59.
Figure 62:
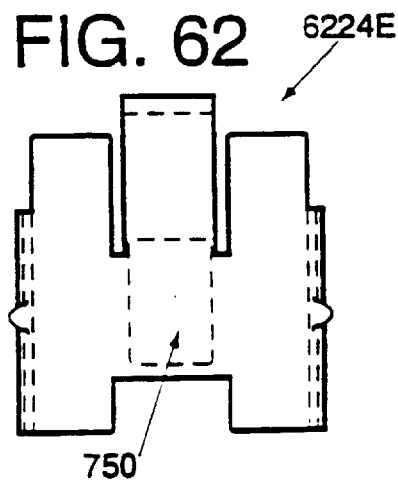
FIG. 62 is a front elevational view of the shutter of FIG. 61.
Figure 63:
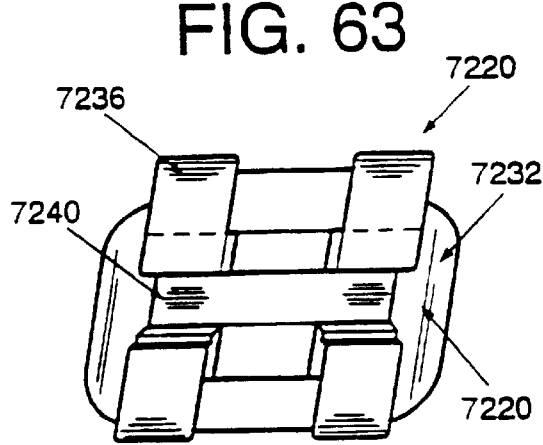
FIG. 63 is a front elevational view of still a further embodiment of an orthodontic bracket in accordance with the present invention with the shutter removed.
Figure 64:
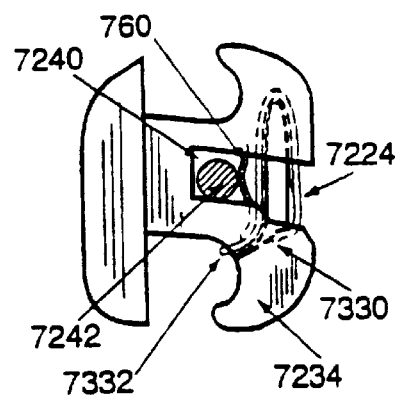
FIG. 64 is a side elevational view of the orthodontic bracket of FIG. 63 with the shutter installed.
Figure 65:
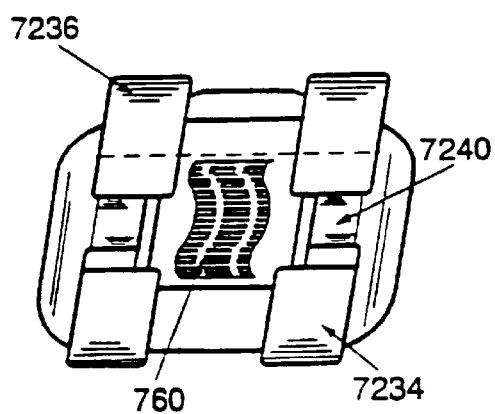
FIG. 65 is a front elevational view of the orthodontic bracket of FIG. 63 with the shutter installed.
Figure 66:
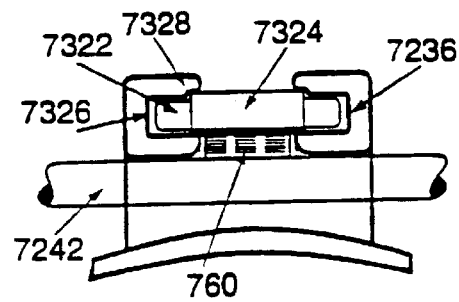
FIG. 66 is a top plan view of the orthodontic bracket of FIG. 65.

Referring now to FIGS. 56 to 58, still yet another embodiment of an orthodontic bracket 5220b is shown similar to that shown in FIGS. 25 to 27. In this embodiment, like reference numerals will be used to denote like components of the embodiment of FIGS. 25 to 27 with a "5000" added for clarity. As can be seen, the orthodontic bracket 5220b can be modified to provide a continuous bias to an archwire accommodated in the archwire slot. In the arrangement shown, a spring member in the form of a resilient shim 740 is formed on the lingual face of the shutter 5224b in the archwire slot 5240b. The shim 740 is formed with a convex lingual surface 742 that engages an archwire 5242b when the shutter 5224b is in the closed position. The shim 740 is secured to the shutter 5224b adjacent its occlusal end only and therefore, the gingival end 744 of the shim 740 is free to slide relative to the shutter 5224b. In this manner, the shim 740 may flex to accommodate different sizes and shapes of archwires 5242b accommodated in the archwire slot 5240b to provide a continuous action on the archwire wire.

Referring now to FIGS. 59 to 62, still yet another embodiment of an orthodontic bracket 6220e is shown similar to that shown in FIGS. 32 to 36. In this embodiment, like reference numerals will be used to denote like components of the embodiment of FIGS. 32 to 36 with a "6000" added for clarity. As can be seen, the orthodontic bracket 6220e can be modified to provide a continuous bias to an archwire accommodated in the archwire slot. In the arrangement shown, a spring member in the form of a shim 750 is secured to the lingual surface of the shutter 6224e and presents a convex surface 752 toward the archwire slot 6240e to engage an archwire 6242b in the same manner as described above to provide a continuous action on the archwire wire. The gingival edge 754 of the shim is free to slide relative to the lingual surface of the shutter 6224e.

A continuously acting orthodontic bracket may also be provided with self-locking labial brackets such as those shown in U.S. Pat. No. 5,094,614 to Wildman, the contents of which are incorporated herein by reference. As shown in FIGS. 63 to 71, the orthodontic bracket 7220 has a pair of wings 7242 with an archwire slot 7240 to receive an archwire 7242.

Figure 67:
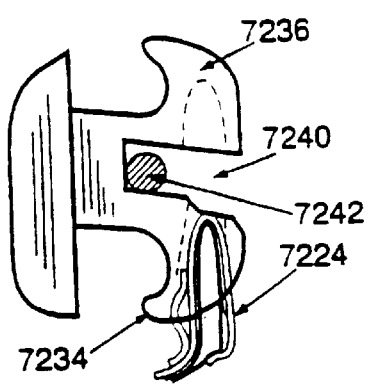
FIG. 67 is a side elevational view of the orthodontic bracket of FIG. 63, similar to FIG. 64, with the shutter in an open position.
Figure 69:
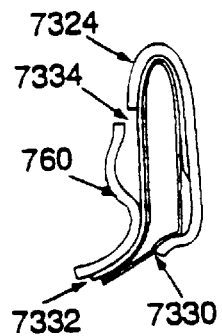
FIG. 69 is a side elevational view of an alternative embodiment of a shutter for use with the orthodontic bracket of FIG. 63.
Figure 68:
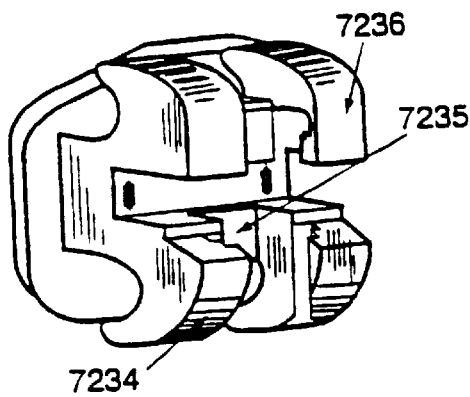
FIG. 68 is a three-quarter perspective view of the orthodontic bracket of FIG. 63.

A shutter 7224 is located between the gingival and occlusal tie wings located at opposed mesial and distal sides of the body 7222 and includes a central body portion 7322 encompassed by a locking spring 7324. The mesial and distal edges of the shutter body 7322 are received within grooves 7326 so that the shutter 7224 may slide between open and closed positions. The grooves 7326 have undercuts 7328 that terminate at steps 7330 in the occlusal and gingival tie wings 7234 and 7236 respectively. The steps 7330 receive one end of a spring 7324. The opposite ends are formed as an occlusal tail. A spring member in the form of a resilient shim 760 is secured to the tail 7332 so as to be spaced from the retaining spring 7324. A lingual step 7235 accommodates the shim 760 from a lingual aspect. The shim 760 thus engages an archwire 7242 in the archwire slot 7240 when the shutter 7224 is in the closed position in a resilient manner to provide a continuous biasing action against the archwire as shown in FIG. 6b. The step 7330 retains the shutter 7224 in the closed position with the resilient shim 760 biased against the archwire 7242. As shown in FIG. 67, the shim 760 may be secured to the tail 7332 as a separate structure. Alternatively, as shown in FIG. 69, the shim 760 may be formed on the tail 7332 of a liner layer 7334 that encompasses the body 7322. The spring 7324 extends over the upper edge of the body 7322 and terminates above the upper edge of the shim 760. The shim 760 is thus free to flex to accommodate different sizes and dispositions of archwires while providing a continuous action on the archwire.

Figure 70:
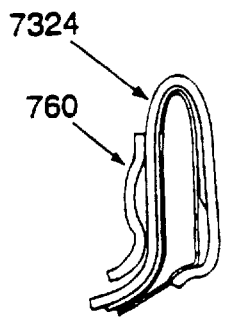
FIG. 70 is a side elevational view of a further alternative embodiment of a shutter for use with the orthodontic bracket of FIG. 63.
Figure 71:
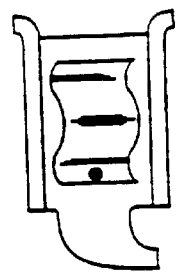
FIG. 71 is a rear elevational view of the shutter of FIG. 70.

Similarly, as shown in FIG. 70, the shim 760 may be secured at its upper edge to the spring 7324 with the lower edge free of the tong to slide relative to the shutter upon flexure of the shim 760.

Figure 72:
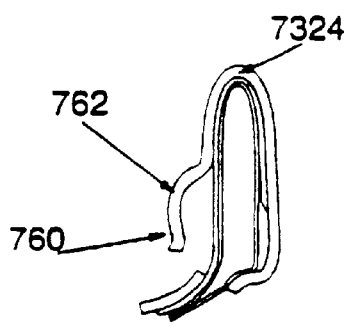
FIG. 72 is a side elevational view of a still further embodiment of a shutter for use with the orthodontic bracket of FIG. 63.
Figure 73:
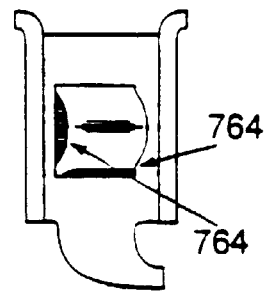
FIG. 73 is a rear elevational view of the shutter of FIG. 72.
Figure 74:
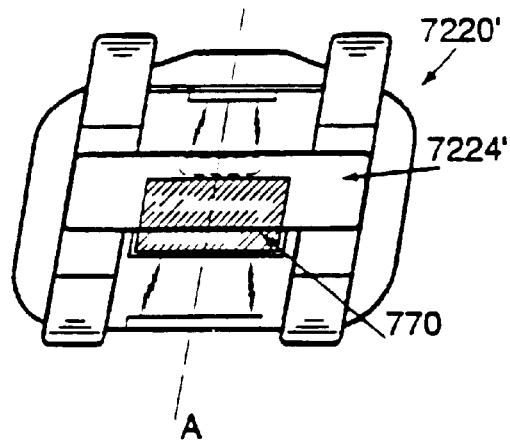
FIG. 74 is a front elevational view of yet another alternative embodiment of an orthodontic bracket in accordance with the present invention.
Figure 75:
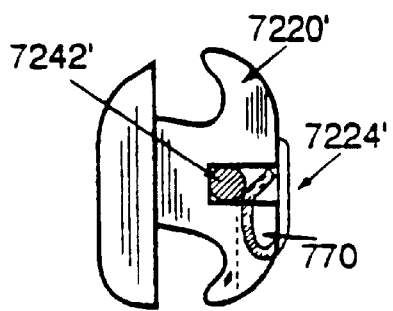
FIG. 75 is a side elevational view of the orthodontic bracket of FIG. 74 in a closed position.
Figure 76:
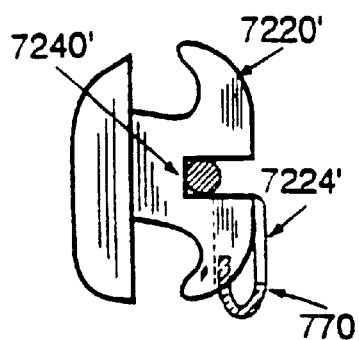
FIG. 76 is a side elevational view of the orthodontic bracket of FIG. 75 in an open position.
Figure 77:
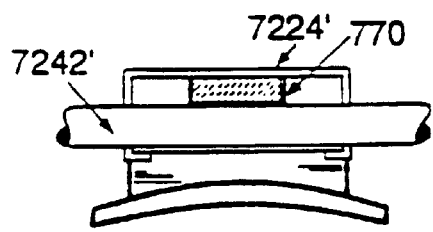
FIG. 77 is a cross-sectional view of FIG. 76.
Figure 78:
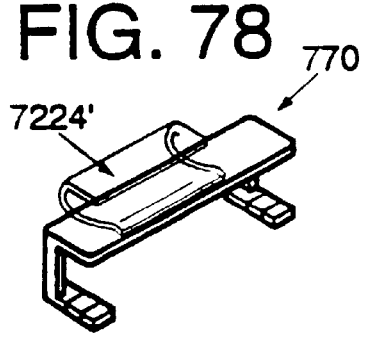
FIG. 78 is a perspective view of a shutter used in the orthodontic bracket of FIG. 74.
Figure 79:
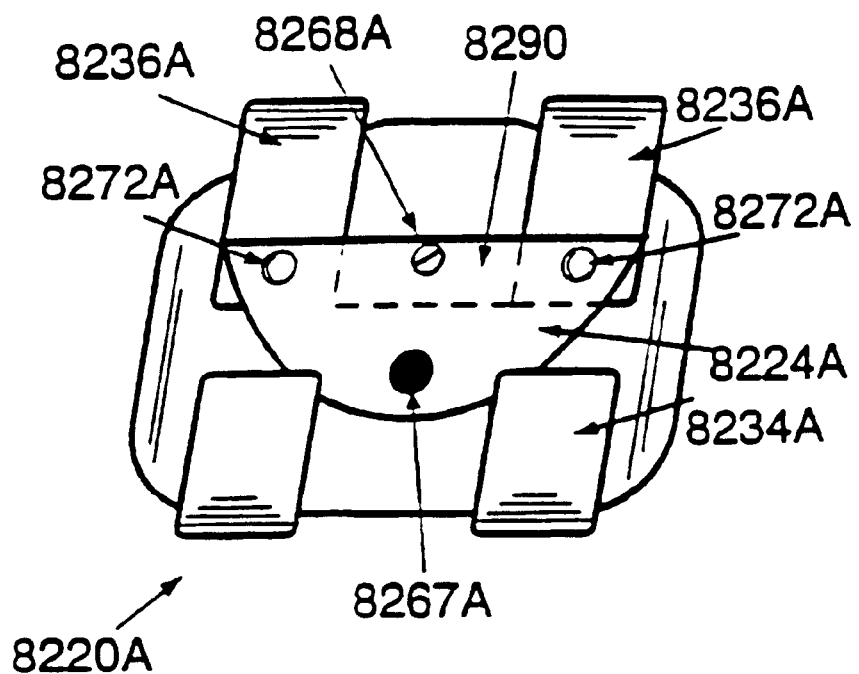
FIG. 79 is a front elevational view of yet another alternative embodiment of an orthodontic bracket in accordance with the present invention.
Figure 80:
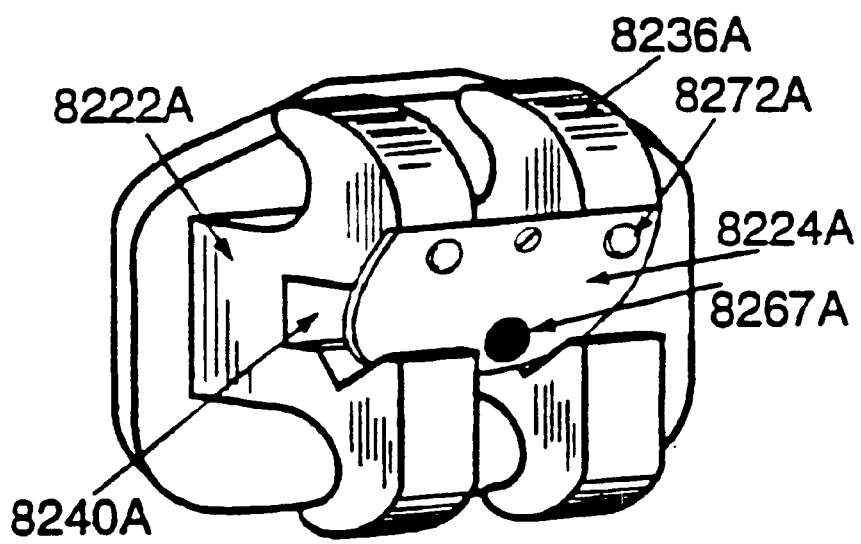
FIG. 80 is a perspective view of the orthodontic bracket of FIG. 79.

An alternative arrangement for the shim 760 is shown in FIGS. 72 and 73. In this embodiment, the resilient shim 760 is defined in the lingual aspect of the outer layer of the spring 7324. Three sides of the shim 760 are defined by slots 764 cut into the lingual aspect of the outer layer of the spring to define the periphery of the shim 760. The resultant shim defines an inwardly convex surface 762 that resiliently engages the archwire. Naturally, such a shim 760 may be formed integrally with the springs 7324 to facilitate manufacture.

A further modification of an existing orthodontic bracket 7220' is shown in FIGS. 74 to 78 in which the orthodontic bracket known as the Damon bracket and shown in U.S. Pat. No. 5,439,378, the contents of which are incorporated herein by reference, is modified to provide a spring member in the form of a resilient shim 770 on the lingual surface of the shutter 7224'. Shutter 7224' may be extended occlusally to accommodate the shim 770 which in this embodiment is formed by folding a continuous extension of the shutter 7224' back upon itself. The shim 770 presents a convex surface 772 which enters the archwire slot 7240' when the shutter 7224' is in a closed position. One end 744 of shim 770 if free to slide relative to the shutter 7224'. In this manner, the shim 770 may flex to accommodate different sizes and shapes of archwires 7242' accommodated in the archwire slot 7240' to provide a continuous action on the archwire.

As those of skill in the art will appreciate, in the embodiments illustrated in FIGS. 38 to 78, the spring member may be formed as a separate member and attached to the shutter adjacent either its gingival or occlusal ends in a manner so that it extends into the archwire slot to bias the archwire. Alternatively, the spring member may be integrally formed with the shutter by a folding portion of the shutter about an edge. If the spring member is to be integrally formed with the shutter, a continuous extension of the shutter is typically folded about either a gingival or occlusal edge of the shutter and is configured so that it extends into the archwire slot to bias the archwire.

Referring now to FIGS. 79 to 82, still yet another embodiment of an orthodontic bracket 8220 is shown similar to that shown in FIGS. 16a to 17a. In this embodiment, like reference numerals will be used to denote like components of the embodiment of FIGS. 16a to 17b with a "8000" added for clarity. As can be seen, the resilient locking shutter 8224a is pivotally secured to a boss 8290 that extends between the gingival tie wings 8236a by way of a centrally located pivot pin 8268a. The boss 8290 is located on a lingually bevelled labial surface of the body 822a. Thus, the shutter 8224a is inclined. One edge 8292 of the locking shutter 8224a is arcuate to give the shutter a generally semi-circular appearance. Deflection notches 8248a are formed in the archwire slot 8240a adjacent the occlusal tie wings 8234a.

Figure 81:
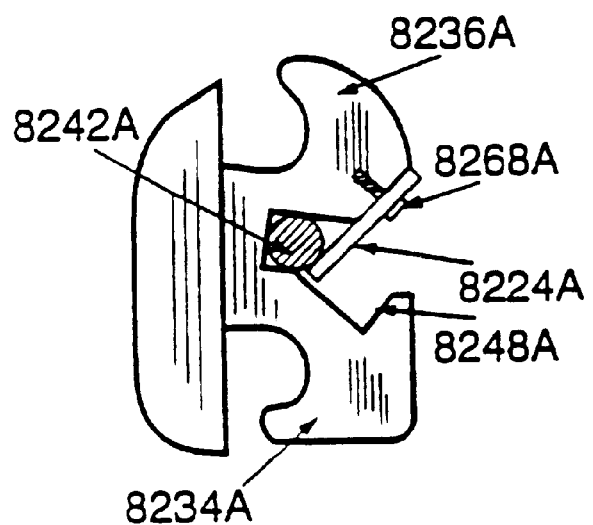
FIG. 81 is a side elevational view of the orthodontic bracket of FIG. 79.
Figure 82:
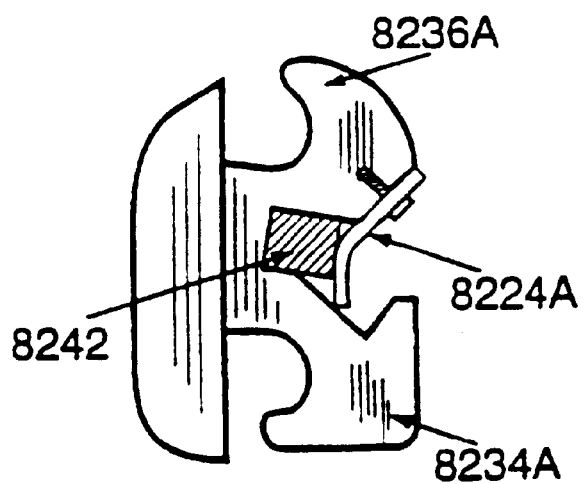
FIG. 82 is a side elevational view of the orthodontic bracket of FIG. 79 accommodating a larger archwire.

Dimples (not shown) are formed on each of the gingival tie wings 8236a and corresponding indentations 8272a are formed on the locking shutter 8224a. The dimples and indentations 8272a cooperate when the locking shutter 8224a is either in the open or closed positions to retain the locking shutter in that position. An aperture 8267a is provided in the shutter 8224a to receive a tool and facilitate movement of the shutter 8224a. The locking shutter 8224a can be pivoted about pivot in 8268a so as to bring the shutter 8224a into engagement with the archwire 8242a in the archwire slot 8240a as shown in FIG. 81 by overcoming the detent provided by the indentations 8272a and dimples. In this position, the locking shutter 8224a is effective to inhibit removal of an archwire 8242 from the archwire slot 8240a and provides a continuous action on the archwire. The locking shutter 8224a can be readily moved to the open position by rotating the locking shutter about the pivot pin 8268a to allow access to the archwire slot 8240a. As can be seen in FIG. 82, when a larger archwire 8242 is accommodated by the archwire slot 8240a, the shutter 8224a flexes to accommodate the archwire yet provide a continuous action on the archwire. The deflection notches 8248a and the angulated orientation of the shutter 8240a inhibit the shutter 8224a from moving labially out of the archwire slot 8240a.

Another embodiment of an orthodontic bracket 9220 utilizing an alternative shutter structure is shown in FIGS. 83 to 87. In this embodiment, like reference numerals will be used to denote like components of the embodiment of FIGS. 12 to 15 with a Suffix '9000' added for clarity. As shown in FIGS. 83 to 87, the shutter 9224 is pivotal and is formed from a wire 9001 bent into a generally cruciform outline. The wire 9001 has opposite ends that are turned over to provide oppositely-directed tails 9003 and 9005. The tails 9003, 9005 extend parallel to a common axis but are offset from one another.

Each of the tails 9003, 9005 is received in a respective bore 9007 formed in each of the occlusal tie wings 9234. The tails 9003, 9005 are free to rotate within the respective bores to permit pivotal movement of the shutter 9224.

The wire 9001 defines a pair of oppositely-directed arms 9009, 9011 which extend across the archwire slot 9240. A horizontal recess 9013 is formed in each of the gingival tie wings 9236 adjacent the archwire slot 9240 to provide an abutment surface to limit pivotal movement of the shutter 9224 towards the archwire slot 9240.

Figure 84:
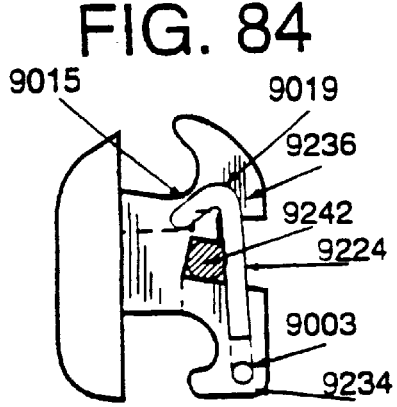
FIG. 84 is a side elevational view of the orthodontic bracket of FIG. 83 in a closed position and accommodating an archwire.
Figure 85:
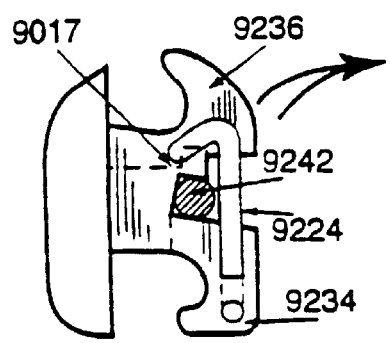
FIG. 85 is a side elevational view of the orthodontic bracket of FIG. 83 showing the initial release of the shutter.
Figure 86:
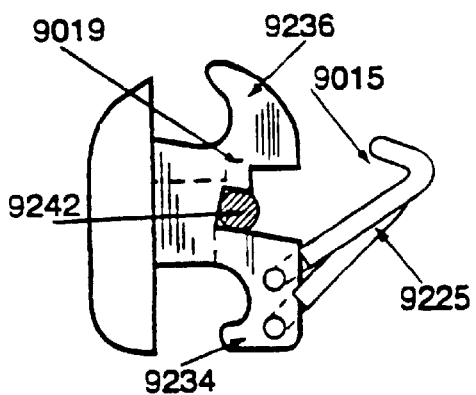
FIG. 86 is a side elevational view of the orthodontic bracket of FIG. 83 showing further movement of the shutter.

The wire 9001 between the arms 9009, 9011 is formed into a rearwardly-projecting hook 9015 as can best be seen in FIG. 84 and is received within groove 9017. An extension 9019 is formed on the gingival surface of the body 9222 and passes through the hook 9015 when the shutter 9224 is in a closed position to provide a frictional fit between the hook 9015 and body 9222 and retain the shutter in the closed position.

Figure 87:
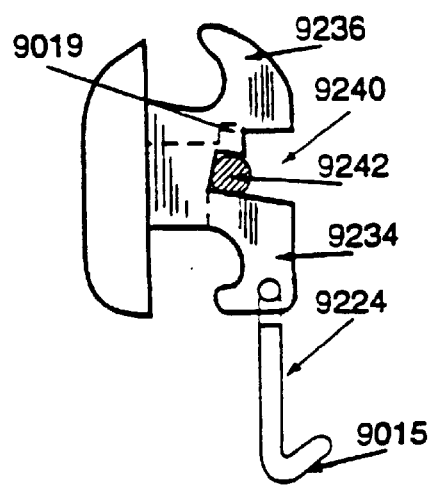
FIG. 87 is a side elevational view of the orthodontic bracket of FIG. 83 showing the shutter in a fully open position.

As shown in FIG. 84, the hook 9015 retains the shutter 9224 against the archwire 9242 and inhibits relative movement between the archwire and the body 9222 of the orthodontic bracket 9220. To release the archwire 9242, the shutter 9224 is caused to pivot about the offset tails 9003, 9005 to release the hook 9015 from the extension 9109. As the shutter 9224 is rotated, the eccentricity of the axes of rotation of the tails 9003, 9005 causes a torsional resistance due to flexure of the wire 9001 tending to return the shutter 9224 to the closed position. This movement is opposed until such time as the shutter 9224 goes over center, at which point the shutter 9224 becomes biased to the open position as shown in FIG. 87. In this way, the shutter 9224 is resiliently biased toward the body 9222 as it is moved towards the closed position but remains in a stable, open position at other times.

Figure 83:
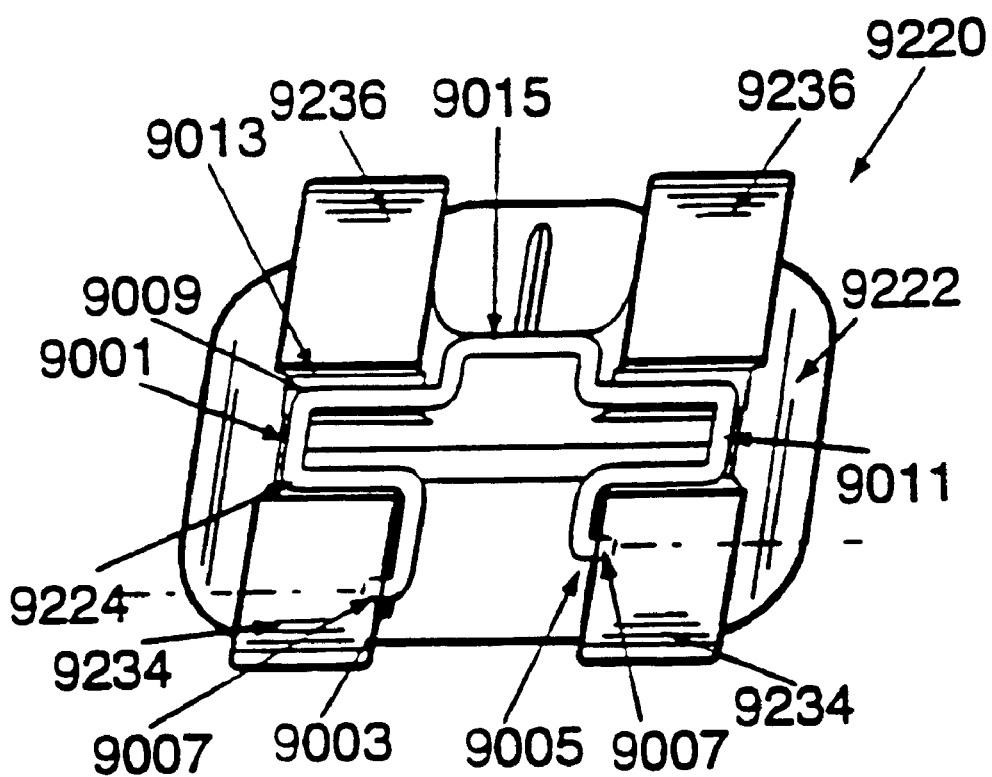
FIG. 83 is a front elevational view of yet another alternative embodiment of an orthodontic bracket in accordance with the present invention.
Figure 88:
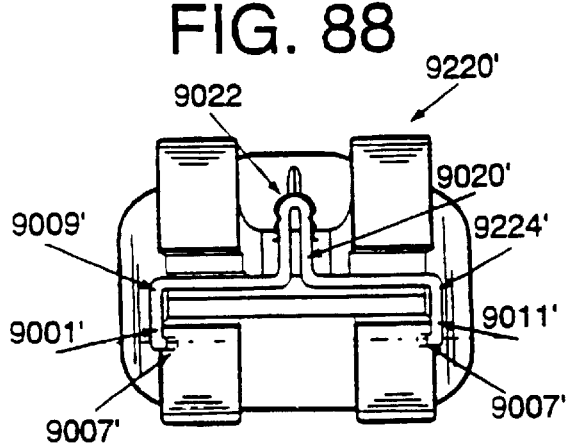
FIG. 88 is a front elevational view of yet another alternative embodiment of an orthodontic bracket in accordance with the present invention.
Figure 89:
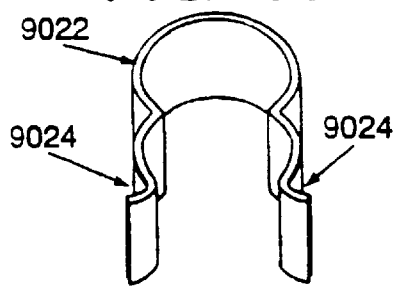
FIG. 89 is a perspective view of a component forming part of the orthodontic bracket of FIG. 88.

A further embodiment of an orthodontic bracket 9220' utilizing a wire for a shutter 9224' is shown in FIGS. 88 and 89, where like components of the previous embodiment will be described using like reference numerals with a suffix """ added for clarity. In this embodiment, the shutter 9224' is formed from a wire 9001' having oppositely directed tails 9003', 9005'. Each of the tails 9003', 9005' is pivotally received within bores 9007' which are aligned on a common axis to allow free pivotal movement of the shutter 9224'. The bores may also be offset as shown in FIG. 83.

Figure 90:
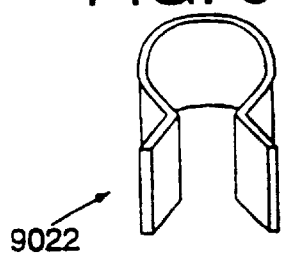
FIG. 90 is a perspective view of an alternative embodiment of the component of FIG. 89.

The wire 9001' between the arms 9009', 9011' is formed as an elongate U-shaped projection 9020 and is received within a locking clip 9022. As can best be seen in FIG. 89, locking clip 9022 is generally U-shaped with serpentine limbs terminating in outwardly-flared ends 9024. The projection 9020 may be received between the flared ends 9024 to force the limbs apart but is then resiliently retained between the limbs in a stable manner. The locking clip 9022 may alternatively have a generally circular section as shown in FIG. 90 but it is believed the slip 9022 shown in FIG. 89 facilitates insertion of the projection 9020. Again, the shutter 9224' retains the archwire 9242' within the archwire slot 9240' when the locking clip 9022 retains the shutter 9224' in a closed position.

Figure 91A:
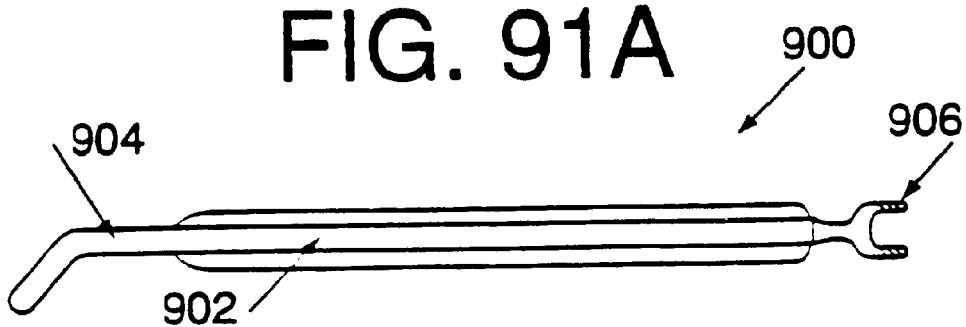
FIGS. 91a and 91b are side elevational views of embodiments of an orthodontic tool.
Figure 91B:

Referring now to FIGS. 91a and 91b, orthodontic tools 900 are shown which are suitable to open and close the shutters of the orthodontic brackets. As can be seen, each orthodontic tool 900 comprises a central body portion 902, a nose-shaped portion 904 at one end of the body portion for opening the shutter and a generally square corrugated fork-shaped portion 906 at the opposite end of the body portion 902 for gripping and guiding archwires lingually into the archwire slots to facilitate closure of the shutters. The fork-shaped portion straddles the outside of the bracket mesially and distally. In use, the nose-shaped portion 904 is inserted into the aperture in the shutter and a force is applied to the shutter using the tool 900 to move the shutter in the desired manned. In the embodiment of FIG. 91a, the fork-shaped portion 906 is aligned with the body portion 902 while in the embodiment of FIG. 91b, the fork-shaped portion 906 is at right angles to the body portion. Other angles between the body portion 902 and the fork-shaped portion 906 are of course suitable. Also, the shape of the nose-shaped portion 904 can vary to complement the aperture in the shutter.

Figure 92A:
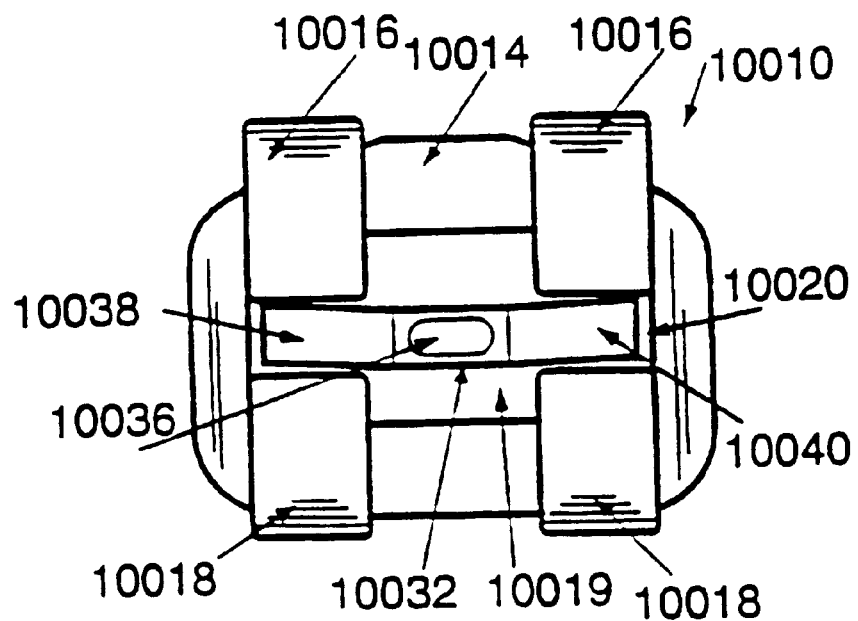
FIG. 92a is a front elevational view of another embodiment of an orthodontic bracket in accordance with the present invention.
Figure 92B:
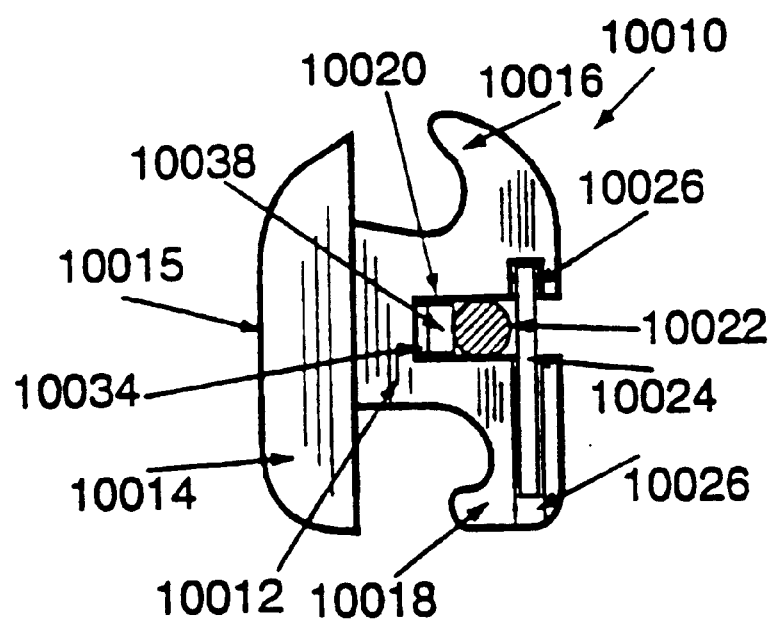
Figure 92C:
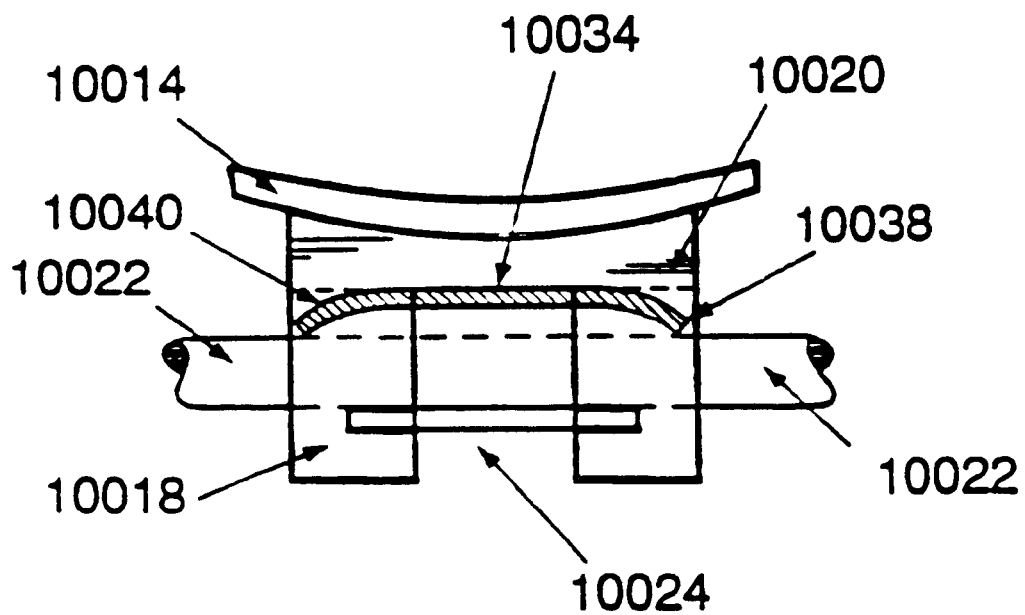

Referring now to FIGS. 92a to 92c sill yet another embodiment of an orthodontic bracket is shown and is generally indicated to by reference numeral 10010. The orthodontic bracket 10010 includes a body 10012 and a lingual mounting pad 10014 attached to the body. The mounting pad 10014 has a lingual surface 10015 to be attached to a tooth. A pair of gingival tie wings 10016 and a pair of occlusal tie wings 10018 extend from a labial surface of the body 10012. The gingival tie wings 10016 and the occlusal tie wings 10018 curve lingually. Both the gingival tie wings 10016 and the occlusal tie wings 10018 at opposed mesial and distal sides of the body are separated by an interwing region 10019 of the body 10012. An archwire slot 10020 extends mesiodistally across the body between the gingival and occlusal tie wings at opposed mesial and distal sides of the body and opens labially to receive an archwire 10022. The archwire slot 10020 is interrupted mesiodistally in the interwing region 10019. A locking shutter 10024 is accommodated by recesses 10026 in the gingival and occlusal tie wings and is moveable between a closed position where the archwire is locked into the archwire slot and access to and the release of the archwire sot 10020 is inhibited, and an open position where access to the archwire slot is permitted.

Within the archwire slot 10020 is a slot activator in the form of a generally rectangular, resilient spring member 10032 formed of suitable material such as for example Nickel-Titanium or spring stainless steel. The spring member 10032 extends mesiodistally along the archwire slot. The spring member 10032 has a central portion 10034 secured to the lingual wall of the archwire slot 10020 such as for example by way of a weld 10036 or a sleeve (not shown). Opposed ends of the spring member 10032 curve labially towards the locking shutter 10024 to define protrusive mesial and distal wings 10038 and 10040. The mesial and distal wings 10038 and 10040 of the spring member 10032 extend into the archwire slot 10020 starting from the lingual wall of the archwire slot a distance equal to approximately one third to one half of the depth of the archwire slot. The archwire slot 10020 formed in the body 10012 is mildly deeper than in conventional orthodontic brackets to accommodate the thickness of the central portion 10034 of the spring member 10034.

In use, when an archwire 10022 is placed into the archwire slot 10020 and the locking shutter 10024 is closed, the mesial and distal wings 10038 and 10040 of the spring member 10032 contact the archwire 10022 to bias it towards the locking shutter 10024. As shown in FIGS. 92b and 92c, when a small round archwire is used, the archwire 10022 is biased by the spring member 10032 to control and seat the archwire towards the locking shutter. During initial treatment, biasing of the archwire 10022 in this manner provides initial tooth movements to produce accurate rotation corrections and in-out (horizontal plane) movements of teeth. During the middle of treatment, biasing of the archwire in this manner controls and supports bodily tooth movement preventing rotation of teeth as they slide along a straight archwire by a pull force.

Figure 92D:
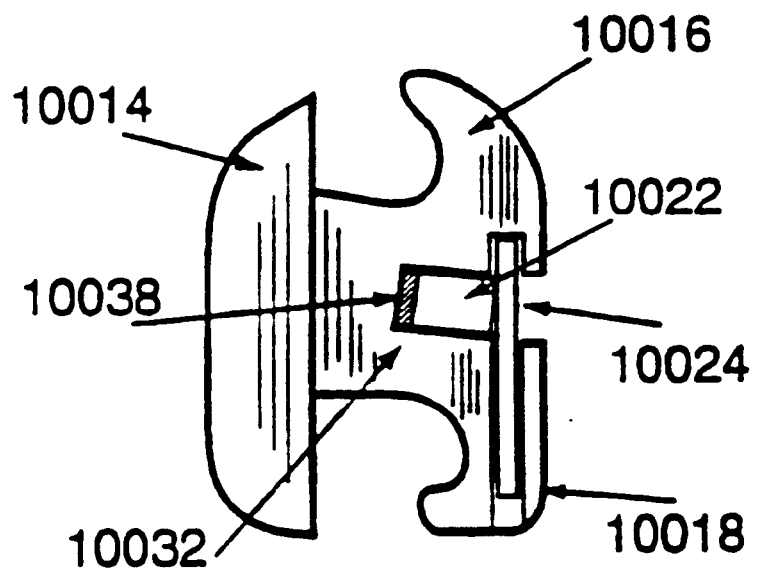

FIG. 92d shows the orthodontic bracket 10010 accommodating a large rectangular archwire 10022 in the archwire slot 10020 which is used at the end of treatment. In this case, the labially curved mesial and distal wings 10038 and 10040 of the spring member 10032 are partially flattened by the archwire but continue to act on the archwire to bias it towards the locking shutter 10024. Biasing the archwire 10022 in this manner applies a labial force on the archwire against the locking shutter 10024 to produce desired root torque in the tooth root and crown.

Figure 93:
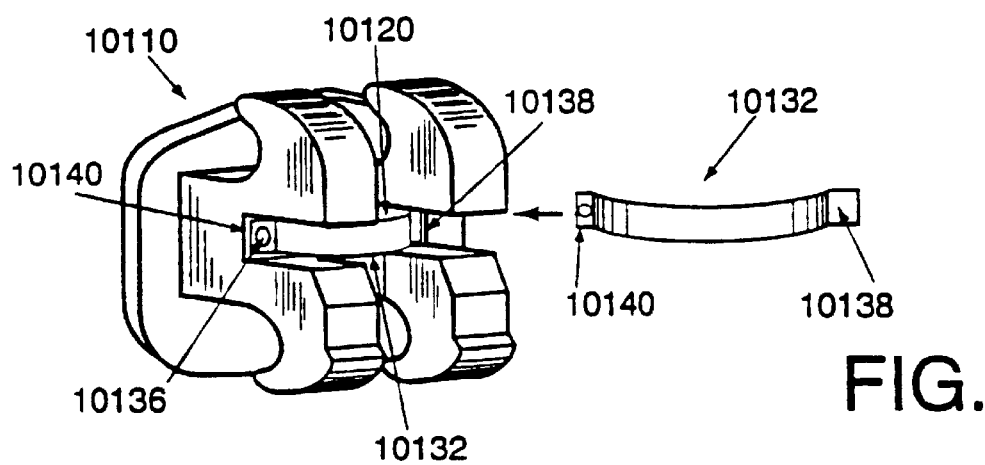
FIG. 93 is a perspective view of a portion of another embodiment of an orthodontic bracket in accordance the present invention.

Referring now to FIG. 93, still yet another embodiment of an orthodontic bracket is shown and is generally indicated to by reference numeral 10110. In this embodiment, the slot activator is in the form of a generally rectangular, convex resilient spring member 10132 formed of spring stainless steel. The mesial and distal ends 10138 and 10140 of the spring member 10132 are flattened. Distal end 10140 of the spring member 10132 is secured to the lingual wall of the archwire slot 10120 by way of a weld 10136 while the mesial end 10138 of the spring member 10132 is free.

Although the distal end of the spring member 10132 is shown attached to the body, it should be apparent to those of skill in the art that the mesial end of the spring member 10132 may be secured to the body with the distal end of the spring member 10132 being free. The length of the spring member 10132 is less than the length of the archwire slot 10120 so that the free end of the spring member remains in the archwire slot when the spring member 10132 is partially flattened by a large rectangular archwire accommodated by the archwire slot.

The orthodontic bracket 10110 functions in a similar manner to the previous embodiment. When a small round archwire is placed in the archwire slot 10120 and the locking shutter (not shown) is closed, the convex spring member 10132 biases the archwire 10122 towards the locking shutter. When a large rectangular archwire 10122 is placed in the archwire slot 10120, the spring member is only partially flattened and biases the archwire towards the locking shutter.

Figure 94:
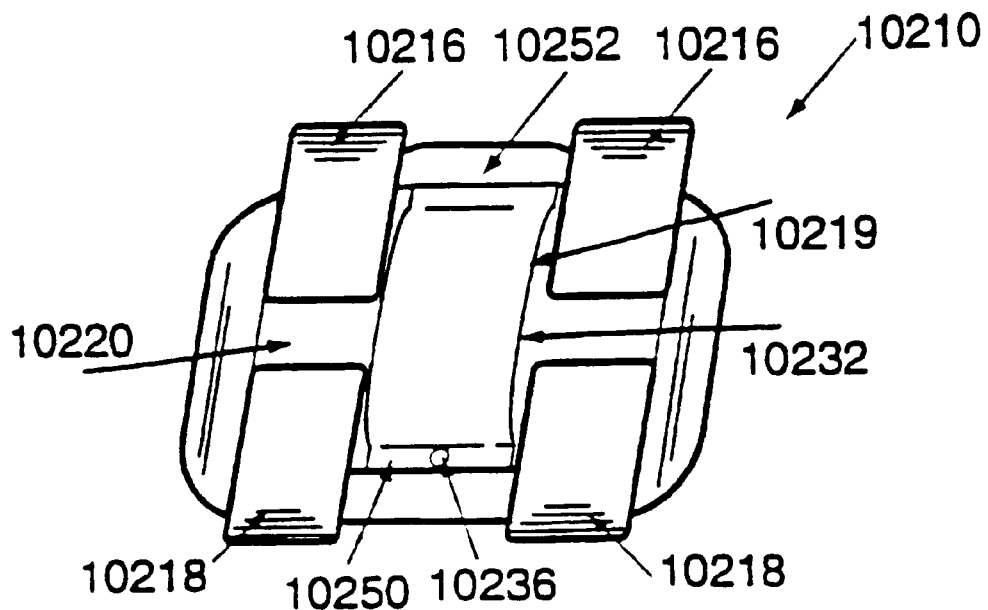
FIG. 94 is a front elevational view of yet another embodiment of an orthodontic bracket in accordance with the present invention.

Referring now to FIG. 94, still yet another embodiment of an orthodontic bracket is shown and is generally indicated to by reference numeral 10210. In this embodiment, the slot activator is similar to that shown in the previous embodiment except that the spring member 10232 is oriented to extend occlusiogingivally in the interwing region 10219 between the occlusal and gingival tie wings 10218 and 10216 respectively. The occlusal end 10250 of the spring member 10232 is secured to the body by way of a weld 10236 while the gingival end 10252 of 10 the spring member 10232 is free. Although the occlusal end of the spring member 10232 is shown attached to the body, it should be apparent to those of skill in the art that the gingival end of the spring member 10232 may be secured to the body with the occlusal end of the spring member being free.

Figure 95:
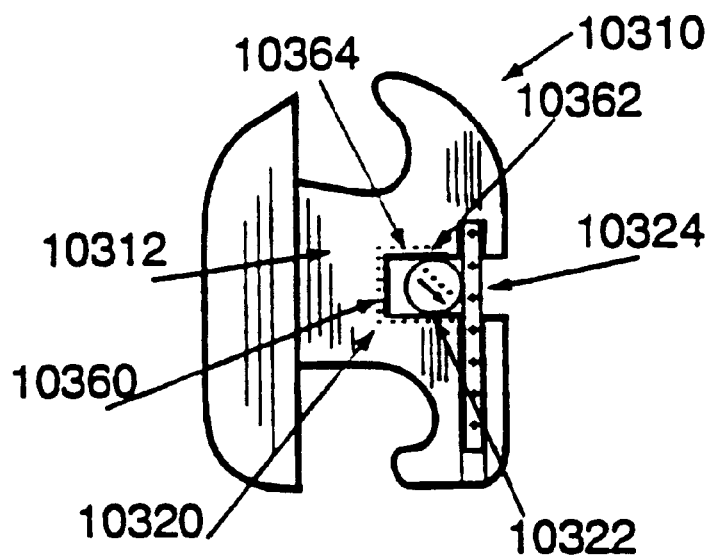
FIG. 95 is a side elevational view of still yet another alternative embodiment of an orthodontic bracket in accordance with the present invention.

FIG. 95 illustrates still yet another embodiment of an orthodontic bracket in accordance with the present invention. In this embodiment, the orthodontic bracket 10310 includes magnetized bars 10360 and 10362 inserted into recesses 10364 formed in the lingual and gingival walls of the body 10312 defining the archwire slot 10320. The magnetized bars 10360 and 10362 are oriented so that they present a magnetic field of the same polarity into the archwire slot 10320. The archwire 10322 to be accommodated in the archwire slot is magnetized to the same polarity as the magnetized bars 10360 and 10362 so that the archwire is repelled and biased labially and occlusally in the archwire slot towards the locking shutter 10324. If desired, the locking shutter can be magnetized to the opposite polarity as the archwire to attract it.

Figure 96A:
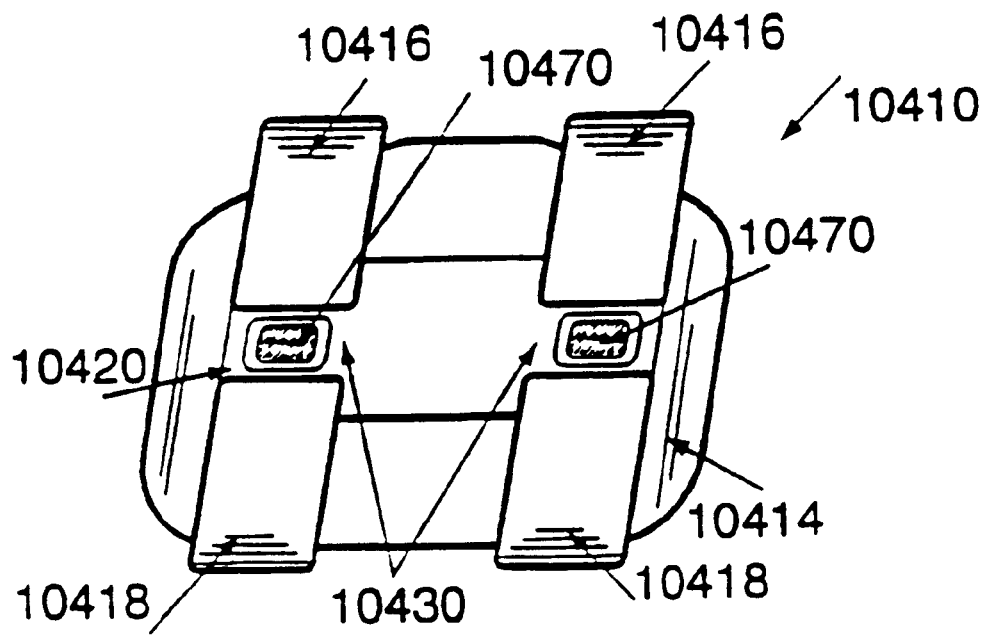
FIGS. 96a and 96b are front elevational and cross-sectional view of another embodiment of an orthodontic bracket in accordance with the present invention.
Figure 96B:
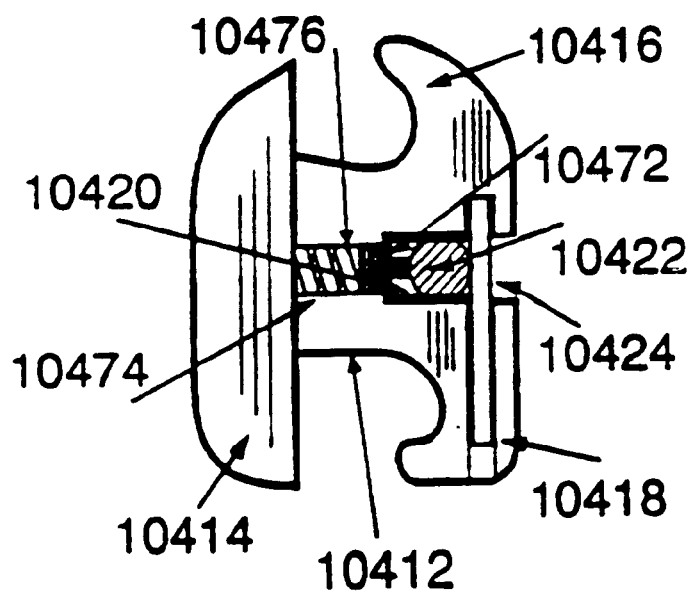

Referring now to FIGS. 96*a* and 96*b,* still yet another embodiment of an orthodontic bracket is shown and is generally indicated to by reference numeral 10410. In this embodiment, the slot activator 10430 is in the form of a pair of spring loaded pistons 10470 extending into the archwire slot 10420 and positioned at opposed mesial and distal ends of the archwire slot between the occlusal and gingival tie wings 10418 and 10416 respectively. Each spring loaded piston 10470 includes a labially extending piston head 10472 to contact an archwire 10422 in the archwire slot. A coil spring 10474 is accommodated in a bore 10476 formed through the body 10412 and acts between the mounting pad 10414 and the back of the piston head 10472 to bias the piston head in a direction towards the locking shutter 10424. The piston heads 10472 are dimensioned to fill approximately one-third to one-hal of the vertical dimension of the archwire slot to inhibit the archwire from sliding up or down and behind the piston head.

Figure 97A:
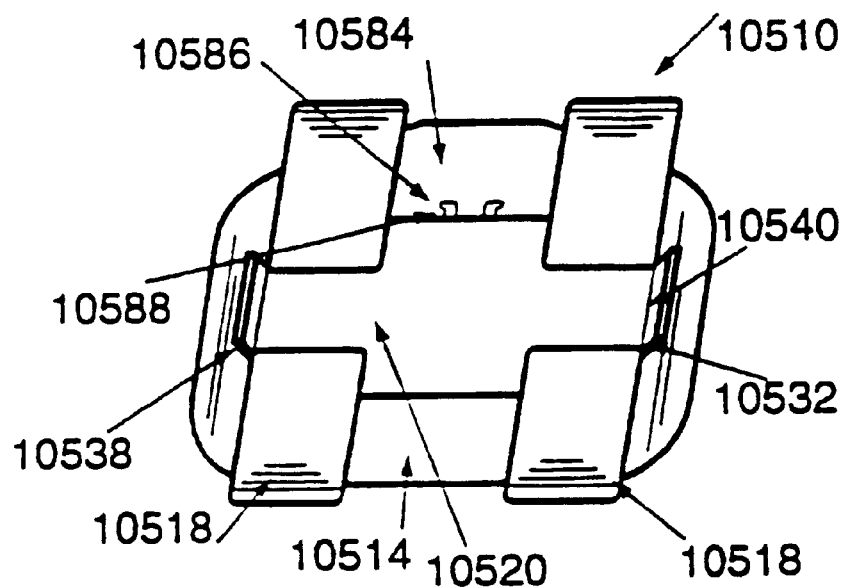
FIGS. 97a to 97c are front elevational, side elevational and top plan views of another embodiment of an orthodontic bracket in accordance with the present invention.
Figure 97B:
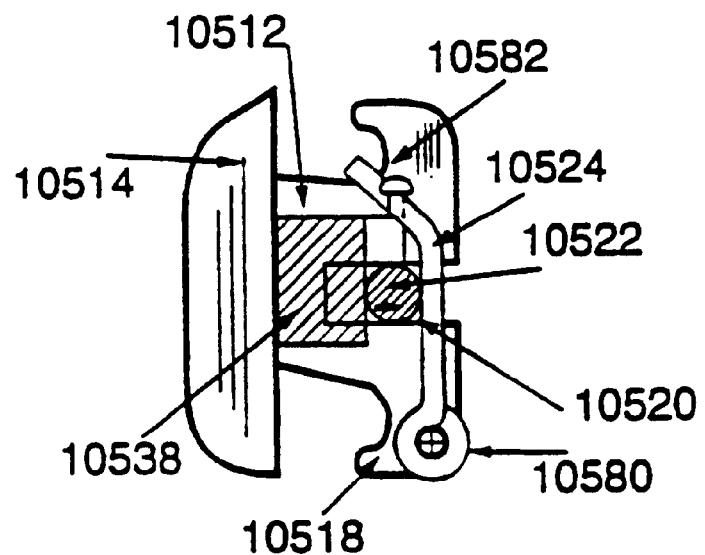
Figure 97C:
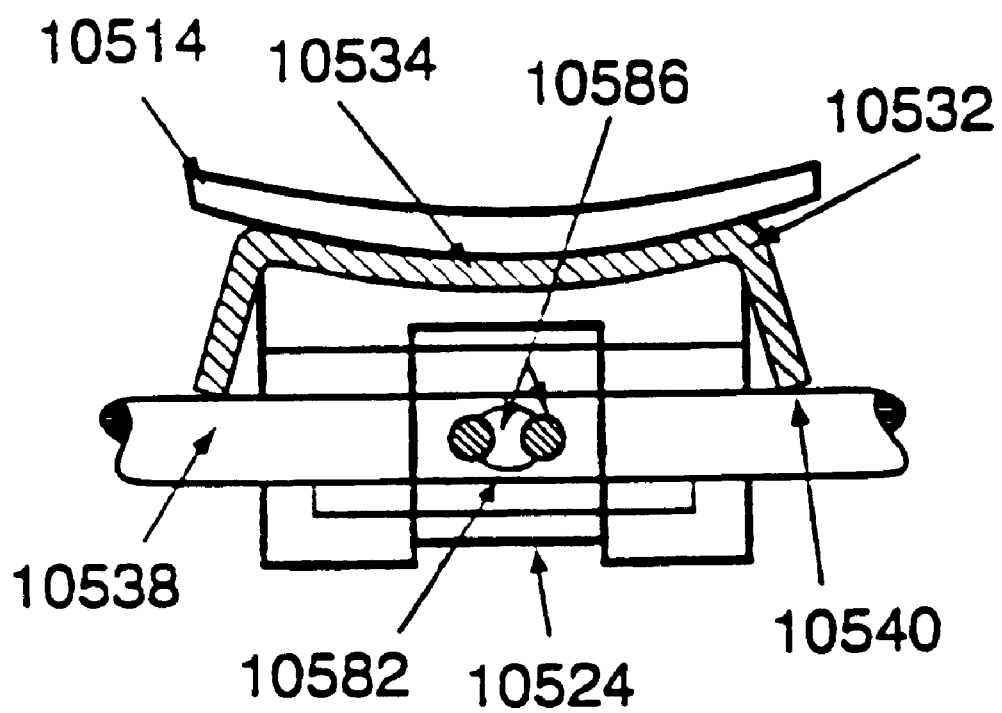

Referring now to FIGS. 97*a* to 97*c* still yet another embodiment of an orthodontic bracket is shown and is generally indicated to by reference numeral 10510. In this embodiment, the slot activator is in the form of a generally rectangular, stainless steel spring member 10532 and is located external to the archwire slot 10520. The spring member 10532 includes a central portion 10534 which runs mesiodistally along the lingual wall of the body 10512 and is trapped between the body 10512 and the lingual mounting pad 10514. Labially extending wings 10538 and 10540 are provided at the mesial and distal ends of the spring member 10532 and contact an archwire 10522 extending along the archwire slot 10520 exterior to the archwire slot near the mesial and distal sides of the body 10512. Thus, the spring member 10532 in this embodiment is external to the archwire slot 10520 but still biases an archwire 10522 in the archwire slot labially towards the locking shutter 10524. The labial extending wings 10538 and 10540 contact the archwire at a lateral angle greater than 90 degrees to facilitate flattening of the labial wings when a large rectangular archwire is accommodated by the archwire slot 10520.

In this embodiment, the locking shutter 10524 includes a single loop adjacent one end to surround a pivot pin 10580 extending between the occlusal tie wings 10518. A hole 10582 is provided in the locking shutter 10524 and co-operates with a pair of spaced projections 10584 extending upwardly from the gingival surface of the body in the interwing region of the orthodontic bracket. Each projection 10584 includes a head 10586 and an undercut stem 10588 supporting the head above the gingival surface of the body. The projections 10584 are spaced a distance slightly greater than the diameter of the hole 10582 so that the heads 10586 must be compressed towards one another to fit into the hole. The undercut stems 10588 allow the projections 10584 to snap back to their original positions once the heads have passed through the hole 10582 thereby to lock the shutter 10524 in place in a closed position.

Figure 98A:
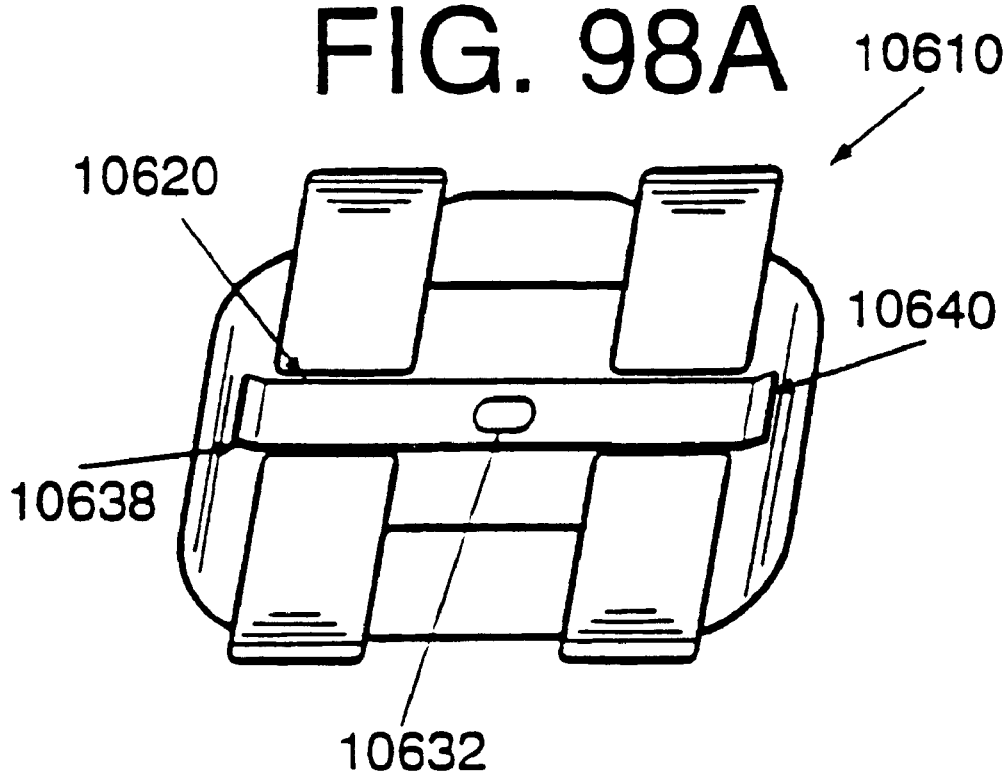
FIGS. 98a and 98b are front elevational and cross-sectional views of another embodiment of an orthodontic bracket in accordance with the present invention.
Figure 98B:
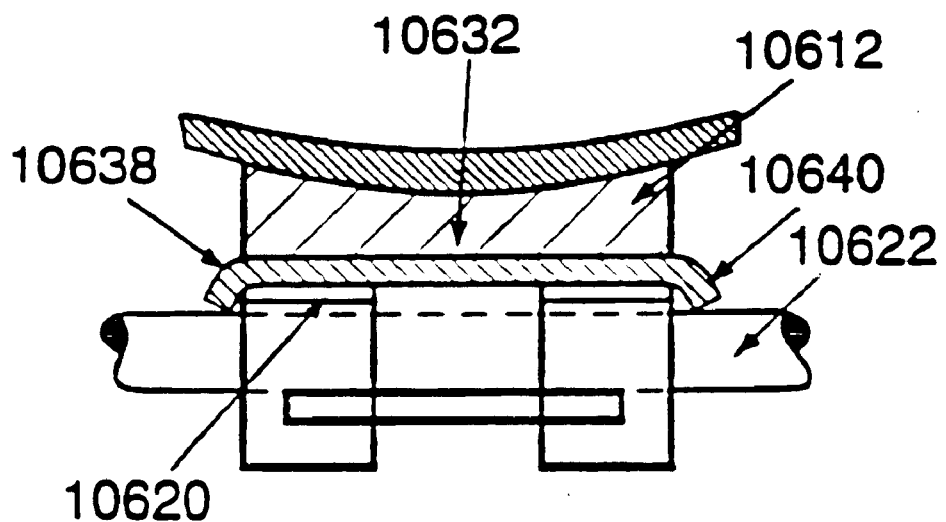

Referring now to FIGS. 98*a* and 98*b,* still yet another embodiment of an orthodontic bracket is shown and is generally indicated to by reference numeral 10610. Orthodontic bracket 10610 is similar to that shown in FIGS. 92*a* to 92*d* except that the ends 10638 and 10640 of the spring member 10632 extend mesiodistally beyond the archwire slot 10620 and contact the archwire 10622 exterior to the archwire slot but near the mesial and distal sides of the body 10612.

Figure 98C:
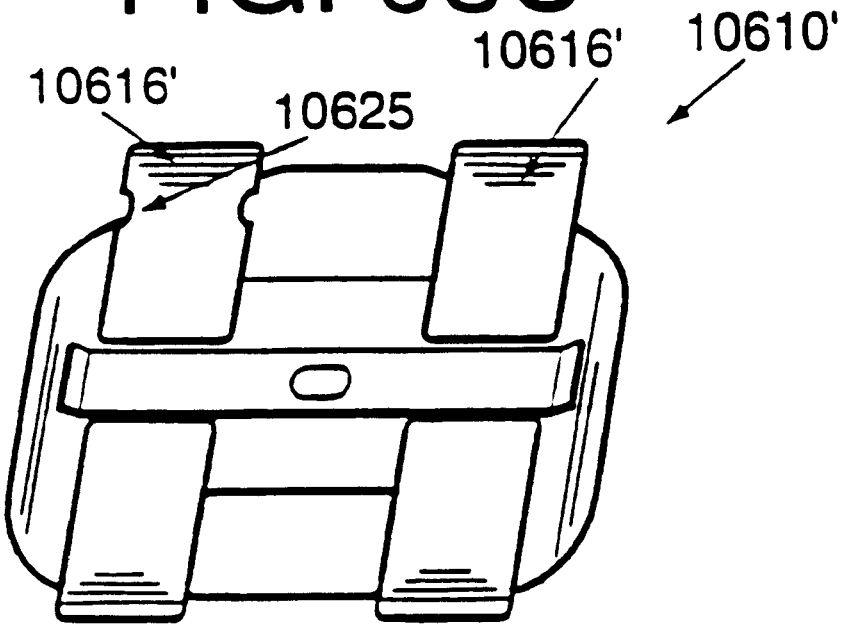
FIGS. 98c and 98d are front and side elevational views of another embodiment of an orthodontic bracket in accordance with the present invention.
Figure 98D:
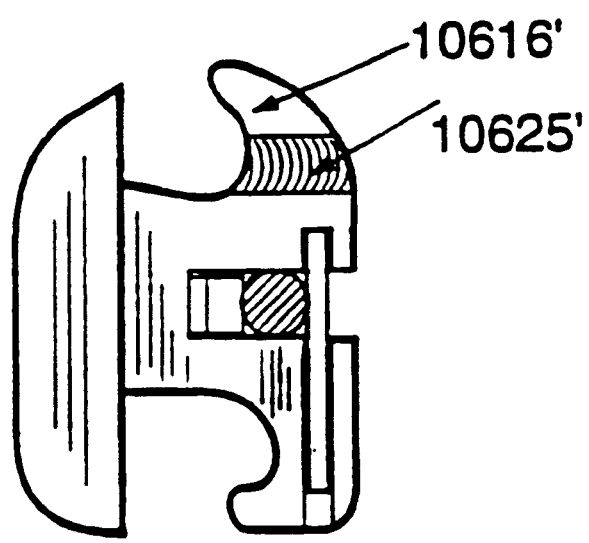

FIGS. 98*c* and 98*d* illustrate another embodiment of an orthodontic bracket 10610' similar to that shown in FIGS. 98*a* and 98*b*. In this embodiment, one of the gingival tie wings 10616' has a pair of grooves 10625 formed in its opposed sides to obviate the need for an upwardly extending hook on the tie wing.

Figure 99A:
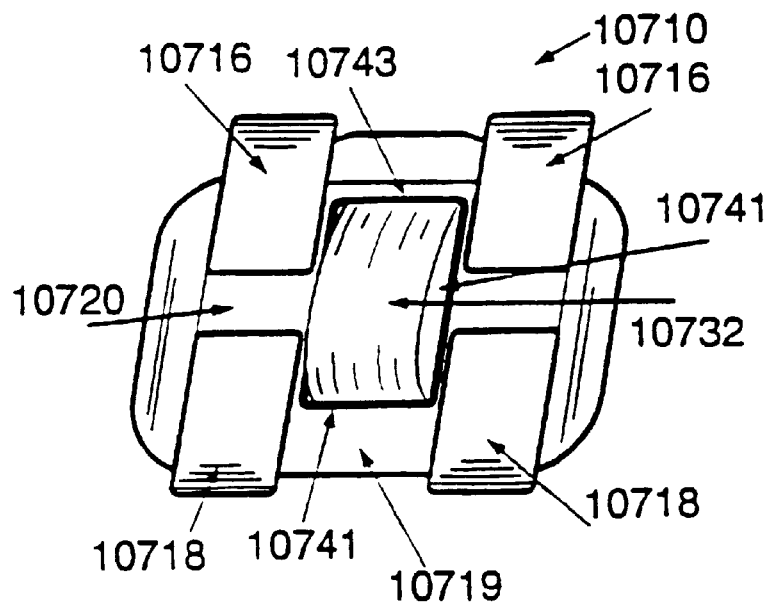
FIGS. 99a and 99b are front and side elevational views of another embodiment of an orthodontic bracket in accordance with the present invention.
Figure 99B:
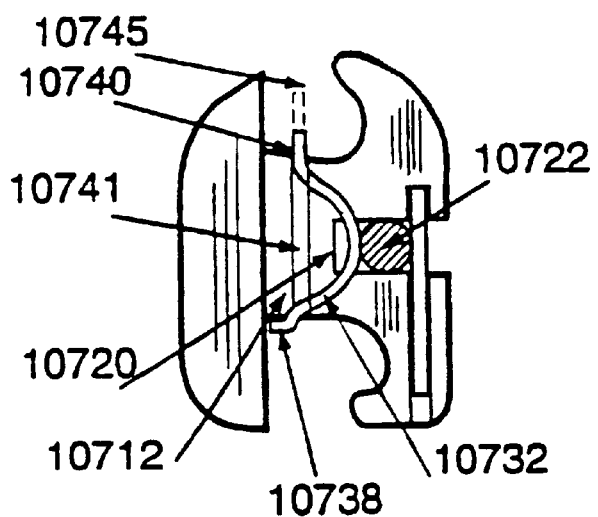

FIGS. 99*a* and 99*b* show still yet another embodiment of an orthodontic bracket 10710. As can be seen, orthodontic bracket 10710 is similar to that illustrated in FIG. 94 and includes an occlusogingivally extending slot activator positioned in the interwing region 10719 between the occlusal and gingival tie wings 10718 and 10716 respectively. The slot activator is in the form of a curved spring member 10732. The spring member passes through a vertical slot 10741 formed in the body 10712 of the orthodontic bracket lingual to the archwire slot 10720 and which opens up at the archwire slot. The occlusal end 10738 of the spring member 10732 is secured to the occlusal surface of the body such as for example by a weld. The gingival end 10740 of the spring member 10732 is free allowing the free end of the spring member to move when the spring member is flattened by an archwire 10722 in the archwire slot 10720 as indicated by the dotted lines 10745.

Figure 100A:
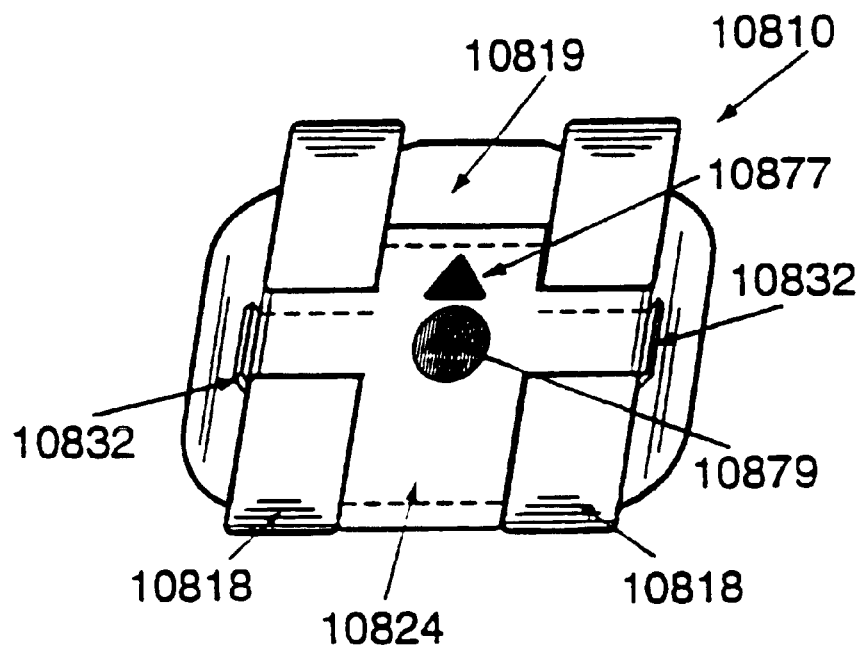
FIGS. 100a and 100c are front elevational, side elevational and top plan views of another embodiment of an orthodontic bracket in accordance with the present invention.
Figure 100B:
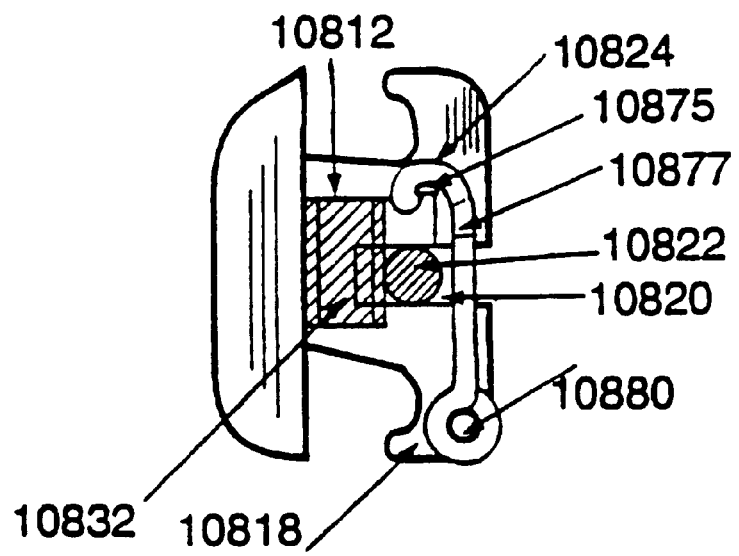
Figure 100C:
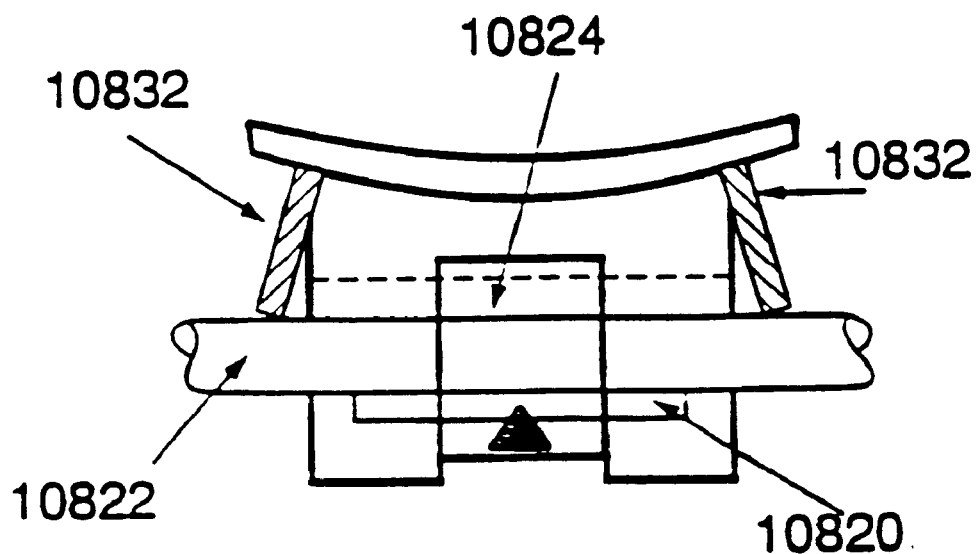

Referring now to FIGS. 100*a* to 100*c* still yet another embodiment of an orthodontic bracket is shown and is generally indicated to by reference numeral 10810. Orthodontic bracket 10810 is similar to that shown in FIGS. 97*a* to 97c and includes a pivotal locking shutter 10824 having a single loop at one end surrounding a pivot pin 10880 extending between the occlusal tie wings 10818. The gingival end of the locking shutter curves occlusally and snaps over a bulbous lip 10875 formed on the gingival surface of the body 10812 in the interwing region 10819 to maintain the locking shutter in the closed condition. An opening 10877 is provided through the locking shutter to accommodate a tool to facilitate opening of the locking shutter. A marker 10879 is also provided on the labial surface of the locking shutter below the opening. The marker identifies the center of the archwire slot 10820 to facilitate proper placement of the orthodontic bracket on the center of the long axis of a tooth. The marker 10879 can of course be provided on the locking shutter 10824 at any suitable location so as to identify the position of the archwire slot. In this particular embodiment, the marker is in the form of a coloured circle on the labial surface of the locking shutter. It should however be apparent that the marker can be of any other suitable form such as for example an embossed or depressed region or a laser marking on the locking shutter.

The slot activator in the embodiment is in the form of a pair of spring members 10832. The spring members extend labially along the mesial and distal sides of the body 10812 and contact an archwire 10822 accommodated by the archwire slot 10820 exterior to the archwire slot but near the mesial and distal sides of the body 10812. The spring members 10832 are secured to the body by welds and contact the archwire at a lateral angle greater than 90 degrees to facilitate flattening of the spring members 10832 when a large rectangular archwire is accommodated by the archwire slot.

Figure 100D:
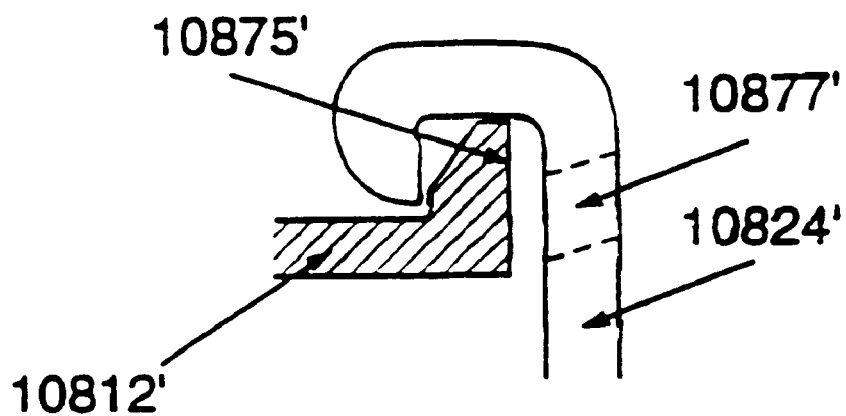
Figure 101A:
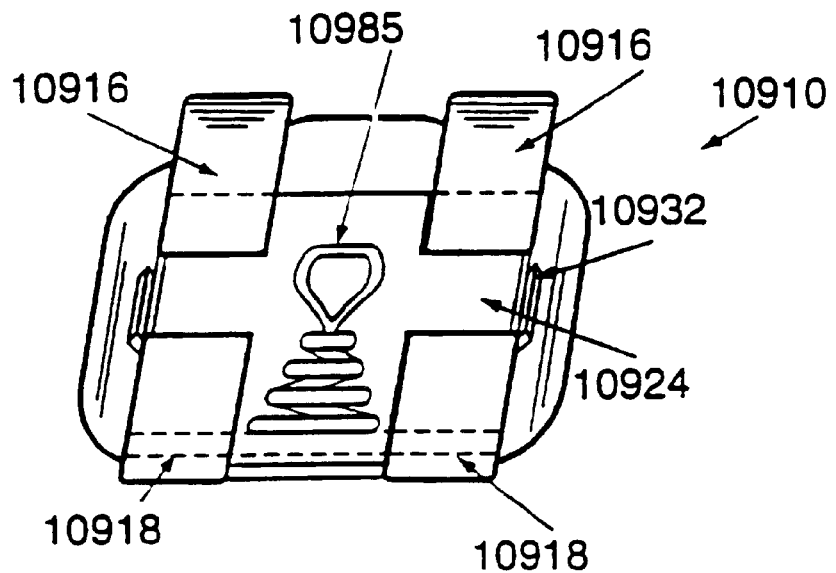
FIGS. 101a to 101c are front elevational, side elevational and top plan views of another embodiment of an orthodontic bracket in accordance with the present invention.
Figure 101B:
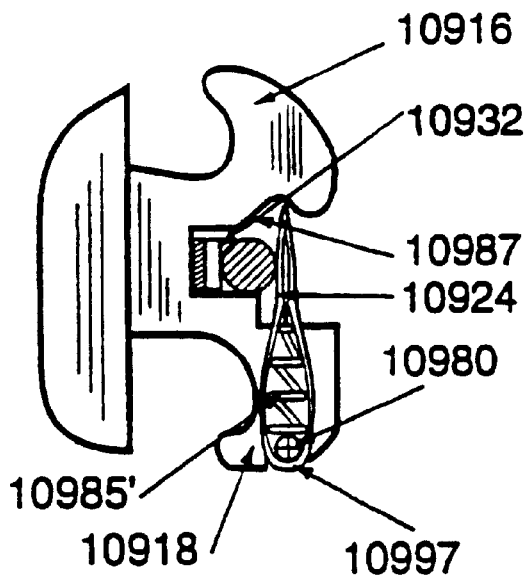
Figure 101C:
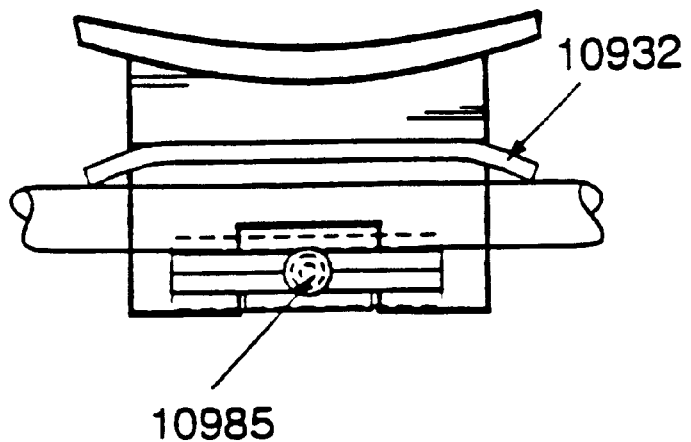
Figure 101D:
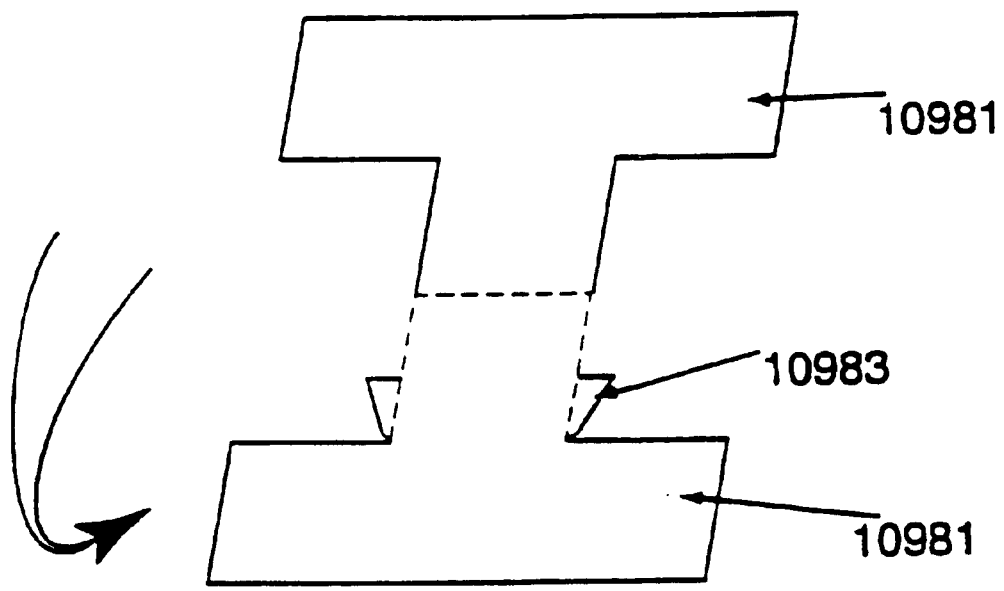
FIG. 101d is a plan view of a locking shutter used in the orthodontic bracket of FIG. 101a in an unfolded condition.

In the embodiment illustrated in FIG. 100*d*, the configuration of the locking shutter 10824' and the lip 10875' on the gingival surface of the body 10812' in the interwing region is modified slightly from that shown in FIGS. 100*a* to 100*c*. In this particular arrangement, the gingival end of the locking shutter 10824' and the lip 10875' are configured as wedges which snap over one another to maintain the locking shutter in the closed condition. The opening 10877' in the locking shutter 10824' accommodates a tool to facilitate pivoting of the locking shutter over the lip 10875 to allow the locking shutter to be pivoted to the open condition.

Referring now to FIGS. 101*a* to 101*d* still yet another embodiment of an orthodontic bracket is shown and is generally indicated to by reference numeral 10910. In this embodiment, the orthodontic bracket includes a slot activator in the form of a spring member 10932 similar to that shown in FIGS. 98*a* and 98*b*. The locking shutter 10924 is however of a different configuration. In particular, the locking shutter 10924 is generally T-shaped in front plan and is constituted by a pair of shutter elements 10981 generally overlying one another and retained in proximity by flaps 10983 integrally formed on one of the shutter elements and which have been folded over the other of the shutter elements. The locking shutter is pivotal about a pivot pin 10980 extending between the occlusal tie wings 10918 and accommodated by recesses 10997 therein. A spring 10985 is welded to the pivot pin 10980 and is also trapped between the shutter elements 10981.

In the closed condition, the locking shutter 10924 is biased by the spring 10985, which acts on the pivot pin 10980, into notches 10987 formed in the occlusal surfaces of the gingival tie wings 10916. When it is desired to release the locking shutter 10924 and move it to an open condition, it is necessary to apply an occlusally directed force on the locking shutter to compress the spring 10985 and move the locking shutter occlusally allowing the gingival end of the locking shutter to clear the notches 10987 and pivot to the open condition. Closing the locking shutter is achieved by performing the above steps in reverse.

Referring now to FIGS. 102 and 103, still yet another embodiment of an orthodontic bracket is shown and is generally indicated to by reference numeral 20010. The orthodontic bracket includes a locking shutter 20024 having a single loop at one end surrounding a pivot pin 20080 extending between the occlusal tie wings 20018. The locking shutter 20024 is pivotal about the pivot pin 20080 between open and closed positions. A locking mechanism is provided on the orthodontic bracket to retain the locking shutter 20024 in the closed condition. The locking mechanism includes an L-shaped arm 20025 extending from the free end of the locking shutter. A wedge 20027 is provided on the locking shutter adjacent the free end. The L-shaped arm and wedge define a channel 20029.

An inverted U-shaped stop 20031 is provided on the body 20012 in the interwing region. The stop 20031 is accommodated by the channel 20029 when the locking shutter 20024 is in the closed condition. In this condition, the resilient nature of the locking shutter brings the wedge 20027 into abutment with the stop 20031 to maintain the locking shutter in the closed condition. To open the locking shutter, an occlusally directed force is applied to the L-shaped arm to flex the locking shutter and slide the wedge 20027 beyond the stop 20031 allowing the locking shutter to pivot to the open condition.

Figure 104:
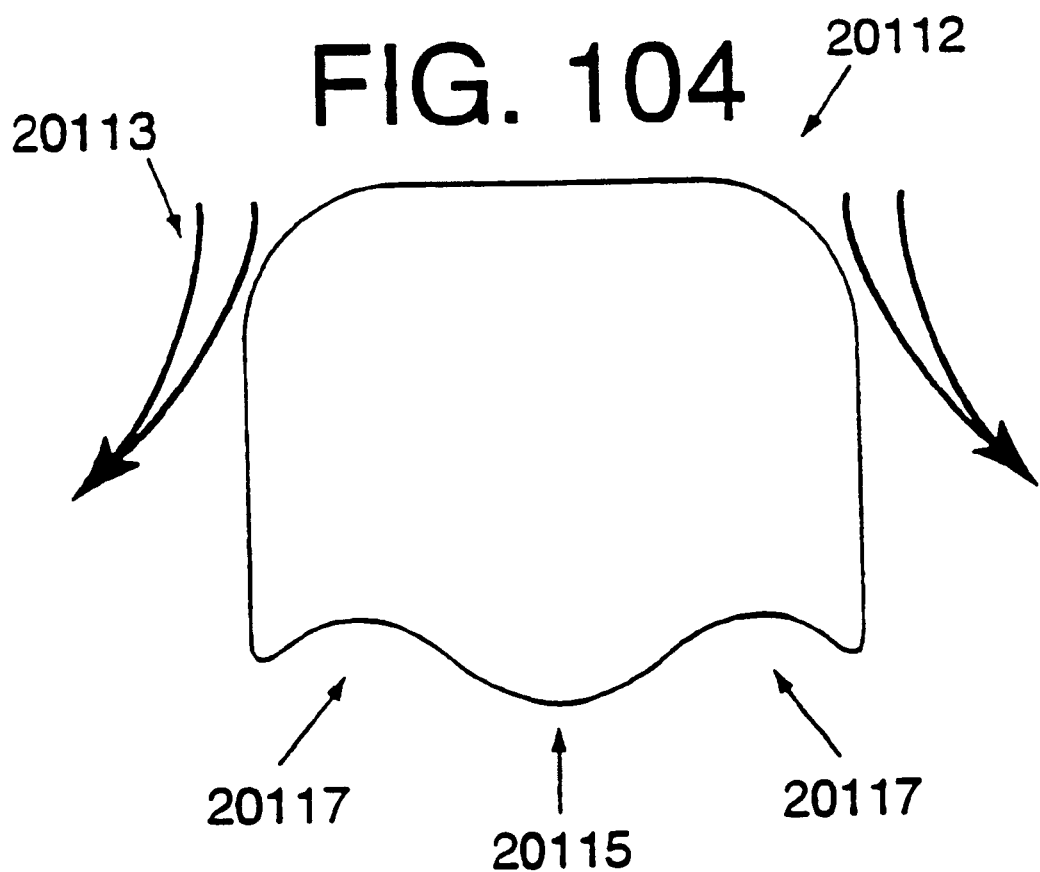
FIG. 104 is a front elevational view of an alternative embodiment of of a body for an orthodontic bracket.

Referring now to FIG. 104, still yet another embodiment of a body for an orthodontic bracket is shown and is generally indicated to by reference numeral 20112. In this embodiment, the body 20112 and mounting pad (now shown) are shaped to deflect food debris and plaque mesially and distally away from the orthodontic bracket in the direction of arrows 20113. Specifically, the gingival surface of the body is rounded and is generally egg-shaped. The occlusal surface of the body 20112 is undulated and has a central formation 20115 thereon defining a pair of curved lateral faces 20117. This body design can be used with any of the described orthodontic brackets.

Figure 105:
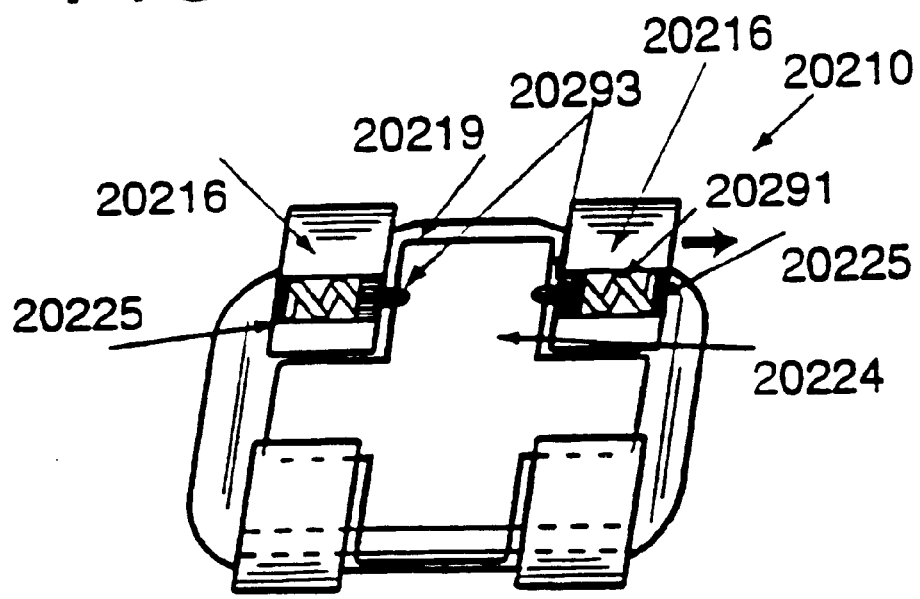
FIGS. 105 and 106 are front and side elevational views of yet another alternative of an orthodontic bracket in accordance with the present invention.
Figure 106:
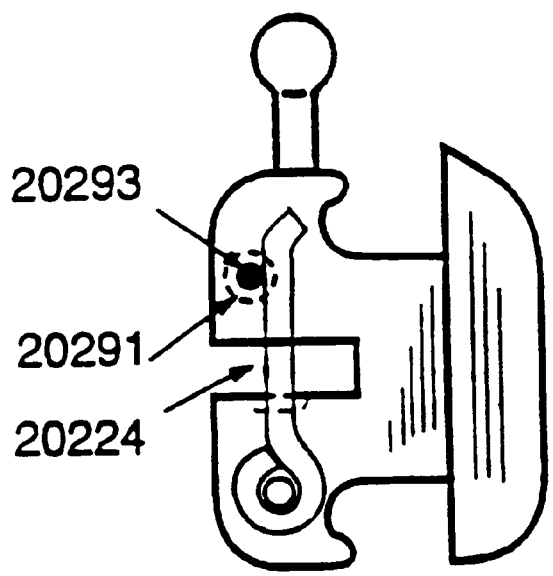
Figure 107A:
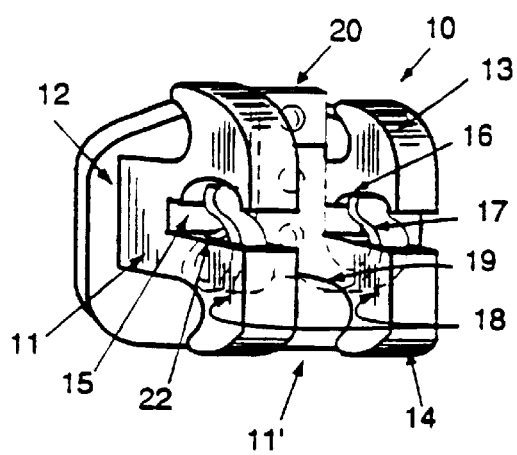
FIG. 107A is a ¾ perspective view of a self-engaging interactive twin orthodontic bracket in accordance with the present invention.
Figure 107B:
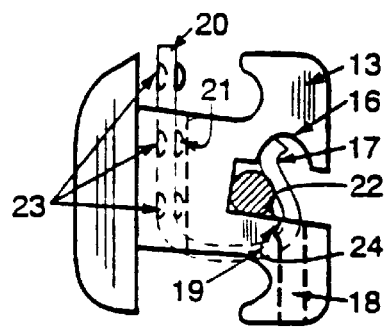
FIG. 107B is a side elevation view of the orthodontic bracket of FIG. 107A.
Figure 107C:
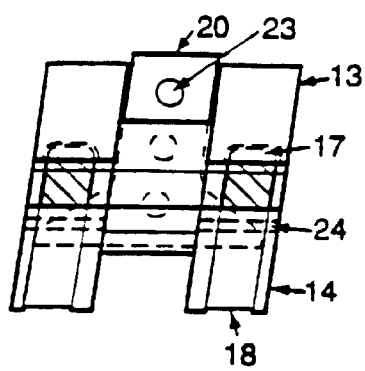
Figure 107D:
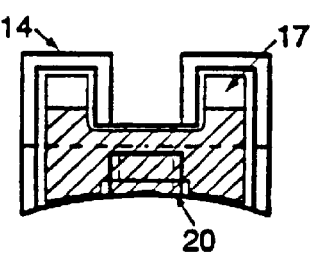
Figure 107E:
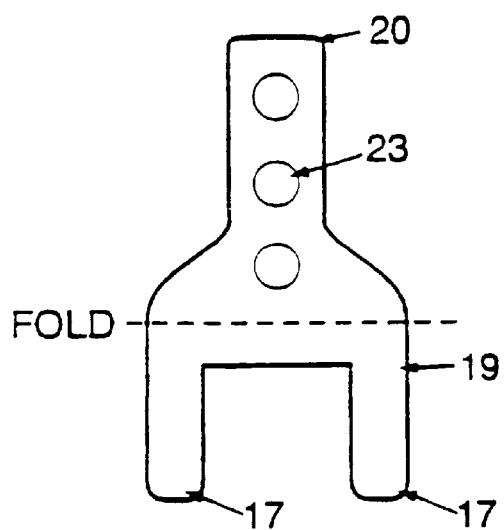
Figure 107F:
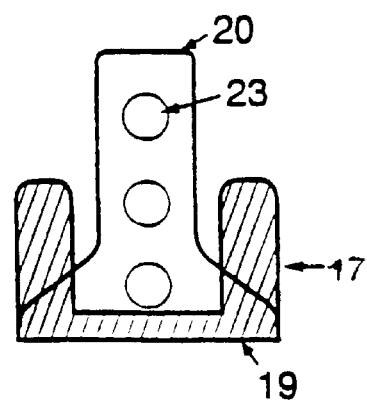
Figure 107G:
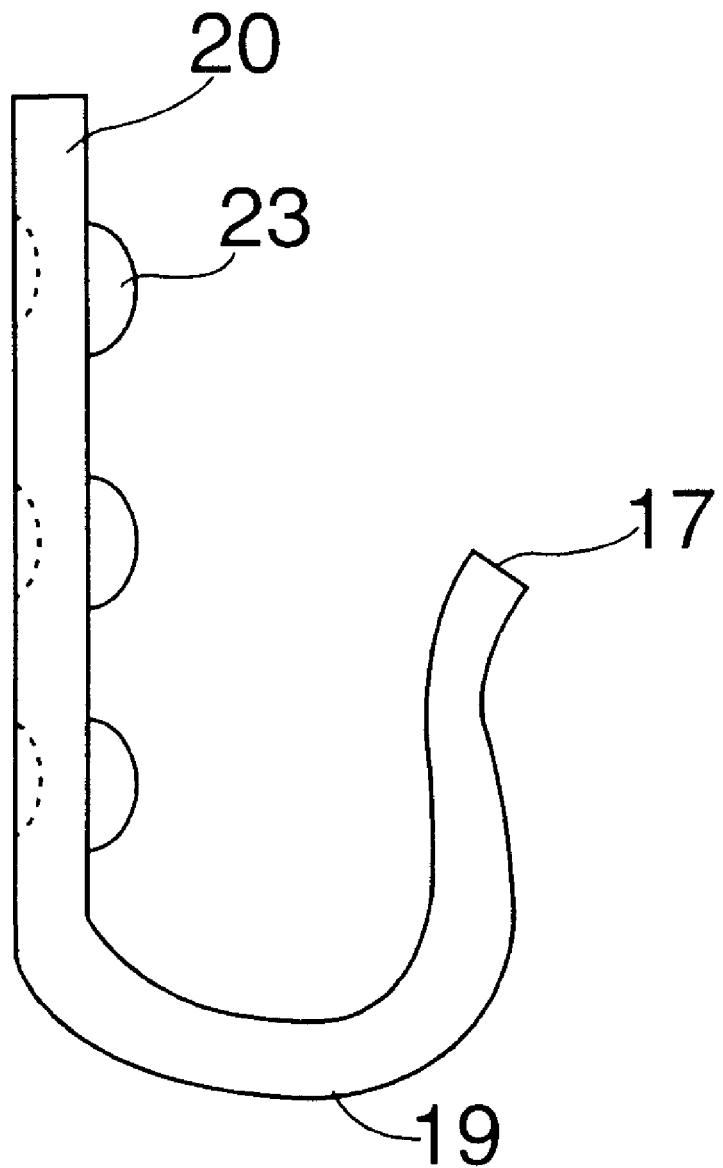

Referring now to FIGS. 105 and 106, still yet another embodiment of an orthodontic bracket is shown and is generally indicated to by reference numeral 20210. In this embodiment, each gingival tie wing 20216 has a spring-loaded piston 20292 therein. The piston heads 20293 extend outwardly of the gingival tie wings into the interwing region 20219 and constitute a retainer for the locking shutter 20224 to maintain the locking shutter in the closed condition. The spring is sealed by a stop 20225 located on the lateral side of the bracket. The pistons 20291 must be biased into the gingival tie wings in order to pivot the locking shutter 20224 to the open condition. As will be appreciated, similar to the embodiments shown in FIGS. 38 to 47, 97*a* to 97*c*, and 100*a* to 103, the locking shutter 20224 includes a single loop surrounding a pivot pin extending between the occlusal tie wings. Although, the pivot pins are illustrated as extending between the occlusal tie wings, those of skill in the art will appreciate that the pivot pin can extend between the gingival tie wings. It should also be appreciated that the locking shutter may include laterally spaced, single loops to surround the pivot pins at laterally spaced mesial and distal locations.

If desired, a lubricating or sealing agent can be applied to the body, locking shutter and/or archwire of the previously described orthodontic brackets.

The orthodontic brackets described above can be formed of any suitable material such as ceramic, plastic or other cosmetic material. If appropriate, the archwire slot may be constituted by a metallic insert accommodated by the body of the orthodontic bracket. Likewise in the case of the embodiment shown in FIGS. 99a and 99b, the vertical slots accommodating the spring member 10732 may also be defined by a metallic inset accommodated by the ceramic body of the orthodontic bracket.

When the orthodontic brackets are to be used to form braces, it is preferred that pre-engaging twin orthodontic brackets of one of the types illustrated herein be used and attached to the central and lateral teeth and first and second molars and that single orthodontic brackets without wings (not shown) be used and applied to the cuspid and premolar teeth. This system of orthodontic brackets provides advantages in that the nature of the single orthodontic brackets are easier to bond to the posterior crowns of the cuspid and premolar teeth. Also, the single orthodontic brackets provide greater interbracket distances allowing for greater archwire flexibility in the posterior middle regions, cuspids and premolars. Better rotational control is however maintained with the use of the twin pre-engaging orthodontic brackets on the central and lateral teeth and first and second molars.

Referring now to FIGS. 107A to 107G, still yet another embodiment of an orthodontic bracket is shown and is generally indicated to by reference numeral 10. As can be seen, orthodontic bracket 10 includes a body 11 and a lingual mounting pad 12 attached to the body. The mounting pad 12 has a lingual surface to be attached to a tooth. A pair of laterally spaced gingival tie-wings 13 and a pair of laterally spaced occlusal tie wings 14 extend from a labial surface of the body 11. The gingival tie wings 13 and the occlusal tie wings 14 curve lingually. An arch wire slot 15 extends mesiodistally across the body and between the gingival and occlusal tie wings at opposed mesial and distal sides of the body and opens labially to receive an arch wire. The arch wire slot 15 is interrupted in the interwing region 11' of the body.

A dome-shaped housing notch 16 is formed in the gingival wall of the arch wire slot 15 at its mesial and distal ends and extends to define mesial and distal semi-circular housing and deflection surfaces 16 to accommodate the labial portions of the arm 17 during the closed positions. Vertical grooves 18 are formed in the lingual surfaces of both occlusal wings 14 to accommodate the occlusal (bottom) portion of the arm 19 (see FIG. 107 B, C, D) in the closed position.

The lingual (back) portion of the arm 20 formed of resilient stainless steel is inserted through a vertical groove 21 in the lingual portion of the bracket body 11. The arm is movable between a closed position where access to the arch wire slot 15 is inhibited and an open position where access to the arch wire slot is permitted. The labial component of the arm 17 is fork-shaped in the flattened position (FIG. 107E) and is in the final state tightly curved (FIG. 107B) The labial arm components are passed behind the occlusal wings 14 through their vertical grooves 18 flexing the arm curvature mildly open to the labial until the labial portions of the arm pass over the occlusal (bottom) aspect of the arch wire slot 22. Once the arm passes arch wire slot and continues to close completely the arm unflexes once again to its normal curved state to prevent arch wire release and to seat the arch wire into the base of the slot.

The lingual portion of the arm 20 has small semi-circular protrusions 23 facing labially that in addition to the compressed curvature of the arm against the occlusal aspect of the arch wire slot, assist the retention of the arm in the closed position. The top protrusion is particularly important to maintain the arm in the open position without letting the arm fall out. In addition, there is a small resting groove 24 located below the arch wire slot on the bracket body to allow the arm to rest within during the open position where it is flexed mildly open further preventing fall-out. The bracket body has at least two complementing depressions in the vertical groove located lingually to accommodate the protrusions of the arm. The arm is opened by pushing vertically in a (occlusal) direction downward on the lingual component of the arm 20 to open the arch wire slot 15.

When the arm 17 is in the closed position and the arch wire applies a labially directed force to the arm 17 the labial surface of the arm 17 contacts the lingual surface of the vertical grooves 18 in the occlusal wings 14 to inhibit the arm from being accidentally removed from the arch wire slot 15. At the same time, the lingual portions of the arm 17 contact the arch wire to urge it continuously back into the arch wire slot 15 over time.

It is to be understood that throughout this application, the term occlusal tire wings may be readily interchanged with the term gingival tie wings and it is also dependent upon the relative positioning of the bracket on the patient's tooth.

An alternate embodiment to the invention is one where the two labial extensions of the arm are joined at their most gingival aspect by a horizontal connector to increase its strength and durability.

Although a number of embodiments of orthodontic brackets have been disclosed, those of skill in the art will appreciate that other variations and/or modifications may be made to the present invention without departing from the scope thereof as defined by the appended claims.

I claim:

1. A self engaging orthodontic bracket for attaching an archwire to a tooth comprising:
    a body including a base for attachment to the tooth, the base having an occlusal-gingivally extending opening, a lingual vertical slot, a pair of laterally spaced gingival tie wings and a pair of laterally placed occlusal tie wings, said gingival and occlusal tie wings projecting from a labial surface of said body, said occlusal tie wings defining two vertical grooves for receiving two arm members of a locking shutter through said occlusal tie wings;
    an archwire slot extending mesiodistally across said body and between the gingival and occlusal tie wings at opposed mesial and distal sides of said body to accommodate the archwire;
    a resilient locking shutter including a lingual guide bar slidably received in said lingual vertical slot and two laterally spaced apart resilient arm members slidably received in said vertical grooves, the locking shutter being movable between an open position in which placement and removal of said archwire is facilitated and a closed position in which placement and removal of said archwire is inhibited; and
    retaining means to releasably retain said arm members in said closed position.

2. A self-engaging orthodontic bracket according to claim 1 wherein said vertical grooves in the occlusal tie wings contacts a labial portion of the arm members to prevent labial distortion of the arm members when in said closed position.

3. A self engaging orthodontic bracket according to claim 1, wherein the retaining means is a dome shape notch formed in an occlusal wall of said gingival tie wings.

4. A self-engaging orthodontic bracket according to claim 3, wherein said notch accommodates a labial portion of the arm members when the shutter is in the closed position.

5. A self-engaging orthodontic bracket according to claim 1, wherein the lingual guide bar includes an upper vertical end section, a tapered region and a broadened lower section for strength.

6. A self-engaging orthodontic bracket according to claim 5, wherein the guide bar is formed of resilient stainless steel, or an alloy of nickel or titanium.

7. A self-engaging orthodontic bracket according to claim 1, wherein the arms are joined at their gingival ends by a horizontal connector.

8. A self-engaging orthodontic bracket according to claim 1, wherein the lingual guide bar includes a plurality of projecting members formed thereon, and said body includes complimentary depressions formed thereon for releasably accepting said projecting members.

9. A self-engaging orthodontic bracket according to claim 1, wherein the body further defines a resting groove located below or above the archwire slot for retaining the arm when the shutter is in the open position.

10. A self engaging orthodontic bracket for attaching an archwire to a tooth comprising:

a body including a base for attachment to the tooth, the base having an occlusal-gingivally extending opening, a lingual vertical slot, a pair of laterally spaced gingival tie wings and a pair of laterally placed occlusal tie wings, said gingival and occlusal tie wings projecting from a labial surface of said body, said gingival tie wings defining two vertical grooves for receiving two arm members of a locking shutter through said gingival tie wings;

an archwire slot extending mesiodistally across said body and between the gingival and occlusal tie wings at opposed mesial and distal sides of said body to accommodate the archwire;

a resilient locking shutter including a lingual guide bar slidably received in said lingual vertical slot and two laterally spaced apart resilient arm members slidably received in said vertical grooves, the locking shutter being movable between an open position in which placement and removal of said archwire is facilitated and a closed position in which placement and removal of said archwire is inhibited; and retaining means to releasably retain said arm members in said closed position.

11. A self-engaging orthodontic bracket according to claim 10 wherein said vertical grooves in the gingival tie wings contacts a labial portion of the arm members to prevent labial distortion of the arm members when in said closed position.

12. A self-engaging orthodontic bracket according to claim 10, wherein the arms are joined at their occlusal ends by a horizontal connector.

13. A self engaging orthodontic bracket according to claim 10, wherein the retaining means is a dome shape notch formed in a gingival wall of said gingival tie wings.

14. A self-engaging orthodontic bracket according to claim 13, wherein said notch accomodates a labial portion of the arm members when the shutter is in the closed position.

* * * * *

USO06168428C1

(12) EX PARTE REEXAMINATION CERTIFICATE (9877th)
United States Patent
Voudouris

(10) Number: US 6,168,428 C1
(45) Certificate Issued: Oct. 17, 2013

(54) ORTHODONTIC BRACKET

(75) Inventor: John C. Voudouris, Willowdale (CA)

(73) Assignee: Orthoarm Incorporated, Toronto, Ontario (CA)

Reexamination Request:
No. 90/020,021, Sep. 14, 2012

Reexamination Certificate for:
Patent No.: 6,168,428
Issued: Jan. 2, 2001
Appl. No.: 09/308,194
Filed: Jul. 23, 1999

(21) Appl. No.: 90/020,021

(22) PCT Filed: Nov. 12, 1997

(86) PCT No.: PCT/CA97/00865
§ 371 (c)(1),
(2), (4) Date: Jul. 23, 1999

(87) PCT Pub. No.: WO98/20805
PCT Pub. Date: May 22, 1998

(51) Int. Cl.
*A61C 3/00* (2006.01)

(52) U.S. Cl.
USPC ............................................ 433/11; 433/13

(58) Field of Classification Search
None
See application file for complete search history.

(56) References Cited

To view the complete listing of prior art documents cited during the proceeding for Reexamination Control Number 90/020,021, please refer to the USPTO's public Patent Application Information Retrieval (PAIR) system under the Display References tab.

*Primary Examiner* — Beverly M. Flanagan

(57) ABSTRACT

In one embodiment, a pre-engaging orthodontic bracket includes a body having a lingual surface for attachment to a tooth, a pair of laterally spaced gingival tie wings and a pair of laterally spaced occlusal tie wings. The gingival and occlusal tie wings project from a labial surface of the body. An archwire slot extends mesiodistally across the body and between the gingival and occlusal tie wings at opposed mesial and distal sides of the body to accomodate an archwire. A shutter is moveable between an open position in which placement and removal of an archwire is facilitated, and a closed position in which placement and removal of an archwire is inhibited.

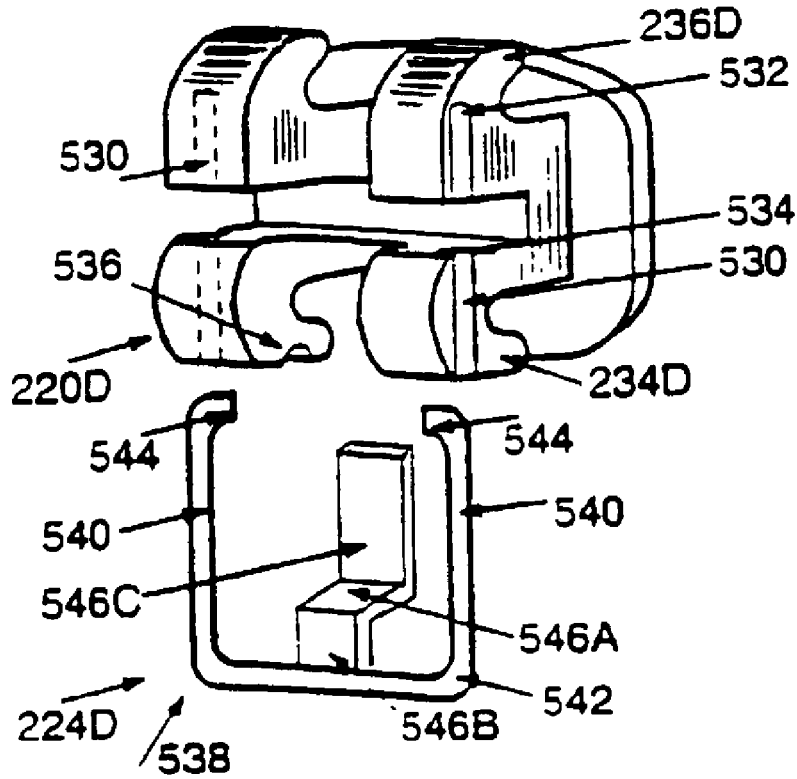

US 6,168,428 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 10 and 11 are determined to be patentable as amended.

Claims 7-9 and 12, dependent on an amended claim, are determined to be patentable.

New claims 15-38 are added and determined to be patentable.

Claims 3-6, 13 and 14 were not reexamined.

1. A self engaging orthodontic bracket for attaching an archwire to a tooth comprising:
   a body including a base for attachment to the tooth, the base having an occlusal-gingivally extending opening, a lingual vertical slot, a pair of laterally spaced gingival tie wings and a pair of laterally placed occlusal tie wings, said gingival and occlusal tie wings projecting from a labial surface of said body, said occlusal tie wings defining two vertical grooves for receiving two arm members of a locking shutter through said occlusal tie wings;
   an archwire slot extending mesiodistally across said body and between the gingival and occlusal tie wings at opposed mesial and distal sides of said body to accommodate the archwire;
   a resilient locking shutter including a lingual guide bar slidably received in said lingual vertical slot, *wherein said lingual guide bar has a lateral width and said lingual guide bar is substantially solid across said lateral width,* and two laterally spaced apart resilient arm members slidably received in said vertical grooves, the locking shutter being movable between an open position in which placement and removal of said archwire is facilitated and a closed position in which placement and removal of said archwire is inhibited; and
   retaining means to releasably retain said arm members in said closed position.

2. A self-engaging orthodontic bracket [according to claim 1] *for attaching an archwire to a tooth comprising:*
   *a body including a base for attachment to the tooth, the base having an occlusal-gingivally extending opening, a lingual vertical slot, a pair of laterally spaced gingival tie wings and a pair of laterally placed occlusal tie wings, said gingival and occlusal tie wings projecting from a labial surface of said body, said occlusal tie wings defining two vertical grooves for receiving two arm members of a locking shutter through said occlusal tie wings;*
   *an archwire slot extending mesiodistally across said body and between the gingival and occlusal tie wings at opposed mesial and distal sides of said body to accommodate the archwire;*
   *a resilient locking shutter including a lingual guide bar slidably received in said lingual vertical slot and two laterally spaced apart resilient arm members slidably received in said vertical grooves, the locking shutter being movable between an open position in which placement and removal of said archwire is facilitated and a closed position in which placement and removal of said archwire is inhibited; and*
   *retaining means to releasably retain said arm members in said closed position;*
   wherein said vertical grooves in the occlusal tie wings contacts a labial portion of the arm members to prevent labial distortion of the arm members when in said closed position.

10. A self engaging orthodontic bracket for attaching an archwire to a tooth comprising:
    a body including a base for attachment to the tooth, the base having an occlusal-gingivally extending opening, a lingual vertical slot, a pair of laterally spaced gingival tie wings and a pair of laterally placed occlusal tie wings, said gingival and occlusal tie wings projecting from a labial surface of said body, said gingival tie wings defining two vertical grooves for receiving two arm members of a locking shutter through said gingival tie wings;
    an archwire slot extending mesiodistally across said body and between the gingival and occlusal tie wings at opposed mesial and distal sides of said body to accommodate the archwire;
    a resilient locking shutter including a lingual guide bar slidably received in said lingual vertical slot, *wherein said lingual guide bar has a lateral width and said lingual guide bar is substantially solid across said lateral width,* and two laterally spaced apart resilient arm members slidably received in said vertical grooves, the locking shutter being movable between an open position in which placement and removal of said archwire is facilitated and a closed position in which placement and removal of said archwire is inhibited; and
    retaining means to releasably retain said arm members in said closed position.

11. A self-engaging orthodontic bracket [according to claim 10] *for attaching an archwire to a tooth comprising:*
    *a body including a base for attachment to the tooth, the base having an occlusal-gingivally extending opening, a lingual vertical slot, a pair of laterally spaced gingival tie wings and a pair of laterally placed occlusal tie wings, said gingival and occlusal tie wings projecting from a labial surface of said body, said gingival tie wings defining two vertical grooves for receiving two arm members of a locking shutter through said gingival tie wings;*
    *an archwire slot extending mesiodistally across said body and between the gingival and occlusal tie wings at opposed mesial and distal sides of said body to accommodate the archwire;*
    *a resilient locking shutter including a lingual guide bar slidably received in said lingual vertical slot and two laterally spaced apart resilient arm members slidably received in said vertical grooves, the locking shutter being movable between an open position in which placement and removal of said archwire is facilitated and a closed position in which placement and removal of said archwire is inhibited; and*
    *retaining means to releasably retain said arm members in said closed position;*
    wherein said vertical grooves in the gingival tie wings contacts a labial portion of the arm members to prevent labial distortion of the arm members when in said closed position.

15. A self-engaging orthodontic bracket according to claim 2, wherein the retaining means is a dome shape notch formed in an occlusal wall of said gingival tie wings.

16. A self-engaging orthodontic bracket according to claim 15, wherein said notch accommodates a labial portion of the arm members when the shutter is in the closed position.

17. A self-engaging orthodontic bracket according to claim 2, wherein the lingual guide bar includes an upper vertical end section, a tapered region and a broadened lower section for strength.

18. A self-engaging orthodontic bracket according to claim 17, wherein the guide bar is formed of resilient stainless steel, or an alloy of nickel or titanium.

19. A self-engaging orthodontic bracket according to claim 2, wherein the arms are joined at their gingival ends by a horizontal connector.

20. A self-engaging orthodontic bracket according to claim 2, wherein the lingual guide bar includes a plurality of projecting members formed thereon, and said body includes complimentary depressions formed thereon for releasably accepting said projecting members.

21. A self-engaging orthodontic bracket according to claim 2, wherein the body further defines a resting groove located below or above the archwire slot for retaining the arm when the shutter is in the open position.

22. A self-engaging orthodontic bracket according to claim 11, wherein the arms are joined at their occlusal ends by a horizontal connector.

23. A self-engaging orthodontic bracket according to claim 11, wherein the retaining means is a dome shape notch formed in a gingival wall of said gingival tie wings.

24. A self-engaging orthodontic bracket according to claim 23, wherein said notch accommodates a labial portion of the arm members when the shutter is in the closed position.

25. A self-engaging orthodontic bracket according to claim 1 wherein said lingual vertical slot has a lateral width, and wherein said lingual guide bar has a lateral width substantially corresponding to the lateral width of said lingual vertical slot.

26. A self-engaging orthodontic bracket according to claim 25 wherein said guide bar maintains alignment of said locking shutter as said shutter is moved between said open and closed positions.

27. A self-engaging orthodontic bracket according to claim 1 wherein said guide bar maintains alignment of said locking shutter as said shutter is moved between said open and closed positions.

28. A self-engaging orthodontic bracket according to claim 1 wherein said lateral width of said guide bar is substantially greater than the thickness of said guide bar.

29. A self-engaging orthodontic bracket according to claim 25 wherein said lateral width of said guide bar is substantially greater than the thickness of said guide bar.

30. A self-engaging orthodontic bracket according to claim 1 wherein said guide bar is substantially planar across its lateral width.

31. A self-engaging orthodontic bracket according to claim 29 wherein said guide bar is substantially planar across its lateral width.

32. A self-engaging orthodontic bracket according to claim 10 wherein said lingual vertical slot has a lateral width, and wherein said lingual guide bar has a lateral width substantially corresponding to the lateral width of said lingual vertical slot.

33. A self-engaging orthodontic bracket according to claim 32 wherein said guide bar maintains alignment of said locking shutter as said shutter is moved between said open and closed positions.

34. A self-engaging orthodontic bracket according to claim 10 wherein said guide bar maintains alignment of said locking shutter as said shutter is moved between said open and closed positions.

35. A self-engaging orthodontic bracket according to claim 10 wherein said lateral width of said guide bar is substantially greater than the thickness of said guide bar.

36. A self-engaging orthodontic bracket according to claim 32 wherein said lateral width of said guide bar is substantially greater than the thickness of said guide bar.

37. A self-engaging orthodontic bracket according to claim 10 wherein said guide bar is substantially planar across its lateral width.

38. A self-engaging orthodontic bracket according to claim 36 wherein said guide bar is substantially planar across its lateral width.

\* \* \* \* \*